(12) United States Patent
De Visser et al.

(10) Patent No.: US 11,345,915 B2
(45) Date of Patent: *May 31, 2022

(54) RNA MODULATING OLIGONUCLEOTIDES WITH IMPROVED CHARACTERISTICS FOR THE TREATMENT OF NEUROMUSCULAR DISORDERS

(71) Applicant: VICO Therapeutics B.V., Leiden (NL)

(72) Inventors: Peter Christian De Visser, Leiden (NL); Susan Allegonda Maria Mulders, Groesbeek (NL)

(73) Assignee: VICO THERAPEUTICS B.V., Leiden (NL)

( * ) Notice: Subject to any disclaimer, the term of this patent is extended or adjusted under 35 U.S.C. 154(b) by 133 days.

This patent is subject to a terminal disclaimer.

(21) Appl. No.: 16/660,416

(22) Filed: Oct. 22, 2019

(65) Prior Publication Data

US 2020/0149043 A1    May 14, 2020

Related U.S. Application Data

(60) Continuation of application No. 15/676,569, filed on Aug. 14, 2017, now abandoned, which is a division of application No. 14/522,002, filed on Oct. 23, 2014, now Pat. No. 9,745,576, which is a continuation of application No. PCT/NL2013/050306, filed on Apr. 23, 2013.

(60) Provisional application No. 61/636,914, filed on Apr. 23, 2012.

(30) Foreign Application Priority Data

Apr. 23, 2012   (EP) .................................. 12165139.2

(51) Int. Cl.
    C12N 15/113          (2010.01)
(52) U.S. Cl.
    CPC ........ *C12N 15/113* (2013.01); *C12N 2310/11* (2013.01); *C12N 2310/315* (2013.01); *C12N 2310/321* (2013.01); *C12N 2310/333* (2013.01); *C12N 2310/334* (2013.01); *C12N 2310/335* (2013.01); *C12N 2310/336* (2013.01); *C12N 2310/3341* (2013.01); *C12N 2310/346* (2013.01); *C12N 2310/3521* (2013.01); *C12N 2320/34* (2013.01)

(58) Field of Classification Search
    None
    See application file for complete search history.

(56) References Cited

U.S. PATENT DOCUMENTS

| 5,945,290 A | 8/1999 | Cowsert |
| 7,514,551 B2 | 4/2009 | Rabbani et al. |
| 7,655,785 B1 | 2/2010 | Bentwich |
| 8,263,760 B2 | 9/2012 | De Kimpe et al. |
| 9,057,066 B2 | 6/2015 | Hung et al. |
| 2003/0109476 A1 | 6/2003 | Kmiec et al. |
| 2005/0277133 A1 | 12/2005 | McSwiggen |
| 2006/0074034 A1 | 4/2006 | Collins et al. |
| 2007/0299027 A1 | 12/2007 | Hung et al. |
| 2008/0015158 A1 | 1/2008 | Ichiro et al. |
| 2010/0184833 A1 | 7/2010 | De Kimpe |
| 2011/0184050 A1 | 7/2011 | De Kimpe et al. |

FOREIGN PATENT DOCUMENTS

| CN | 101501193 A | 8/2009 |
| CN | 101980726 A | 2/2011 |
| WO | WO 94/28175 A1 | 12/1994 |
| WO | WO 95/30774 A1 | 11/1995 |
| WO | WO 2003/004511 A2 | 1/2003 |
| WO | WO 03/013437 A2 | 2/2003 |
| WO | WO 2006/031267 A2 | 3/2006 |
| WO | WO 2006/083800 A2 | 8/2006 |
| WO | WO 2007/044362 A2 | 4/2007 |
| WO | WO 2008/018795 A1 | 2/2008 |
| WO | WO 2009/008727 A2 | 1/2009 |
| WO | WO 2009/099326 A1 | 8/2009 |
| WO | WO 2010/006237 A2 | 1/2010 |
| WO | WO 2010/014592 A1 | 2/2010 |
| WO | WO 2010/144485 A1 | 12/2010 |
| WO | WO 2011/097614 A1 | 8/2011 |
| WO | WO 2011/097641 A1 | 8/2011 |
| WO | WO 2012/012443 A2 | 1/2012 |
| WO | WO 2012/021985 A1 | 2/2012 |
| WO | WO 2012/109395 A1 | 8/2012 |
| WO | WO 2012/150960 A1 | 11/2012 |
| WO | WO 2013/082548 A1 | 6/2013 |
| WO | WO 2013/120003 A1 | 8/2013 |

OTHER PUBLICATIONS

Atdbio, Ltd., "DNA Duplex Stability," http://ww.atdbio.com/content/53/DNA-duplex-stability, 10 pages, 2008.
Boado et al., "Antisense-mediated down-regulation of the human huntingtin gene," J. Pharmacol. Exp. Ther. 295(1):239-243 (2000).
Bonifazi et al., "Use of RNA fluorescence in situ hybridization in the prenatal molecular diagnosis of myotonic dystrophy type I," Clin. Chem. 52(2):319-322 (2006).
Buczko, W., et al., "Modulation of Plasminogen Activator Inhibitor Type-I Biosynthesis in Vitro and in Vivo with Oligo(nucleoside phosphorothioate)s and Related Constructs," Pharmacology & Therapeutics, vol. 76, No. 1-3, DD. 161-175, 1997.
Caplen et al., "Rescue of polyglutamine-mediated cytotoxicity by double-stranded RNA-mediated RNA interference," Hum. Mol. Genet. 11(2):175-184 (2002).
Cooper, "Molecular biology. Neutralizing toxic RNA," Science 325(5938):272-273 (2009).

(Continued)

Primary Examiner — Tracy Vivlemore
(74) Attorney, Agent, or Firm — Lathrop GPM LLP; James H. Velema, Esq.

(57) ABSTRACT

The current invention provides an improved oligonucleotide and its use for treating, ameliorating, preventing, delaying and/or treating a human cis-element repeat instability associated genetic neuromuscular or neurodegenerative disorder.

25 Claims, 2 Drawing Sheets

Specification includes a Sequence Listing.

(56) References Cited

OTHER PUBLICATIONS

Devor et al., "Oligonucleotide Yield, Resuspension, and Storage," Integrated DNA Technologies, pp. 1-11, 2005.
Eder et al., "Inhibition of LncaP prostate cancer cells by means of androgen receptor antisense oligonucleotides," Cancer Gene Ther. 7(7):997-1007 (2000).
Elayadi et al., "Application of PNA and LNA oligomers to chemotherapy," Curr. Opin. Investig. Drugs 2(4):558-561 (2001).
Evers et al., "Targeting several CAG expansion diseases by a single antisense oligonucleotide," PLoS One 6(9):e24308 (2011) (Epub Sep. 1, 2011).
Fiszer et al., "An evaluation of oligonucleotide-based therapeutic strategies forpolyQ diseases," BMC Mol. Biol. 13:6 (2012).
Folini et al., "Antisense oligonucleotide-mediated inhibition of hTERT, but not hTERC, induces rapid cell growth decline and apoptosis in the absence of telomere shortening in human prostate cancer cells," Eur. J. Cancer41(4):624-634 (2005) (Epub Jan. 20, 2005).
Fu et al., "An unstable triplet repeat in a gene related to myotonic muscular dystiophy," Science 255(5049): 1256-1258 (1992).
Furling et al., "Viral vector producing antisense RNA restores myotonic dystrophy myoblast functions," Gene Ther. 10(9):795-802 (2003).
Gagnon et al., "Allele-selective inhibition of mutant huntingtin expression with antisense oligonucleotides targeting the expanded CAG repeat," Biochemistry Nov. 30, 2010;49(47):10166-10178 (2010) (Epub Nov. 8, 2010).
Galderisi et al., "Myotonic dystrophy: antisense oligonucleotide inhibition of DMPK gene expression in vitro," Biochem. Biophys. Res. Commun. 221(3):750-754 (1996).
Handa et al., "The AUUCU repeats responsible for spinocerebellar ataxia type 10 form unusual RNA hairpins," J. Biol. Chem. 280(32):29340-29345 (2005) (Epub Jun. 20, 2005).
Harrison et al., "Synthesis and hybridization analysis of a small library of peptide-oligonucleotide conjugates," Nucleic Acids Res. 26(13):3136-4315 (1998).
Hasholt et al., "Antisense downregulation of mutant huntingtin in a cell model," J. Gene Med. 5(6):528-538 (2003).
Kandimalla et al., "Effects of phosphorothioate oligodeoxyribonucleotide and oligoribonucleotides on human complement and coagulation," Bioorg. Med. Chem. Lett. 8(16):2103-2108 (1998).
Lebedev et al., "Oligonucleotides containing 2-aminoadenine and 5-methylcytosine are more effective as primers for PCR amplification than their nonmodified counterparts," Genet. Anal. 13(1):15-21 (1996).
Lee et al., "RNase H-mediated degradation of toxic RNA in myotonic dystrophy type I," Proc. Natl. Acad. Sci. U.S.A. 109(11):4221-4226 (2012) (Epub Feb. 27, 2012).
Liu, W., et al., "Specific Inhibition of Huntington's Disease Gene Expression By siRNAs in Cultured Cells," Proceedings of the Japan Academy, 2003, vol. 79, pp. 293-298.
Magaña et al., "Perspectives on gene therapy in myotonic dystrophy type I," J. Neurosci. Res. 89(3):275-285 (2011) (Epub Dec. 16, 2010).
Mulders et al., "Molecular therapy in myotonic dystrophy: focus on RNA gain-of-function," Hum. Mol. Genet. 19(R1):R90-R97 (2010) (Epub Apr. 20, 2010).
Mulders et al., "Triplet-repeat oligonucleotide-mediated reversal of RNA toxicity in myotonic dystrophy," Proc. Natl. Acad. Sci. U.S.A. 106(33):13915-13920 (2009) (Epub Aug. 10, 2009).
Muntoni et al., "Targeting RNA to treat neuromuscular disease," Nat. Rev. Drug Discov. 10(8):621-637 (2011).
Nakamori et al., "Stabilization of expanded (CTG)•(CAG) repeats by antisense oligonucleotides," Mol. Ther. 19(12):2222-2227 (2011) (Epub Oct. 4, 2011).
Sah et al., "Oligonucleotide therapeutic approaches for Huntington disease," J. Clin. Invest. 121(2):500-507 (2011) (Epub Feb. 1, 2011).
Sun et al., "Phosphorodiamidate morpholino oligomers suppress mutant huntingtin expression and attenuate neurotoxicity," Hum. Mol. Genet. 23(23):6302-6317 (2014) (Epub Jul. 4, 2014).
Taneja, "Localization oftrinucleotide repeat sequences in myotonic dystrophy cells using a single fluorochrome-labeled PNA probe," BioTechniques 24(3):472-476 (1998).
Thomsen et al., "Dramatically improved RNA in situ hybridization signals using LNA-modified probes," RNA 11(11):1745-1748 (2005) (Epub Sep. 21, 2005).
United States Patent and Trademark Office, International Search Report for International Patent Application No. PCT/NL2013/050306, dated Jul. 19, 2013, 6 pages.
Wheeler et al., "Reversal of RNA dominance by displacement of protein sequestered on triplet repeat RNA," Science 325(5938):336-339 (2009).

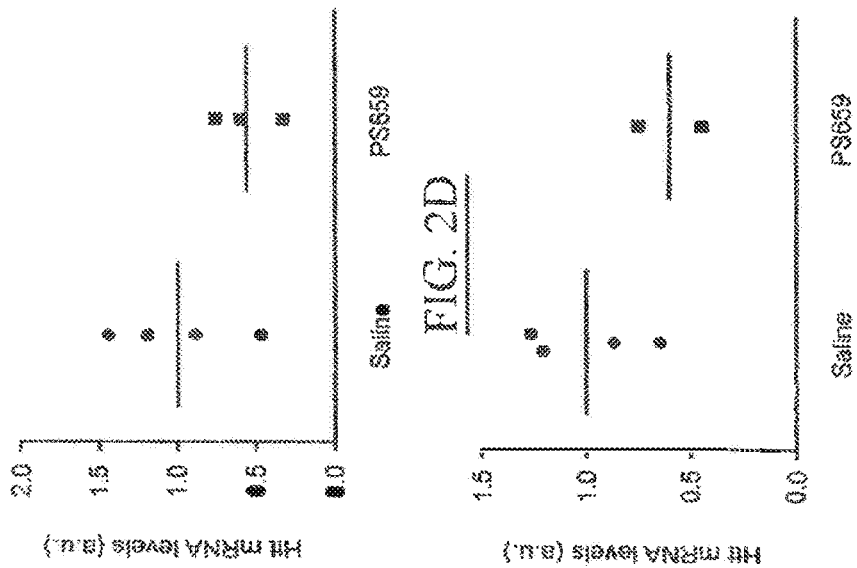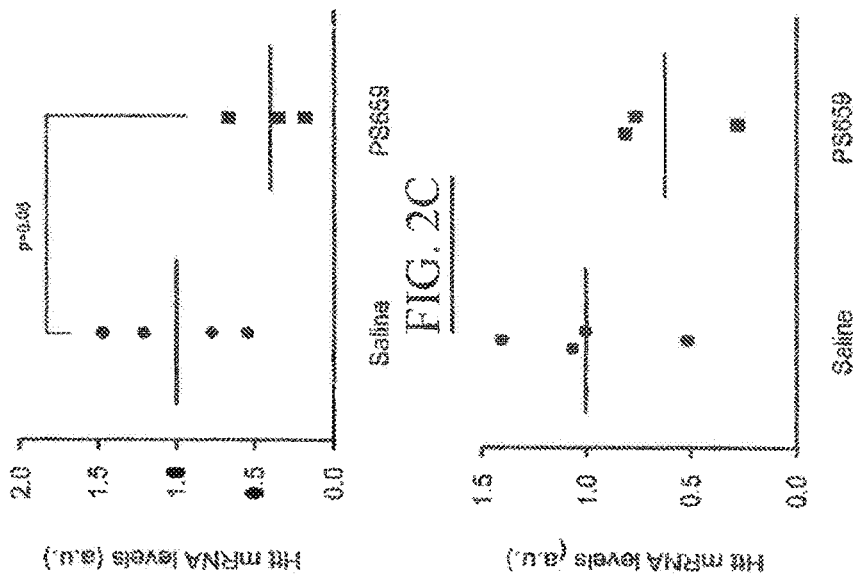

SEQUENCE LISTING

```
<160> NUMBER OF SEQ ID NOS: 221

<210> SEQ ID NO 1
<211> LENGTH: 21
<212> TYPE: RNA
<213> ORGANISM: Artificial
<220> FEATURE:
<223> OTHER INFORMATION: Oligonucleotide

<400> SEQUENCE: 1
cugcugcugc ugcugcugcu g                                           21

<210> SEQ ID NO 2
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
```

```
<222> LOCATION: (19)..(19)
<223> OTHER INFORMATION: n is 5-methylcytosine

<400> SEQUENCE: 2
nugnugnugn ugnugnugnu g                                           21

<210> SEQ ID NO 3
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 3
cngcngcngc ngcngcngcn g                                           21

<210> SEQ ID NO 4
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
```

```
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil

<400> SEQUENCE: 4
nngnngnngn ng                                                              12

<210> SEQ ID NO 5
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil

<400> SEQUENCE: 5
nngnngnngn ngnng                                                           15

<210> SEQ ID NO 6
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
```

-continued

```
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil

<400> SEQUENCE: 6
nngnngnngn ngnngnng                                            18

<210> SEQ ID NO 7
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
```

```
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil

<400> SEQUENCE: 7
nngnngnngn ngnngnngnn g                                        21

<210> SEQ ID NO 8
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
```

```
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil

<400> SEQUENCE: 8
nngnngnngn ngnngnngnn gnng                                              24

<210> SEQ ID NO 9
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
```

```
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil

<400> SEQUENCE: 9
nngnngnngn ngnngnngnn gnngnng                                     27

<210> SEQ ID NO 10
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
```

```
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is U or 5-methyluracil

<400> SEQUENCE: 10
nngnngnngn ngnngnngnn gnngnngnng                                     30

<210> SEQ ID NO 11
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
```

```
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is U or 5-methyluracil

<400> SEQUENCE: 11
nngnngnngn ngnngnngnn gnngnngnng nng                          33

<210> SEQ ID NO 12
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is U or 5-methyluracil
<220> FEATURE:
```

<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is U or 5-methyluracil
<220> FEATURE:
<221> NAME/KEY: misc_feature
<222> LOCATION: (34)..(34)
<223> OTHER INFORMATION: n is C or 5-methylcytosine
<220> FEATURE:
<221> NAME/KEY: misc_feature
<222> LOCATION: (35)..(35)
<223> OTHER INFORMATION: n is U or 5-methyluracil

<400> SEQUENCE: 12
nngnngnngn ngnngnngnn gnngnngnng nngnng                                36

<210> SEQ ID NO 13
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine

<400> SEQUENCE: 13
ngnngnngnn gn                                                          12

<210> SEQ ID NO 14
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine

```
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine

<400> SEQUENCE: 14
ngnngnngnn gnngn                                                    15

<210> SEQ ID NO 15
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
```

<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine

<400> SEQUENCE: 15
ngnngnngnn gnngnngn                                                 18

<210> SEQ ID NO 16
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine

<400> SEQUENCE: 16
ngnngnngnn gnngnngnng n             21

<210> SEQ ID NO 17
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 17
ngnngnngnn gnngnngnng nngn                                          24

<210> SEQ ID NO 18
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine

```
<220> FEATURE:
<221> NAME/KEY: misc_feature
<222> LOCATION: (27)..(27)
<223> OTHER INFORMATION: n is C or 5-methylcytosine

<400> SEQUENCE: 18
ngnngnngnn gnngnngnng nngnngn                                            27

<210> SEQ ID NO 19
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
```

```
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine

<400> SEQUENCE: 19
ngnngnngnn gnngnngnng nngnngnngn                                           30

<210> SEQ ID NO 20
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
```

```
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine

<400> SEQUENCE: 20
ngnngnngnn gnngnngnng nngnngnngn ngn                             33

<210> SEQ ID NO 21
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
```

```
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is C or 5-methylcytosine
<220> FEATURE:
<221> NAME/KEY: misc_feature
<222> LOCATION: (36)..(36)
<223> OTHER INFORMATION: n is C or 5-methylcytosine

<400> SEQUENCE: 21
ngnngnngnn gnngnngnng nngnngnngn ngnngn                36

<210> SEQ ID NO 22
<211> LENGTH: 12
<212> TYPE: RNA
<213> ORGANISM: Artificial
<220> FEATURE:
<223> OTHER INFORMATION: Oligonucleotide
```

```
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine

<400> SEQUENCE: 22
nngnngnngn ng                                                         12

<210> SEQ ID NO 23
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
```

<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine

<400> SEQUENCE: 23
nngnngnngn ngnng                                                        15

<210> SEQ ID NO 24
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine

<400> SEQUENCE: 24
nngnngnngn ngnngnng                                                     18

<210> SEQ ID NO 25
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature

```
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine

<400> SEQUENCE: 25
nngnngnngn ngnngnngnn g                                       21

<210> SEQ ID NO 26
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
```

<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine

<400> SEQUENCE: 26
nngnngnngn ngnngnngnn gnng                                    24

<210> SEQ ID NO 27
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine

```
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine

<400> SEQUENCE: 27
nngnngnngn ngnngnngnn gnngnng                                          27

<210> SEQ ID NO 28
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
```

```
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is C or 5-methylcytosine

<400> SEQUENCE: 28
nngnngnngn ngnngnngnn gnngnngnng                                        30

<210> SEQ ID NO 29
<211> LENGTH: 33
<212> TYPE: RNA
<213> ORGANISM: Artificial
```

```
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
```

<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is C or 5-methylcytosine

<400> SEQUENCE: 29
nngnngnngn ngnngnngnn gnngnngnng nng                          33

<210> SEQ ID NO 30
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (8)..(8)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (20)..(20)
<223> OTHER INFORMATION: n is C or 5-methylcytosine -continued

```
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (32)..(32)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is C or 5-methylcytosine
<220> FEATURE:
<221> NAME/KEY: misc_feature
<222> LOCATION: (35)..(35)
<223> OTHER INFORMATION: n is C or 5-methylcytosine

<400> SEQUENCE: 30
nngnngnngn ngnngnngnn gnngnngnng nngnng                                   36

<210> SEQ ID NO 31
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
```

```
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine

<400> SEQUENCE: 31
nnnnnnnnnn nn                                                            12

<210> SEQ ID NO 32
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
```

<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine

<400> SEQUENCE: 32
nnnnnnnnnn nnnnn                                                    15

<210> SEQ ID NO 33
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:

```
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine

<400> SEQUENCE: 33
nnnnnnnnnn nnnnnnnn                                                18

<210> SEQ ID NO 34
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
```

<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine

<400> SEQUENCE: 34
nnnnnnnnnn nnnnnnnnnn n                                                  21

<210> SEQ ID NO 35
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)

```
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine

<400> SEQUENCE: 35
nnnnnnnnnn nnnnnnnnnn nnnn                                      24

<210> SEQ ID NO 36
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
```

```
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine

<400> SEQUENCE: 36 nnnnnnnnn nnnnnnnnnn nnnnnnn                                    27

<210> SEQ ID NO 37
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
```

```
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is U or 5-methyluracil
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (30)..(30)
```

<223> OTHER INFORMATION: n is C or 5-methylcytosine

<400> SEQUENCE: 37
nnnnnnnnnn nnnnnnnnnn nnnnnnnnnn                          30

<210> SEQ ID NO 38
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature

```
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is U or 5-methyluracil
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is U or 5-methyluracil
<220> FEATURE:
<221> NAME/KEY: misc_feature
<222> LOCATION: (32)..(32)
<223> OTHER INFORMATION: n is U or 5-methyluracil
<220> FEATURE:
<221> NAME/KEY: misc_feature
<222> LOCATION: (33)..(33)
<223> OTHER INFORMATION: n is C or 5-methylcytosine

<400> SEQUENCE: 38 nnnnnnnnn nnnnnnnnnn nnnnnnnnnn nnn                                   33

<210> SEQ ID NO 39
<211> LENGTH: 36
<212> TYPE: RNA
<213> ORGANISM: Artificial
<220> FEATURE:
<223> OTHER INFORMATION: Oligonucleotide
<220> FEATURE:
```

```
<221> NAME/KEY: misc_feature
<222> LOCATION: (1)..(1)
<223> OTHER INFORMATION: n is U or 5-methyluracil
<220> FEATURE:
<221> NAME/KEY: misc_feature
<222> LOCATION: (2)..(2)
<223> OTHER INFORMATION: n is U or 5-methyluracil
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is U or 5-methyluracil
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is U or 5-methyluracil
<220> FEATURE:
<221> NAME/KEY: misc_feature
<222> LOCATION: (8)..(8)
<223> OTHER INFORMATION: n is U or 5-methyluracil
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is U or 5-methyluracil
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is U or 5-methyluracil
<220> FEATURE:
<221> NAME/KEY: misc_feature
<222> LOCATION: (14)..(14)
<223> OTHER INFORMATION: n is U or 5-methyluracil
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is U or 5-methyluracil
<220> FEATURE:
<221> NAME/KEY: misc_feature
<222> LOCATION: (17)..(17)
<223> OTHER INFORMATION: n is U or 5-methyluracil
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is U or 5-methyluracil
<220> FEATURE:
<221> NAME/KEY: misc_feature
<222> LOCATION: (20)..(20)
<223> OTHER INFORMATION: n is U or 5-methyluracil
```

```
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is U or 5-methyluracil
<220> FEATURE:
<221> NAME/KEY: misc_feature
<222> LOCATION: (23)..(23)
<223> OTHER INFORMATION: n is U or 5-methyluracil
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is U or 5-methyluracil
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is U or 5-methyluracil
<220> FEATURE:
<221> NAME/KEY: misc_feature
<222> LOCATION: (29)..(29)
<223> OTHER INFORMATION: n is U or 5-methyluracil
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is U or 5-methyluracil
<220> FEATURE:
<221> NAME/KEY: misc_feature
<222> LOCATION: (32)..(32)
<223> OTHER INFORMATION: n is U or 5-methyluracil
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is U or 5-methyluracil
<220> FEATURE:
<221> NAME/KEY: misc_feature
<222> LOCATION: (35)..(35)
<223> OTHER INFORMATION: n is U or 5-methyluracil
<220> FEATURE:
<221> NAME/KEY: misc_feature
<222> LOCATION: (36)..(36)
<223> OTHER INFORMATION: n is C or 5-methylcytosine

<400> SEQUENCE: 39
nnnnnnnnnn nnnnnnnnnn nnnnnnnnnn nnnnnn                             36

<210> SEQ ID NO 40
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
```

```
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine

<400> SEQUENCE: 40
ggnggnggng gn                                                     12

<210> SEQ ID NO 41
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine

<400> SEQUENCE: 41
ggnggnggng gnggn                                                  15

<210> SEQ ID NO 42
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
```

<222> LOCATION: (18)..(18)
<223> OTHER INFORMATION: n is C or 5-methylcytosine

<400> SEQUENCE: 42
ggnggnggng gnggnggn                                         18

<210> SEQ ID NO 43
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine

<400> SEQUENCE: 43
ggnggnggng gnggnggngg n                                     21

<210> SEQ ID NO 44
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:

```
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 44 ggngqnggng gnggnggngg nggn                                    24

<210> SEQ ID NO 45
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine

<400> SEQUENCE: 45
ggnggnggng gnggnggngg nggnggn                                 27

<210> SEQ ID NO 46
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
```

```
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine

<400> SEQUENCE: 46
ggnggnggng gnggnggngg nggnggnggn                                         30

<210> SEQ ID NO 47
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (30)..(30)
```

```
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine

<400> SEQUENCE: 47
ggnggnggng gnggnggngg nggnggnggn ggn                                33

<210> SEQ ID NO 48
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine
<220> FEATURE:
<221> NAME/KEY: misc_feature
<222> LOCATION: (27)..(27)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is C or 5-methylcytosine
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (36)..(36)
<223> OTHER INFORMATION: n is C or 5-methylcytosine

<400> SEQUENCE: 48
ggnggnggng gnggnggngg nggnggnggn ggnggn                             36

<210> SEQ ID NO 49
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine

<400> SEQUENCE: 49
nggnggnggn gg                                                          12

<210> SEQ ID NO 50
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine

<400> SEQUENCE: 50
nggnggnggn ggngg                                                       15

<210> SEQ ID NO 51
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
```

```
<221> NAME/KEY: misc_feature
<222> LOCATION: (16)..(16)
<223> OTHER INFORMATION: n is C or 5-methylcytosine

<400> SEQUENCE: 51
nggnggnggn ggnggngg                                                    18

<210> SEQ ID NO 52
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine

<400> SEQUENCE: 52
nggnggnggn ggnggnggng g                                                21

<210> SEQ ID NO 53
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
```

<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine

<400> SEQUENCE: 53
nggnggnggn ggnggnggng gngg                                              24

<210> SEQ ID NO 54
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine

<400> SEQUENCE: 54
nggnggnggn ggnggnggng gnggngg                                           27

<210> SEQ ID NO 55
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)

```
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine

<400> SEQUENCE: 55
nggnggnggn ggnggnggng gnggnggngg                                       30

<210> SEQ ID NO 56
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
```

```
<222> LOCATION: (28)..(28)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine

<400> SEQUENCE: 56
nggnggnggn ggnggnggng gnggnggngg ngg                          33

<210> SEQ ID NO 57
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is C or 5-methylcytosine
<220> FEATURE:
<221> NAME/KEY: misc_feature
<222> LOCATION: (7)..(7)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is C or 5-methylcytosine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is C or 5-methylcytosine
<220> FEATURE:
<221> NAME/KEY: misc_feature
<222> LOCATION: (19)..(19)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is C or 5-methylcytosine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (28)..(28)
<223> OTHER INFORMATION: n is C or 5-methylcytosine
<220> FEATURE:
<221> NAME/KEY: misc_feature
<222> LOCATION: (31)..(31)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is C or 5-methylcytosine

<400> SEQUENCE: 57
nggnggnggn ggnggnggng gnggnggngg nggngg                       36

<210> SEQ ID NO 58
<211> LENGTH: 15
<212> TYPE: RNA
<213> ORGANISM: Artificial
<220> FEATURE:
<223> OTHER INFORMATION: Oligonucleotide
<220> FEATURE:
```

```
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil

<400> SEQUENCE: 58
ngnnnngnnn ngnnn                                                   15

<210> SEQ ID NO 59
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
```

```
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine
<220> FEATURE:
<221> NAME/KEY: misc_feature
<222> LOCATION: (20)..(20)
<223> OTHER INFORMATION: n is U or 5-methyluracil

<400> SEQUENCE: 59
ngnnnngnnn ngnnnngnnn                                            20

<210> SEQ ID NO 60
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
```

```
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is A or 2,6-diaminopurine
<220> FEATURE:
<221> NAME/KEY: misc_feature
<222> LOCATION: (23)..(23)
<223> OTHER INFORMATION: n is A or 2,6-diaminopurine
<220> FEATURE:
<221> NAME/KEY: misc_feature
<222> LOCATION: (24)..(24)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is U or 5-methyluracil

<400> SEQUENCE: 60
ngnnnngnnn ngnnnngnnn ngnnn                                           25

<210> SEQ ID NO 61
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
```

```
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is A or 2,6-diaminopurine
<220> FEATURE:
<221> NAME/KEY: misc_feature
<222> LOCATION: (23)..(23)
<223> OTHER INFORMATION: n is A or 2,6-diaminopurine
<220> FEATURE:
<221> NAME/KEY: misc_feature
<222> LOCATION: (24)..(24)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (28)..(28)
<223> OTHER INFORMATION: n is A or 2,6-diaminopurine
<220> FEATURE:
```

<221> NAME/KEY: misc_feature
<222> LOCATION: (29)..(29)
<223> OTHER INFORMATION: n is A or 2,6-diaminopurine
<220> FEATURE:
<221> NAME/KEY: misc_feature
<222> LOCATION: (30)..(30)
<223> OTHER INFORMATION: n is U or 5-methyluracil

<400> SEQUENCE: 61
ngnnnngnnn ngnnnngnnn ngnnnngnnn                    30

<210> SEQ ID NO 62
<211> LENGTH: 35
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is A or 2,6-diaminopurine
<220> FEATURE:
<221> NAME/KEY: misc_feature
<222> LOCATION: (3)..(3)
<223> OTHER INFORMATION: n is A or 2,6-diaminopurine
<220> FEATURE:
<221> NAME/KEY: misc_feature
<222> LOCATION: (4)..(4)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is U or 5-methyluracil
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (8)..(8)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is A or 2,6-diaminopurine
<220> FEATURE:
<221> NAME/KEY: misc_feature
<222> LOCATION: (10)..(10)
<223> OTHER INFORMATION: n is U or 5-methyluracil
<220> FEATURE:
<221> NAME/KEY: misc_feature
<222> LOCATION: (11)..(11)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is A or 2,6-diaminopurine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (15)..(15)
<223> OTHER INFORMATION: n is U or 5-methyluracil
<220> FEATURE:
<221> NAME/KEY: misc_feature
<222> LOCATION: (16)..(16)
<223> OTHER INFORMATION: n is A or 2,6-diaminopurine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (19)..(19)
<223> OTHER INFORMATION: n is A or 2,6-diaminopurine

```
<220> FEATURE:
<221> NAME/KEY: misc_feature
<222> LOCATION: (20)..(20)
<223> OTHER INFORMATION: n is U or 5-methyluracil
<220> FEATURE:
<221> NAME/KEY: misc_feature
<222> LOCATION: (21)..(21)
<223> OTHER INFORMATION: n is A or 2,6-diaminopurine
<220> FEATURE:
<221> NAME/KEY: misc_feature
<222> LOCATION: (23)..(23)
<223> OTHER INFORMATION: n is A or 2,6-diaminopurine
<220> FEATURE:
<221> NAME/KEY: misc_feature
<222> LOCATION: (24)..(24)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is U or 5-methyluracil
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (28)..(28)
<223> OTHER INFORMATION: n is A or 2,6-diaminopurine
<220> FEATURE:
<221> NAME/KEY: misc_feature
<222> LOCATION: (29)..(29)
<223> OTHER INFORMATION: n is A or 2,6-diaminopurine
<220> FEATURE:
<221> NAME/KEY: misc_feature
<222> LOCATION: (30)..(30)
<223> OTHER INFORMATION: n is U or 5-methyluracil
<220> FEATURE:
<221> NAME/KEY: misc_feature
<222> LOCATION: (31)..(31)
<223> OTHER INFORMATION: n is A or 2,6-diaminopurine
<220> FEATURE:
<221> NAME/KEY: misc_feature
<222> LOCATION: (33)..(33)
<223> OTHER INFORMATION: n is A or 2,6-diaminopurine
<220> FEATURE:
<221> NAME/KEY: misc_feature
<222> LOCATION: (34)..(34)
<223> OTHER INFORMATION: n is A or 2,6-diaminopurine
<220> FEATURE:
<221> NAME/KEY: misc_feature
<222> LOCATION: (35)..(35)
<223> OTHER INFORMATION: n is U or 5-methyluracil

<400> SEQUENCE: 62
ngnnnngnnn ngnnnngnnn ngnnnngnnn ngnnn                                    35

<210> SEQ ID NO 63
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
```

```
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine

<400> SEQUENCE: 63
nnggnnggnn gg                                                              12

<210> SEQ ID NO 64
<211> LENGTH: 16
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine

<400> SEQUENCE: 64
nnggnnggnn ggnngg                                                          16

<210> SEQ ID NO 65
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
```

```
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine

<400> SEQUENCE: 65
nnggnnggnn ggnnggnngg                                           20

<210> SEQ ID NO 66
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
```

```
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine

<400> SEQUENCE: 66
nnggnnggnn ggnnggnngg nngg                                              24

<210> SEQ ID NO 67
<211> LENGTH: 28
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is A or 2,6-diaminopurine

<400> SEQUENCE: 67
nnggnnggnn ggnnggnngg nnggnngg                                          28
```

```
<210> SEQ ID NO 68
<211> LENGTH: 32
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is A or 2,6-diaminopurine

<400> SEQUENCE: 68
nnggnnggnn ggnnggnngg nnggnnggnn gg                                  32

<210> SEQ ID NO 69
```

```
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is C or 5-methylcytosine
<220> FEATURE:
<221> NAME/KEY: misc_feature
<222> LOCATION: (2)..(2)
<223> OTHER INFORMATION: n is A or 2,6-diaminopurine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is A or 2,6-diaminopurine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is A or 2,6-diaminopurine
<220> FEATURE:
<221> NAME/KEY: misc_feature
<222> LOCATION: (13)..(13)
<223> OTHER INFORMATION: n is C or 5-methylcytosine
<220> FEATURE:
<221> NAME/KEY: misc_feature
<222> LOCATION: (14)..(14)
<223> OTHER INFORMATION: n is A or 2,6-diaminopurine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is A or 2,6-diaminopurine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is A or 2,6-diaminopurine
<220> FEATURE:
<221> NAME/KEY: misc_feature
<222> LOCATION: (25)..(25)
<223> OTHER INFORMATION: n is C or 5-methylcytosine
<220> FEATURE:
<221> NAME/KEY: misc_feature
<222> LOCATION: (26)..(26)
<223> OTHER INFORMATION: n is A or 2,6-diaminopurine
<220> FEATURE:
<221> NAME/KEY: misc_feature
<222> LOCATION: (29)..(29)
<223> OTHER INFORMATION: n is C or 5-methylcytosine
<220> FEATURE:
<221> NAME/KEY: misc_feature
<222> LOCATION: (30)..(30)
<223> OTHER INFORMATION: n is A or 2,6-diaminopurine
<220> FEATURE:
<221> NAME/KEY: misc_feature
<222> LOCATION: (33)..(33)
<223> OTHER INFORMATION: n is C or 5-methylcytosine
<220> FEATURE:
<221> NAME/KEY: misc_feature
<222> LOCATION: (34)..(34)
<223> OTHER INFORMATION: n is A or 2,6-diaminopurine

<400> SEQUENCE: 69
```
nnggnnggnn ggnnggnngg nnggnnggnn ggnngg 36

<210> SEQ ID NO 70
<211> LENGTH: 23
<212> TYPE: DNA
<213> ORGANISM: Artificial
<220> FEATURE:
<223> OTHER INFORMATION: Primer

<400> SEQUENCE: 70
atggcgaccc tggaaaagct gat 23

<210> SEQ ID NO 71
<211> LENGTH: 17
<212> TYPE: DNA
<213> ORGANISM: Artificial
<220> FEATURE:
<223> OTHER INFORMATION: Primer

<400> SEQUENCE: 71
tgaggcagca gcggctg 17

<210> SEQ ID NO 72
<211> LENGTH: 20
<212> TYPE: DNA
<213> ORGANISM: Artificial
<220> FEATURE:
<223> OTHER INFORMATION: Primer

<400> SEQUENCE: 72
ggacttcgag caagagatgg 20

<210> SEQ ID NO 73
<211> LENGTH: 20
<212> TYPE: DNA
<213> ORGANISM: Artificial
<220> FEATURE:
<223> OTHER INFORMATION: Primer

<400> SEQUENCE: 73
agcactgtgt tggcgtacag 20

<210> SEQ ID NO 74
<211> LENGTH: 18
<212> TYPE: DNA
<213> ORGANISM: Artificial
<220> FEATURE:
<223> OTHER INFORMATION: Primer

<400> SEQUENCE: 74
cgccgcctcc tcagcttc 18

<210> SEQ ID NO 75
<211> LENGTH: 24
<212> TYPE: DNA
<213> ORGANISM: Artificial
<220> FEATURE:
<223> OTHER INFORMATION: Primer

<400> SEQUENCE: 75
gagagttcct tctttggtcg gtgc 24

<210> SEQ ID NO 76
<211> LENGTH: 23
<212> TYPE: DNA

```
<213> ORGANISM: Artificial
<220> FEATURE:
<223> OTHER INFORMATION: Primer

<400> SEQUENCE: 76
tgggaaacag ataaaactcc aga                                             23

<210> SEQ ID NO 77
<211> LENGTH: 26
<212> TYPE: DNA
<213> ORGANISM: Artificial
<220> FEATURE:
<223> OTHER INFORMATION: Primer

<400> SEQUENCE: 77
aatatgacct tgtgatagaa cgaaag                                          26

<210> SEQ ID NO 78
<211> LENGTH: 20
<212> TYPE: DNA
<213> ORGANISM: Artificial
<220> FEATURE:
<223> OTHER INFORMATION: Primer

<400> SEQUENCE: 78
aaatgagctg gtgcagaagg                                                 20

<210> SEQ ID NO 79
<211> LENGTH: 19
<212> TYPE: DNA
<213> ORGANISM: Artificial
<220> FEATURE:
<223> OTHER INFORMATION: Primer

<400> SEQUENCE: 79
ggctgccatg tcatcgtat                                                  19

<210> SEQ ID NO 80
<211> LENGTH: 13481
<212> TYPE: DNA
<213> ORGANISM: Homo sapiens

<400> SEQUENCE: 80
gctgccggga cgggtccaag atggacggcc gctcaggttc tgcttttacc tgcggcccag     60
agccccattc attgccccgg tgctgagcgg cgccgcgagt cggcccgagg cctccgggga    120
ctgccgtgcc gggcgggaga ccgccatggc gaccctggaa aagctgatga aggccttcga    180
gtccctcaag tccttccagc agcagcagca gcagcagcag cagcagcagc agcagcagca    240
gcagcagcag cagcagcagc aacagccgcc accgccgccg ccgccgccgc cgcctcctca    300
gcttcctcag ccgccgccgc aggcacagcc gctgctgcct cagccgcagc cgccccgcc    360 gccgccccg ccgccacccg gcccggctgt ggctgaggag ccgctgcacc gaccaaagaa    420
agaactttca gctaccaaga agaccgtgt gaatcattgt ctgacaatat gtgaaaacat    480
agtggcacag tctgtcagaa attctccaga atttcagaaa cttctgggca tcgctatgga    540 acttttctg ctgtgcagtg atgacgcaga gtcagatgtc aggatggtgg ctgacgaatg    600
cctcaacaaa gttatcaaag ctttgatgga ttctaatctt ccaaggttac agctcgagct    660
ctataaggaa attaaaaaga atggtgcccc tcggagtttg cgtgctgccc tgtggaggtt    720
tgctgagctg gctcacctgg ttcggcctca gaaatgcagg ccttacctgg tgaaccttct    780
gccgtgcctg actcgaacaa gcaagagacc cgaagaatca gtccaggaga ccttggctgc    840
```

```
agctgttccc aaaattatgg cttcttttgg caattttgca aatgacaatg aaattaaggt    900
tttgttaaag gccttcatag cgaacctgaa gtcaagctcc cccaccattc ggcggacagc    960
ggctggatca gcagtgagca tctgccagca ctcaagaagg acacaatatt tctatagttg   1020
gctactaaat gtgctcttag gcttactcgt tcctgtcgag gatgaacact ccactctgct   1080
gattcttggc gtgctgctca ccctgaggta tttggtgccc ttgctgcagc agcaggtcaa   1140
ggacacaagc ctgaaaggca gcttcggagt gacaaggaaa gaaatggaag tctctccttc   1200
tgcagagcag cttgtccagg tttatgaact gacgttacat catacacagc accaagacca   1260
caatgttgtg accggagccc tggagctgtt gcagcagctc ttcagaacgc tccacccga   1320
gcttctgcaa accctgaccg cagtcggggg cattgggcag ctcaccgctg ctaaggagga   1380
gtctggtggc cgaagccgta gtgggagtat tgtggaactt atagctggag ggggttcctc   1440
atgcagccct gtccttcaa gaaaacaaaa aggcaaagtg ctcttaggag aagaagaagc   1500
cttggaggat gactctgaat cgagatcgga tgtcagcagc tctgccttaa cagcctcagt   1560
gaaggatgag atcagtggag agctggctgc ttcttcaggg gtttccactc cagggtcagc   1620
aggtcatgac atcatcacag aacagccacg gtcacagcac acactgcagg cggactcagt   1680
ggatctggcc agctgtgact tgacaagctc tgccactgat ggggatgagg aggatatctt   1740
gagccacagc tccagccagg tcagcgccgt cccatctgac cctgccatgg acctgaatga   1800
tgggacccag gcctcgtcgc ccatcagcga cagctcccag accaccaccg aagggcctga   1860
ttcagctgtt accccttcag acagttctga aattgtgtta gacggtaccg acaaccagta   1920
tttgggcctg cagattggac agccccagga tgaagatgag gaagccacag gtattcttcc   1980
tgatgaagcc tcggaggcct tcaggaactc ttccatggcc cttcaacagg cacatttatt   2040
gaaaaacatg agtcactgca ggcagccttc tgacagcagt gttgataaat ttgtgttgag   2100
agatgaagct actgaaccgg gtgatcaaga aaacaagcct tgccgcatca aggtgacat   2160
tggacagtcc actgatgatg actctgcacc tcttgtccat tgtgtccgcc ttttatctgc   2220
ttcgttttg ctaacagggg gaaaaatgt gctggttccg gacagggatg tgagggtcag   2280
cgtgaaggcc ctggccctca gctgtgtggg agcagctgtg gccctccacc cggaatcttt   2340
cttcagcaaa ctctataaag ttcctcttga caccacggaa taccctgagg aacagtatgt   2400
ctcagacatc ttgaactaca tcgatcatgg agacccacag gttcgaggag ccactgccat   2460
tctctgtggg accctcatct gctccatcct cagcaggtcc cgcttccacg tgggagattg   2520
gatgggcacc attagaaccc tcacaggaaa tacattttct ttggcggatt gcattccttt   2580
gctgcggaaa acactgaagg atgagtcttc tgttacttgc aagttagctt gtacagctgt   2640
gaggaactgt gtcatgagtc tctgcagcag cagctacagt gagttaggac tgcagctgat   2700
catcgatgtg ctgactctga ggaacagttc ctattggctg gtgaggacag agcttctgga   2760
aacccttgca gagattgact tcaggctggt gagctttttg gaggcaaaag cagaaaactt   2820
acacagaggg gctcatcatt atacagggct tttaaaactg caagaacgag tgctcaataa   2880
tgttgtcatc catttgcttg gagatgaaga ccccagggtg cgacatgttg ccgcagcatc   2940
actaattagg cttgtcccaa agctgttta taaatgtgac caaggacaag ctgatccagt   3000
agtggccgtg gcaagagatc aaagcagtgt ttacctgaaa cttctcatgc atgagacgca   3060
gcctccatct catttctccg tcagcacaat aaccagaata tatagaggct ataacctact   3120
accaagcata acagacgtca ctatggaaaa taacctttca agagttattg cagcagtttc   3180
```

```
tcatgaacta atcacatcaa ccaccagagc actcacattt ggatgctgtg aagctttgtg    3240
tcttctttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
ttctctaaca aaccccccctt ctctaagtcc catccgacga aggggaagg agaaagaacc    3720
aggagaacaa gcatctgtac cgttgagtcc caagaaaggc agtgaggcca gtgcagcttc    3780
tagacaatct gatacctcag gtcctgttac aacaagtaaa tcctcatcac tggggagttt    3840
ctatcatctt ccttcatacc tcaaactgca tgatgtcctg aaagctacac acgctaacta    3900
caaggtcacg ctggatcttc agaacagcac ggaaaagttt ggagggtttc tccgctcagc    3960
cttggatgtt cttctcaga tactagagct ggccacactg caggacattg ggaagtgtgt    4020
tgaagagatc ctaggatacc tgaaatcctg ctttagtcga gaaccaatga tggcaactgt    4080
ttgtgttcaa caattgttga agactctctt tggcacaaac ttggcctccc agtttgatgg    4140
cttatcttcc aaccccagca agtcacaagg ccgagcacag cgccttggct cctccagtgt    4200
gaggccaggc ttgtaccact actgcttcat ggccccgtac acccacttca cccaggccct    4260
cgctgacgcc agcctgagga acatggtgca ggcggagcag gagaacgaca cctcgggatg    4320
gtttgatgtc ctccagaaag tgtctaccca gttgaagaca aacctcacga gtgtcacaaa    4380
gaaccgtgca gataagaatg ctattcataa tcacattcgt ttgtttgaac ctcttgttat    4440
aaaagcttta aaacagtaca cgactacaac atgtgtgcag ttacagaagc aggttttaga    4500
tttgctggcg cagctggttc agttacgggt taattactgt cttctggatt cagatcaggt    4560
gtttattggc tttgtattga aacagtttga atacattgaa gtgggccagt tcagggaatc    4620
agaggcaatc attccaaaca tcttttttctt cttggtatta ctatcttatg aacgctatca    4680
ttcaaaacag atcattggaa ttcctaaaat cattcagctc tgtgatggca tcatggccag    4740
tgaaggaag gctgtgacac atgccatacc ggctctgcag cccatagtcc acgacctctt    4800
tgtattaaga ggaacaaata aagctgatgc aggaaaagag cttgaaaccc aaaaagaggt    4860
ggtggtgtca atgttactga gactcatcca gtaccatcag gtgttggaga tgttcattct    4920
tgtcctgcag cagtgccaca aggagaatga agacaagtgg aagcgactgt ctcgacagat    4980
agctgacatc atcctcccaa tgttagccaa acagcagatg cacattgact ctcatgaagc    5040
ccttggagtg ttaaatacat tatttgagat tttggcccct tcctccctcc gtccggtaga    5100
catgctttta cggagtatgt tcgtcactcc aaacacaatg gcgtccgtga gcactgttca    5160
actgtggata tcgggaattc tggccatttt gagggttctg atttcccagt caactgaaga    5220
tattgttctt tctcgtattc aggagctctc cttctctccg tatttaatct cctgtacagt    5280
aattaatagg ttaagagatg gggacagtac ttcaacgcta aagaacacag gtgaagggaa    5340
acaaataaag aatttgccag aagaaacatt ttcaaggttt ctattacaac tggttggtat    5400
tcttttagaa gacattgtta caaaacagct gaaggtggaa atgagtgagc agcaacatac    5460
tttctattgc caggaactag gcacactgct aatgtgtctg atccacatct tcaagtctgg    5520
aatgttccgg agaatcacag cagctgccac taggctgttc cgcagtgatg gctgtggcgg    5580
```

```
cagtttctac accctggaca gcttgaactt gcgggctcgt tccatgatca ccacccaccc    5640
ggccctggtg ctgctctggt gtcagatact gctgcttgtc aaccacaccg actaccgctg    5700
gtgggcagaa gtgcagcaga ccccgaaaag acacagtctg tccagcacaa agttacttag    5760
tccccagatg tctggagaag aggaggattc tgacttggca gccaaacttg gaatgtgcaa    5820
tagagaaata gtacgaagag gggctctcat tctcttctgt gattatgtct gtcagaacct    5880
ccatgactcc gagcacttaa cgtggctcat tgtaaatcac attcaagatc tgatcagcct    5940
ttcccacgag cctccagtac aggacttcat cagtgccgtt catcggaact ctgctgccag    6000
cggcctgttc atccaggcaa ttcagtctcg ttgtgaaaac cttcaactc caaccatgct     6060 gaagaaaact cttcagtgct tggaggggat ccatctcagc cagtcgggag ctgtgctcac    6120
gctgtatgtg gacaggcttc tgtgcacccc tttccgtgtg ctggctcgca tggtcgacat    6180
ccttgcttgt cgccgggtag aaatgcttct ggctgcaaat ttacagagca gcatggccca    6240
gttgccaatg aagaactca acagaatcca ggaataccct cagagcagcg ggctcgctca     6300
gagacaccaa aggctctatt ccctgctgga caggtttcgt ctctccacca tgcaagactc    6360
acttagtccc tctcctccag tctcttccca ccgctggac ggggatgggc acgtgtcact     6420
ggaaacagtg agtccggaca aagactggta cgttcatctt gtcaaatccc agtgttggac    6480
caggtcagat tctgcactgc tggaaggtgc agagctggtg aatcggattc ctgctgaaga    6540
tatgaatgcc ttcatgatga actcggagtt caacctaagc ctgctagctc catgcttaag    6600
cctagggatg agtgaaattt ctggtggcca aagagtgcc cttttgaag cagcccgtga      6660 ggtgactctg gcccgtgtga gcggcaccgt gcagcagctc cctgctgtcc atcatgtctt    6720
ccagcccgag ctgcctgcag agccggcggc ctactggagc aagttgaatg atctgtttgg    6780
ggatgctgca ctgtatcagt ccctgcccac tctggcccgg gccctggcac agtacctggt    6840
ggtggtctcc aaactgccca gtcatttgca ccttcctcct gagaaagaga aggacattgt    6900
gaaattcgtg gtggcaaccc ttgaggccct gtcctggcat ttgatccatg agcagatccc    6960
gctgagtctg gatctccagg cagggctgga ctgctgctgc ctggccctgc agctgcctgg    7020
cctctggagc gtggtctcct ccacagagtt tgtgacccac gctgctccc tcatctactg     7080 tgtgcacttc atcctggagg ccgttgcagt gcagcctgga gagcagcttc ttagtccaga    7140
aagaaggaca ataccccaa aagccatcag cgaggaggag gaggaagtag atccaaacac     7200
acagaatcct aagtatatca ctgcagcctg tgagatggtg gcagaaatgg tggagtctct    7260
gcagtcggtg ttggccttgg gtcataaaag gaatagcggc gtgccggcgt ttctcacgcc    7320
attgctaagg aacatcatca tcagcctggc ccgcctgccc cttgtcaaca gctacacacg    7380
tgtgccccca ctggtgtgga gcttggatg gtcacccaaa ccgggagggg attttggcac    7440
agcattccct gagatccccg tggagttcct ccaggaaaag gaagtcttta aggagttcat    7500
ctaccgcatc aacacactag gctggaccag tcgtactcag tttgaagaaa cttgggccac    7560
cctccttggt gtcctggtga cgcagcccct cgtgatggag caggaggaga gcccaccaga    7620
agaagacaca gagaggaccc agatcaacgt cctggccgtg caggccatca cctcactggt    7680
gctcagtgca atgactgtgc ctgtggccgg caacccagct gtaagctgct ggagcagca    7740 gccccggaac aagcctctga aagctctcga caccaggttt gggaggaagc tgagcattat    7800
cagagggatt gtggagcaag agattcaagc aatggtttca aagagagaga atattgccac    7860
ccatcattta tatcaggcat gggatcctgt cccttctctg tctccggcta ctacaggtgc    7920
```

```
cctcatcagc cacgagaagc tgctgctaca gatcaacccc gagcgggagc tggggagcat    7980
gagctacaaa ctcggccagg tgtccataca ctccgtgtgg ctggggaaca gcatcacacc    8040
cctgagggag gaggaatggg acgaggaaga ggaggaggag gccgacgccc ctgcaccttc    8100
gtcaccaccc acgtctccag tcaactccag gaaacaccgg gctggagttg acatccactc    8160
ctgttcgcag tttttgcttg agttgtacag ccgctggatc ctgccgtcca gctcagccag    8220
gaggaccccg gccatcctga tcagtgaggt ggtcagatcc cttctagtgg tctcagactt    8280
gttcaccgag cgcaaccagt ttgagctgat gtatgtgacg ctgacagaac tgcgaagggt    8340
gcacccttca gaagacgaga tcctcgctca gtacctggtg cctgccacct gcaaggcagc    8400
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
ggagtgcgac ctgctggacg acactgccaa gcagctcatc ccggtcatca gcgactatct    8580
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc    9000 agtgattgtt gctatggagc gggtatctgt tctttttgat aggatcagga aaggcttttcc    9060 ttgtgaagcc agagtggtgg ccaggatcct gccccagttt ctagacgact tcttcccacc    9120
ccaggacatc atgaacaaag tcatcggaga gtttctgtcc aaccagcagc catacccca    9180 gttcatggcc accgtggtgt ataaggtgtt tcagactctg cacagcaccg gcagtcgtc    9240 catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accgctgct    9540 gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat gggcttccgc acatgccgcg ggcggccagg caacgtgcgt    9720
gtctctgcca tgtggcagaa gtgctctttg tggcagtggc caggcaggga gtgtctgcag    9780
tcctggtggg gctgagcctg aggccttcca gaaagcagga gcagctgtgc tgcacccat    9840 gtgggtgacc aggtccttc tcctgatagt cacctgctgg ttgttgccag gttgcagctg    9900
ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg    10020
ggtgtgcatg ccacgccccg tgtctggatg cacagatgcc atggcctgtg ctgggccagt    10080
ggctgggggt gctagacacc cggcaccatt ctcccttctc tcttttcttc tcaggattta    10140
aaatttaatt atatcagtaa agagattaat tttaacgtaa ctctttctat gcccgtgtaa    10200
agtatgtgaa tcgcaaggcc tgtgctgcat gcgacagcgt ccggggtggt ggacagggcc    10260
cccggccacg ctccctctcc tgtagccact ggcatagccc tcctgagcac ccgctgacat    10320
```

```
ttccgttgta catgttcctg tttatgcatt cacaaggtga ctgggatgta gagaggcgtt    10380
agtgggcagg tggccacagc aggactgagg acaggccccc attatcctag ggtgcgctc    10440 acctgcagcc cctcctcctc gggcacagac gactgtcgtt ctccaccac cagtcaggga    10500 cagcagcctc cctgtcactc agctgagaag gccagccctc cctggctgtg agcagcctcc    10560
actgtgtcca gagacatggg cctcccactc ctgttccttg ctagccctgg ggtggcgtct    10620
gcctaggagc tggctggcag gtgttgggac ctgctgctcc atggatgcat gccctaagag    10680
tgtcactgag ctgtgttttg tctgagcctc tctcggtcaa cagcaaagct tggtgtcttg    10740
gcactgttag tgacagagcc cagcatccct tctgccccg ttccagctga catcttgcac    10800
ggtgacccct tttagtcagg agagtgcaga tctgtgctca tcggagactg ccccacggcc    10860
ctgtcagagc cgccactcct atccccaggc caggtccctg accagcctc ctgtttgcag    10920 gcccagagga gccaagtcat taaaatggaa gtggattctg gatggccggg ctgctgctga    10980
tgtaggagct ggatttggga gctctgcttg ccgactggct gtgagacgag gcaggggctc    11040
tgcttcctca gccctagagg cgagccaggc aaggttggcg actgtcatgt ggcttggttt    11100
ggtcatgccc gtcgatgttt tgggtattga atgtggtaag tggaggaaat gttggaactc    11160
tgtgcaggtg ctgccttgag accccaagc ttccacctgt ccctctccta tgtggcagct    11220
ggggagcagc tgagatgtgg acttgtatgc tgcccacata cgtgaggggg agctgaaagg    11280
gagcccctcc tctgagcagc ctctgccagg cctgtatgag gcttttccca ccagctccca    11340
acagaggcct cccccagcca ggaccacctc gtcctcgtgg cggggcagca ggagcggtag    11400
aaaggggtcc gatgtttgag gaggcccta agggaagcta ctgaattata acacgtaaga    11460
aaatcaccat tccgtattgg ttgggggctc ctgtttctca tcctagcttt ttcctggaaa    11520
gcccgctaga aggtttggga acgaggggaa agttctcaga actgttggct gctccccacc    11580
cgcctcccgc ctcccccgca ggttatgtca gcagctctga gacagcagta tcacaggcca    11640
gatgttgttc ctggctagat gtttacattt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa caccccgctc tggcagtagg    11820
tgtcccccac ccccaaagac ctgcctgtgt gctccggaga tgaatatgag ctcattagta    11880
aaaatgactt cacccacgca tatacataaa gtatccatgc atgtgcatat agacacatct    11940
ataattttac acacacacct ctcaagacgg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag gatcccactg    12120
gcgaagatgg tctccatatc agctctctgc agaaggagg aagactttat catgttccta    12180
aaaatctgtg gcaagcaccc atcgtattat ccaaattttg ttgcaaatgt gattaatttg    12240
gttgtcaagt tttgggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaaccccct ccagacaccc agaatgtagc atctgagaag    12540
gccctgtgcc ctaaaggaca cccctcgccc ccatcttcat ggaggggtc atttcagagc    12600 cctcggagcc aatgaacagc tcctcctctt ggagctgaga tgagcccac gtggagctcg    12660
```

| | |
|---|---:|
| ggacggatag tagacagcaa taactcggtg tgtggccgcc tggcaggtgg aacttcctcc | 12720 |
| cgttgcgggg tggagtgagg ttagttctgt gtgtctggtg ggtggagtca ggcttctctt | 12780 |
| gctacctgtg agcatccttc ccagcagaca tcctcatcgg gctttgtccc tcccccgctt | 12840 |
| cctccctctg cggggaggac ccgggaccac agctgctggc cagggtagac ttggagctgt | 12900 |
| cctccagagg ggtcacgtgt aggagtgaga agaaggaaga tcttgagagc tgctgaggga | 12960 |
| ccttggagag ctcaggatgg ctcagacgag gacactcgct tgccgggcct gggcctcctg | 13020 |
| ggaaggaggg agctgctcag aatgccgcat gacaactgaa ggcaacctgg aaggttcagg | 13080 |
| ggccgctctt cccccatgtg cctgtcacgc tctggtgcag tcaaaggaac gccttcccct | 13140 |
| cagttgtttc taagagcaga gtctcccgct gcaatctggg tggtaactgc cagccttgga | 13200 |
| ggatcgtggc caacgtggac ctgcctacga agggtgggct ctgacccaag tggggcctcc | 13260 |
| ttgtccaggt ctcactgctt tgcaccgtgg tcagaggggac tgtcagctga gcttgagctc | 13320 |
| ccctggagcc agcagggctg tgatgggcga gtcccggagc cccacccaga cctgaatgct | 13380 |
| tctgagagca agggaagga ctgacgagag atgtatattt aatttttta ctgctgcaaa | 13440 |
| cattgtacat ccaaattaaa ggaaaaaaat ggaaaccatc a | 13481 |

<210> SEQ ID NO 81
<211> LENGTH: 10636
<212> TYPE: DNA
<213> ORGANISM: Homo sapiens

<400> SEQUENCE: 81

| | |
|---|---:|
| gaggagagag cagagtatac cgcagacatc atttctacta cagtggcgga gccgtacagg | 60 |
| acctgtttca ctgcaggggg atccaaaaca agccccgtgg agcagcagcc agagcaacag | 120 |
| cagccgcaag acattgtttc tctccctctg ccccccccttc cccacgcaac cccagatcca | 180 |
| tttacacttt acagttttac ctcacaaaaa ctactacaag caccaagctc cctgatggaa | 240 |
| aggagcatcg tgcatcaagt caccagggtg gtccattcaa gctgcagatt tgtttgtcat | 300 |
| ccttgtacag caatctcctc ctccactgcc actacaggga agtgcatcac atgtcagcat | 360 |
| actggagcat agtgaaagag tctatttga agcttcaaac ttagtgctgc tgcagaccag | 420 |
| gaacaagaga gaaagagtgg atttcagcct gcacggatgg tcttgaaaca caaatggttt | 480 |
| ttggtctagg cgttttacac tgagattctc cactgccacc ctttctactc aagcaaaatc | 540 |
| ttcgtgaaaa gatctgctgc aaggaactga tagcttatgg ttctccattg tgatgaaagc | 600 |
| acatggtaca gttttccaaa gaaattagac catttttcttc gtgagaaaga aatcgacgtg | 660 |
| ctgttttcat agggtatttc tcacttctct gtgaaaggaa gaaagaacac gcctgagccc | 720 |
| aagagccctc aggagccctc cagagcctgt gggaagtctc catggtgaag tataggctga | 780 |
| ggctacctgt gaacagtacg cagtgaatgt tcatccagag ctgctgttgg cggattgtac | 840 |
| ccacggggag atgattcctc atgaagagcc tggatcccct acagaaatca aatgtgactt | 900 |
| tccgtttatc agactaaaat cagagccatc cagacagtga acagtcacc gtggagggg | 960 |
| gacggcgaaa aatgaaatcc aaccaagagc ggagcaacga atgcctgcct cccaagaagc | 1020 |
| gcgagatccc cgccaccagc cggtcctccg aggagaaggc ccctaccctg cccagcgaca | 1080 |
| accaccgggt ggagggcaca gcatggctcc cgggcaaccc tggtggccgg ggccacgggg | 1140 |
| gcgggaggca tgggcgggca gggacctcgg tggagcttgg tttacaacag gaataggtt | 1200 |
| tacacaaagc attgtccaca gggctggact actccccgcc cagcgctccc aggtctgtcc | 1260 |
| ccgtggccac cacgctgcct gccgcgtacg ccaccccgca gccagggacc ccggtgtccc | 1320 |

```
ccgtgcagta cgctcacctg ccgcacacct tccagttcat tgggtcctcc caatacagtg    1380
gaacctatgc cagcttcatc ccatcacagc tgatccccc aaccgccaac cccgtcacca     1440
gtgcagtggc ctcggccgca ggggccacca ctccatccca gcgctcccag ctggaggcct    1500
attccactct gctggccaac atgggcagtc tgagccagac gccgggacac aaggctgagc    1560
agcagcagca gcagcagcag cagcagcagc agcagcatca gcatcagcag cagcagcagc    1620
agcagcagca gcagcagcag cagcagcacc tcagcagggc tccggggctc atcacccggg    1680
ggtccccccc accagcccag cagaaccagt acgtccacat ttccagttct ccgcagaaca    1740
ccggccgcac cgcctctcct ccggccatcc ccgtccacct ccaccccac cagacgatga     1800
tcccacacac gctcaccctg ggccccccct cccaggtcgt catgcaatac gccgactccg    1860
gcagccactt tgtccctcgg gaggccacca agaaagctga gagcagccgg ctgcagcagg    1920
ccatccaggc caaggaggtc ctgaacggtg agatggagaa gagccggcgg tacggggccc    1980
cgtcctcagc cgacctgggc ctgggcaagg caggcggcaa gtcggttcct cacccgtacg    2040
agtccaggca cgtggtggtc cacccgagcc cctcagacta cagcagtcgt gatccttcgg    2100
gggtccgggc ctctgtgatg gtcctgccca acagcaacac gcccgcagct gacctggagg    2160
tgcaacaggc cactcatcgt gaagcctccc cttctaccct caacgacaaa gtggcctgc    2220
atttagggaa gcctggccac cggtcctacg cgctctcacc ccacacggtc attcagacca    2280
cacacagtgc ttcagagcca ctcccggtgg gactgccagc cacggccttc tacgcaggga    2340
ctcaaccccc tgtcatcggc tacctgagcg gccagcagca agcaatcacc tacgccggca    2400
gcctgcccca gcacctggtg atccccggca cacagcccct gctcatcccg gtcggcagca    2460
ctgacatgga agcgtcgggg gcagcccgg ccatagtcac gtcatccccc cagtttgctg     2520
cagtgcctca cacgttcgtc accaccgccc ttcccaagag cgagaacttc aaccctgagg    2580
ccctggtcac ccaggccgcc tacccagcca tggtgcaggc ccagatccac ctgcctgtgg    2640
tgcagtccgt ggcctccccg gcggcggctc ccctacgct gcctccctac ttcatgaaag     2700
gctccatcat ccagttggcc aacgggagc taaagaaggt ggaagactta aaaacagaag    2760
atttcatcca gagtgcagag ataagcaacg acctgaagat cgactccagc accgtagaga    2820
ggattgaaga cagccatagc ccgggcgtgg ccgtgataca gttcgccgtc ggggagcacc    2880
gagcccaggt cagcgttgaa gttttggtag agtatccttt ttttgtgttt ggacagggct    2940
ggtcatcctg ctgtccggag agaaccagcc agctctttga tttgccgtgt tccaaactct    3000
cagttgggga tgtctgcatc tcgcttaccc tcaagaacct gaagaacggc tctgttaaaa    3060
agggccagcc cgtggatccc gccagcgtcc tgctgaagca ctcaaaggcc gacggcctgg    3120
cgggcagcag acacaggtat gccgagcagg aaaacggaat caaccagggg agtgcccaga    3180
tgctctctga gaatggcgaa ctgaagtttc cagagaaaat gggattgcct gcagcgccct    3240
tcctcaccaa aatagaaccc agcaagcccg cggcaacgag gaagaggagg tggtcggcgc    3300
cagagagccg caaactggag aagtcagaag acgaaccacc tttgactctt cctaagcctt    3360
ctctaattcc tcaggaggtt aagatttgca ttgaaggccg gtctaatgta ggcaagtaga    3420
ggcagcgtgg gggaaaggaa acgtggctct cccttatcat ttgtatccag attactgtac    3480
tgtaggctaa aataacacag tatttacatg ttatcttctt aattttaggt ttctgttcta    3540
accttgtcat tagagttaca gcaggtgtgt cgcaggagac tggtgcatat gcttttttcca   3600
cgagtgtctg tcagtgagcg ggcgggagga agggcacagc aggagcggtc agggctccag    3660
```

```
gcatccccgg ggaagaaagg aacggggctt cacagtgcct gccttctcta gcggcacaga    3720
agcagccggg ggcgctgact cccgctagtg tcaggagaaa agtcccgtgg gaagggtcct    3780
gcaggggtgc agggttgcac gcatgtgggg gtgcacaggc gctgtggcgg cgagtgaggg    3840
tctctttttc tctgcctccc tctgcctcac tctcttgcta tcggcatggg ccgggggggt    3900
tcagagcagt gtcctcctgg ggttcccacg tgcaaaatca acatcaggaa cccagcttca    3960
gggcatcgcg gagacgcgtc agatggcaga tttggaaagt taaccattta aaagaacatt    4020
tttctctcca acatatttta caataaaagc aacttttaat tgtatagata tatatttccc    4080 cctatgggc ctgactgcac tgatatatat tttttttaaa gagcaactgc cacatgcggg    4140
atttcatttc tgcttttac tagtgcagcg atgtcaccag ggtgttgtgg tggacaggga    4200
agcccctgct gtcatggccc cacatggggt aagggggggtt gggggtgggg gagagggaga    4260
gagcgaacac ccacgctggt ttctgtgcag tgttaggaaa accaatcagg ttattgcatt    4320
gacttcactc ccaagaggta gatgcaaact gcccttcagt gagagcaaca gaagctcttc    4380
acgttgagtt tgcgaaatct ttttgtcttt gaactctagt actgtttata gttcatgact    4440
atggacaact cgggtgccac tttttttttt tttcagattc cagtgtgaca tgaggaatta    4500
gattttgaag atgagcatat attactatct ttaagcattt aaaaatactg ttcacacttt    4560
attaccaagc atcttggtct ctcattcaac aagtactgta tctcacttta aactctttgg    4620
ggaaaaaaca aaaacaaaaa aaactaagtt gctttctttt tttcaacact gtaactacat    4680
ttcagctctg cagaattgct gaagagcaag atattgaaag tttcaatgtg gtttaaaggg    4740
atgaatgtga attatgaact agtatgtgac aataaatgac caccaagtac tacctgacgg    4800
gaggcacttt tcactttgat gtctgagaat cagttcaagg catatgcaga gttggcagag    4860
aaactgagaa aaaagggatg gagaagagaa tactcatttt tgtccagtgt ttttcttttt    4920
aagatgaact tttaaagaac cttgcgattt gcacatattg agtttataac ttgtgtgata    4980
ttcctgcagt ttttatccaa taacattgtg ggaaaggttt gggggactga acgagcataa    5040
ataaatgtag caaaatttct ttctaacctg cctaaactct aggccatttt ataaggttat    5100
gttcctttga aaattcattt tggtcttttt accacatctg tcacaaaaag ccaggtctta    5160
gcgggctctt agaaactctg agaattttct tcagattcat tgagagagtt ttccataaag    5220
acatttatat atgtgagcaa gattttttt aaacaattac tttattattg ttgttattaa    5280
tgttattttc agaatggctt ttttttttct attcaaaatc aaatcgagat ttaatgtttg    5340
gtacaaaccc agaaagggta tttcatagtt tttaaaacctt tcattcccag agatccgaaa    5400
tatcatttgt gggttttgaa tgcatccttta aagtgcttta aaaaaaagtt ttataagtag    5460
ggagaaattt ttaaatattc ttacttggat ggctgcaact aaactgaaca aatacctgac    5520 ttttcttta ccccattgaa aatagtactt tcttcgtttc acaaattaaa aaaaaatct    5580 ggtatcaacc cacatttggg ctgtctagta ttcatttaca tttagggttc accaggacta    5640
atgattttta taaccgtttt tctggggtgt accaaaaaca tttgaatagg tttagaatag    5700
ctagaatagt tccttgactt tcctcgaatt tcattaccct ctcagcatgc ttgcagagag    5760
ctgggtgggc tcattcttgc agtcatactg cttatttagt gctgtatttt ttaaacgttt    5820
ctgttcagag aacttgctta atcttccata tattctgctc agggcacttg caattattag    5880
gttttgtttt tcttttttgtt ttttagcctt tgatggtaag aggaatacgg gctgccacat    5940
agactttgtt ctcattaata tcactatttta caactcatgt ggactcagaa aaacacacac    6000 cacctttttgg cttacttcga gtattgaatt gactggatcc actaaaccaa cactaagatg    6060
```

```
ggaaaacaca catggtttgg agcaatagga acatcatcat aattttttgtg gttctatttc    6120 aggtatagga attataaaat aattggttct ttctaaacac ttgtcccatt tcattctctt    6180
gcttttttag catgtgcaat actttctgtg ccaatagagt ctgaccagtg tgctatatag    6240
ttaaagctca ttcccttttg gcttttttcct tgtttggttg atcttcccca ttctggccag   6300
agcagggctg gagggaagga gccaggaggg agagagcctc ccacctttcc cctgctgcgg    6360
atgctgagtg ctggggcggg gagccttcag gagccccgtg cgtctgccgc cacgttgcag   6420
aaagagccag ccaaggagac ccggggggagg aaccgcagtg tccctgtca ccacacggaa    6480 tagtgaatgt ggagtgtgga gaggaaggag gcagattcat ttctaagacg cactctggag   6540
ccatgtagcc tggagtcaac ccattttcca cggtcttttc tgcaagtggg caggcccctc    6600 ctcgggtct gtgtccttga gacttggagc cctgcctctg agcctggacg ggaagtgtgg    6660
cctgttgtgt gtgtgcgttc tgagcgtgtt ggccagtggc tgtggagggg accacctgcc    6720
acccacggtc accactccct tgtggcagct ttctcttcaa ataggaagaa cgcacagagg    6780
gcaggagcct cctgtttgca gacgttggcg ggccccgagg ctcccagagc agcctctgtc    6840
accgcttctg tgtagcaaac attaacgatg acagggggtag aaattcttcg gtgccgttca   6900
gcttacaagg atcagccatg tgcctctgta ctatgtccac tttgcaatat ttaccgacag    6960
ccgtcttttg ttcttttcttt cctgttttcc atttttaaac tagtaacagc aggccttttg   7020
cgtttacaat ggaacacaat caccaagaaa ttagtcaggg cgaaaagaaa aaaataatac    7080
tattaataag aaaccaacaa acaagaacct ctctttctag ggatttctaa atatataaaa    7140
tgactgttcc ttagaatgtt taacttaaga attatttcag tttgtctggg ccacactggg    7200
gcagaggggg gagggaggga tacagagatg gatgccactt acctcagatc tttttaaagtg    7260 gaaatccaaa ttgaattttc atttggactt tcaggataat tttctatgtt ggtcaacttt     7320 tcgtttttccc taactcaccc agtttagttt gggatgattt gatttctgtt gttgttgatc    7380
ccatttctaa cttggaattg tgagcctcta tgttttctgt taggtgagtg tgtttgggttt    7440 tttccccccca ccaggaagtg gcagcatccc tccttctccc ctaaagggac tctgcggaac    7500 cttttcacacc tctttctcag ggacggggca ggtgtgtgtg tggtacactg acgtgtccag    7560
aagcagcact ttgactgctc tggagtaggg ttgtacaatt tcaaggaatg tttggatttc    7620
ctgcatcttg tggattactc cttagatacc gcatagattg caatataatg ctgcatgttc    7680
aagatgaaca gtagctccta gtaatcataa aatccactct ttgcacagtt tgatctttac    7740
tgaaatatgt tgccaaaatt tatttttgtt gttgtagctc tggattttgt tttgttttgt    7800
tttttaagga aacgattgac aatacccttt aacatctgtg actactaagg aaacctattt    7860
ctttcataga gagaaaaatc tccaatgctt ttgaagacac taataccgtg ctatttcaga    7920
tatgggtgag gaagcagagc tctcggtacc gaaggccggg cttcttgagc tgtgttggtt     7980
gtcatggcta ctgtttcatg aaccacaagc agctcaacag actggtctgt tgccttctga    8040 aacccctttgc acttcaattt gcaccaggtg aaaacagggc cagcagactc catggcccaa   8100
ttcggtttct tcggtggtga tgtgaaagga gagaattaca cttttttttt ttttaagtgg    8160
cgtggaggcc tttgcttcca catttgtttt taacccagaa tttctgaaat agagaattta    8220
agaacacatc aagtaataaa tatacagaga atatactttt ttataaagca catgcatctg   8280
ctattgtgtt gggttggttt cctctctttt ccacggacag tgttgtgttt ctggcatagg    8340
gaaactccaa acaacttgca cacctctact ccggagctga gatttctttt acatagatga    8400
```

-continued

```
cctcgcttca aatacgttac cttactgatg ataggatctt ttcttgtagc actataccttt    8460 gtgggaattt ttttttaaat gtacacctga tttgagaagc tgaagaaaac aaaatttgta    8520
agcactcact ttgaggagta caggtaatgt tttaaaaaat tgcacaaaag aaaaatgaat    8580
gtcgaaatga ttcattcagt gtttgaaaga tatggctctg ttgaaacaat gagtttcata    8640
ctttgtttgt aaaaaaaaaa aagcagagaa gggttgaaag ttacatgttt ttttgtatat    8700
agaaatttgt catgtctaaa tgatcagatt tgtatggtta tggcctggaa gaattactac    8760
gtaaaaggct cttaaactat acctatgctt attgttattt ttgttacata tagccctcgt    8820
ctgagggagg ggaactcggt attctgcgat ttgagaatac tgttcattcc tatgctgaaa    8880
gtacttctct gagctccctt cttagtctaa actcttaagc cattgcaact tcttttttctt    8940 cagagatgat gtttgacatt ttcagcactt cctgttccta taaacccaaa gaatataatc    9000
ttgaacacga agtgtttgta acaagggatc caggctacca atcaaacagg actcattatg    9060
gggacaaaaa aaaaaattat ttcaccttct ttcccccccac acctcattta aatgggggga    9120
gtaaaaacat gatttcaatg taaatgcctc attttatttt agttttattt tgattttttat    9180 ttaatataaa gaggccagaa taaatacgga gcatcttctc agaatagtat tcctgtccaa    9240
aaatcaagcc ggacagtgga aactggacag ctgtggggat attaagcacc cccacttaca    9300
attcttaaat tcagaatctc gtcccctccc ttctcgttga aggcaactgt tctggtagct    9360
aactttctcc tgtgtaatgg cgggagggaa caccggcttc agttttttcat gtccccatga    9420 cttgcataca aatggttcaa ctgtattaaa attaagtgca tttggccaat aggtagtatc    9480
tatacaataa caacaatctc taagaatttc cataactttt cttatctgaa aggactcaag    9540
tcttccactg cagatacatt ggaggcttca cccacgtttt cttttccctttt agtttgtttg    9600 ctgtctggat ggccaatgag cctgtctcct tttctgtggc caatctgaag gccttcgttg    9660
gaagtgttgt ttacagtaat ccttaccaag ataacatact gtcctccaga ataccaagta    9720
ttaggtgaca ctagctcaag ctgttgtctt cagagcagtt accaagaagc tcggtgcaca    9780
ggttttctct ggttcttaca ggaaccacct actctttcag ttttctggcc caggagtggg    9840
gtaaatcctt tagttagtgc atttgaactt gatacctgtg cattcagttc tgtgaatact    9900 gcccttttg gcggggtttc ctcatctccc cagcctgaac tgctcaactc taaacccaaa    9960
ttagtgtcag ccgaaaggag gtttcaagat agtcctgtca gtatttgtgg tgaccttcag   10020
attagacagt cttcatttcc agccagtgga gtcctggctc cagagccatc tctgagactc   10080
gtactactgg atgttttaat atcagatcat tacccaccat atgcctccca caggccaagg   10140
gaaaacagac accagaactt gggttgaggg cactaccaga ctgacatggc cagtacagag   10200
gagaactagg gaaggaatga tgttttgcac cttattgaaa agaaaatttt aagtgcatac   10260
ataatagtta agagctttta ttgtgacagg agaacttttt tccatatgcg tgcatactct   10320
ctgtaattcc agtgtaaaat attgtacttg cactagcttt tttaaacaaa tattaaaaaa   10380
tggaagaatt catattctat tttctaatcg tggtgtgtct atttgtagga tacactcgag   10440
tctgtttatt gaattttatg gtcccttttct ttgatggtgc ttgcaggttt tctaggtaga   10500
aattatttca ttattataat aaaacaatgt ttgattcaaa atttgaacaa aattgtttta   10560
aataaattgt ctgtataccca gtacaagttt attgtttcag tatactcgta ctaataaaat   10620
aacagtgcca attgca                                                   10636
```

<210> SEQ ID NO 82
<211> LENGTH: 4712

<212> TYPE: DNA
<213> ORGANISM: Homo sapiens

<400> SEQUENCE: 82

| | | | | | |
|---|---|---|---|---|---|
| accccccgaga | aagcaaccca | gcgcgccgcc | cgctcctcac | gtgtccctcc | cggccccggg | 60 |
| gccacctcac | gttctgcttc | cgtctgaccc | ctccgacttc | cggtaaagag | tccctatccg | 120 |
| cacctccgct | cccacccggc | gcctcggcgc | gcccgccctc | cgatgcgctc | agcggccgca | 180 |
| gctcctcgga | gtcccgcggt | ggccaccgag | tctcgccgct | tcgccgcagc | caggtggccc | 240 |
| gggtggcgct | cgctccagcg | gccggcgcgg | cggagcgggc | ggggcggcgg | tggcgcggcc | 300 |
| ccgggaccgt | atccctccgc | cgcccctccc | ccgcccggcc | ccggccccc | tccctcccgg | 360 |
| cagagctcgc | ctccctccgc | ctcagactgt | tttggtagca | acggcaacgg | cggcggcgcg | 420 |
| tttcggcccg | gctccggcg | gctccttggt | ctcggcgggc | ctccccgccc | cttcgtcgtc | 480 |
| ctccttctcc | ccctcgccag | cccgggcgcc | cctccggccg | cgccaacccg | cgcctccccg | 540 |
| ctcggcgccc | gcgcgtcccc | gccgcgttcc | ggcgtctcct | ggcgcgccc | ggctcccggc | 600 |
| tgtccccgcc | cggcgtgcga | gccggtgtat | gggcccctca | ccatgtcgct | gaagcccag | 660 |
| cagcagcagc | agcagcagca | gcagcagcag | cagcagcaac | agcagcagca | gcagcagcag | 720 |
| cagcagccgc | cgcccgcggc | tgccaatgtc | cgcaagcccg | gcggcagcgg | ccttctagcg | 780 |
| tcgcccgccg | ccgcgccttc | gccgtcctcg | tcctcggtct | cctcgtcctc | ggccacggct | 840 |
| ccctcctcgg | tggtcgcggc | gacctccggc | ggcgggaggc | ccggcctggg | cagaggtcga | 900 |
| aacagtaaca | aaggactgcc | tcagtctacg | atttcttttg | atggaatcta | tgcaaatatg | 960 |
| aggatggttc | atatacttac | atcagttgtt | ggctccaaat | gtgaagtaca | agtgaaaaat | 1020 |
| ggaggtatat | atgaaggagt | ttttaaaact | tacagtccga | agtgtgattt | ggtacttgat | 1080 |
| gccgcacatg | agaaaagtac | agaatccagt | tcggggccga | aacgtgaaga | aataatggag | 1140 |
| agtattttgt | tcaaatgttc | agactttgtt | gtggtacagt | ttaaagatat | ggactccagt | 1200 |
| tatgcaaaaa | gagatgcttt | tactgactct | gctatcagtg | ctaaagtgaa | tggcgaacac | 1260 |
| aaagagaagg | acctggagcc | ctgggatgca | ggtgaactca | cagccaatga | ggaacttgag | 1320 |
| gctttggaaa | atgacgtatc | taatggatgg | gatcccaatg | atatgtttcg | atataatgaa | 1380 |
| gaaaattatg | tgtagtgtc | tacgtatgat | agcagtttat | cttcgtatac | agtgccctta | 1440 |
| gaaagagata | actcagaaga | attttttaaaa | cgggaagcaa | gggcaaacca | gttagcagaa | 1500 |
| gaaattgagt | caagtgccca | gtacaaagct | cgagtggccc | tggaaaatga | tgataggagt | 1560 |
| gaggaagaaa | aatacacagc | agttcagaga | aattccagtg | aacgtgaggg | gcacagcata | 1620 |
| aacactaggg | aaaataaata | tattcctcct | ggacaaagaa | atagagaagt | catatcctgg | 1680 |
| ggaagtggga | gacagaattc | accgcgtatg | ggccagcctg | gatcgggctc | catgccatca | 1740 |
| agatccactt | ctcacacttc | agatttcaac | ccgaattctg | gttcagacca | aagagtagtt | 1800 |
| aatgaggtg | ttccctggcc | atcgccttgc | ccatctcctt | cctctcgccc | accttctcgc | 1860 |
| taccagtcag | gtcccaactc | tcttccacct | cgggcagcca | ccctacacg | gccgccctcc | 1920 |
| aggccccct | cgcggccatc | cagaccccg | tctcacccct | ctgctcatgg | ttctccagct | 1980 |
| cctgtctcta | ctatgcctaa | acgcatgtct | tcagaagggc | ctccaaggat | gtccccaaag | 2040 |
| gcccagcgac | atcctcgaaa | tcacagagtt | tctgctggga | ggggttccat | atccagtggc | 2100 |
| ctagaatttg | tatcccacaa | cccacccagt | gaagcagcta | ctcctccagt | agcaaggacc | 2160 |
| agtccctcgg | ggggaacgtg | gtcatcagtg | gtcagtgggg | ttccaagatt | atcccctaaa | 2220 |

-continued

```
actcatagac ccaggtctcc cagacagaac agtattggaa ataccccag tgggccagtt    2280 cttgcttctc cccaagctgg tattattcca actgaagctg ttgccatgcc tattccagct    2340
gcatctccta cgcctgctag tcctgcatcg aacagagctg ttaccccttc tagtgaggct    2400
aaagattcca ggcttcaaga tcagaggcag aactctcctg cagggaataa agaaaatatt    2460
aaacccaatg aaacatcacc tagcttctca aaagctgaaa acaaaggtat atcaccagtt    2520
gtttctgaac atagaaaaca gattgatgat ttaaagaaat ttaagaatga ttttaggtta    2580
cagccaagtt ctacttctga atctatggat caactactaa acaaaaatag agagggagaa    2640
aaatcaagag atttgatcaa agacaaaatt gaaccaagtg ctaaggattc tttcattgaa    2700
aatagcagca gcaactgtac cagtggcagc agcaagccga atagccccag catttcccct    2760
tcaatactta gtaacacgga gcacaagagg ggacctgagg tcacttccca aggggttcag    2820
acttccagcc cagcatgtaa acaagagaaa gacgataagg aagagaagaa agacgcagct    2880
gagcaagtta ggaaatcaac attgaatccc aatgcaaagg agttcaaccc acgttccttc    2940
tctcagccaa agccttctac taccccaact tcacctcggc tcaagcaca acctagccca    3000 tctatggtgg gtcatcaaca gccaactcca gtttatactc agcctgtttg ttttgcacca    3060
aatatgatgt atccagtccc agtgagccca ggcgtgcaac ctttataccc aatacctatg    3120
acgcccatgc cagtgaatca agccaagaca tatagagcag taccaaatat gccccaacag    3180
cggcaagacc agcatcatca gagtgccatg atgcacccag cgtcagcagc gggcccaccg    3240
attgcagcca ccccaccagc ttactccacg caatatgttg cctacagtcc tcagcagttc    3300
ccaaatcagc cccttgttca gcatgtgcca cattatcagt ctcagcatcc tcatgtctat    3360
agtcctgtaa tacagggtaa tgctagaatg atggcaccac caacacacgc ccagcctggt    3420
ttagtatctt cttcagcaac tcagtacggg gctcatgagc agacgcatgc gatgtatgca    3480
tgtcccaaat taccatacaa caaggagaca gcccttctt tctactttgc catttccacg    3540
ggctcccttg ctcagcagta tgcgcaccct aacgctaccc tgcacccaca tactccacac    3600
cctcagcctt cagctacccc cactggacag cagcaaagcc aacatggtgg aagtcatcct    3660
gcacccagtc ctgttcagca ccatcagcac caggccgccc aggctctcca tctggccagt    3720
ccacagcagc agtcagccat ttaccacgcg gggcttgcgc caactccacc ctccatgaca    3780
cctgcctcca acacgcagtc gccacagaat agtttcccag cagcacaaca gactgtcttt    3840
acgatccatc cttctcacgt tcagccggcg tataccaacc caccccacat ggcccacgta    3900
cctcaggctc atgtacagtc aggaatggtt ccttctcatc caactgccca tgcgccaatg    3960
atgctaatga cgacacagcc acccggcggt ccccaggccg ccctcgctca aagtgcacta    4020
cagcccattc cagtctcgac aacagcgcat ttccccctata tgacgcaccc ttcagtacaa    4080
gcccaccacc aacagcagtt gtaaggctgc cctggaggaa ccgaaaggcc aaattccctc    4140
ctcccttcta ctgcttctac caactggaag cacagaaaac tagaatttca tttattttgt    4200
ttttaaaata tatatgttga tttcttgtaa catccaatag gaatgctaac agttcacttg    4260
cagtggaaga tacttggacc gagtagaggc atttaggaac ttgggggcta ttccataatt    4320
ccatatgctg tttcagagtc ccgcaggtac cccagctctg cttgccgaaa ctggaagtta    4380
tttatttttt aataacccct tgaaagtcatg aacacatcag ctagcaaaag aagtaacaag    4440
agtgattctt gctgctatta ctgctaaaaa aaaaaaaaa aaaaaatcaa gacttggaac    4500
gcccttttac taaacttgac aaagtttcag taaattctta ccgtcaaact gacgattat    4560 tatttataaa tcaagtttga tgaggtgatc actgtctaca gtggttcaac ttttaagtta    4620
```

| | |
|---|---|
| agggaaaaac ttttactttg tagataatat aaaataaaaa cttaaaaaaa atttaaaaaa | 4680 |
| taaaaaaagt tttaaaaact gaaaaaaaaa aa | 4712 |

<210> SEQ ID NO 83
<211> LENGTH: 6923
<212> TYPE: DNA
<213> ORGANISM: Homo sapiens

<400> SEQUENCE: 83

| | |
|---|---|
| gagaggggca gggggcggag ctggaggggg tggttcggcg tggggccgt tggctccaga | 60 |
| caaataaaca tggagtccat cttccacgag aaacaagaag gctcactttg tgctcaacat | 120 |
| tgcctgaata acttattgca aggagaatat tttagccctg tggaattatc ctcaattgca | 180 |
| catcagctgg atgaggagga gaggatgaga atggcagaag gaggagttac tagtgaagat | 240 |
| tatcgcacgt ttttacagca gccttctgga aatatggatg acagtggttt tttctctatt | 300 |
| caggttataa gcaatgcctt gaaagtttgg ggtttagaac taatcctgtt caacagtcca | 360 |
| gagtatcaga ggctcaggat cgatcctata aatgaaagat catttatatg caattataag | 420 |
| gaacactggt ttacagttag aaaattagga aaacagtggt ttaacttgaa ttctctcttg | 480 |
| acgggtccag aattaatatc agatacatat cttgcacttt tcttggctca attacaacag | 540 |
| gaaggttatt ctatatttgt cgttaagggt gatctgccag attgcgaagc tgaccaactc | 600 |
| ctgcagatga ttagggtcca acagatgcat cgaccaaaac ttattggaga agaattagca | 660 |
| caactaaaag agcaaagagt ccataaaaca gacctggaac gagtgttaga agcaaatgat | 720 |
| ggctcaggaa tgttagacga agatgaggag gatttgcaga gggctctggc actaagtcgc | 780 |
| caagaaattg acatggaaga tgaggaagca gatctccgca gggctattca gctaagtatg | 840 |
| caaggtagtt ccagaaacat atctcaagat atgacacaga catcaggtac aaatcttact | 900 |
| tcagaagagc ttcggaagag acgagaagcc tactttgaaa aacagcagca aaagcagcaa | 960 |
| cagcagcagc agcagcagca gcaggggac ctatcaggac agagttcaca tccatgtgaa | 1020 |
| aggccagcca ccagttcagg agcacttggg agtgatctag gtgatgctat gagtgaagaa | 1080 |
| gacatgcttc aggcagctgt gaccatgtct ttagaaactg tcagaaatga tttgaaaaca | 1140 |
| gaaggaaaaa aataatacct ttaaaaaata atttagatat tcatactttc aacattatc | 1200 |
| ctgtgtgatt acagcatagg gtccactttg gtaatgtgtc aaagagatga ggaaataaga | 1260 |
| cttttagcgg tttgcaaaca aaatgatggg aaagtggaac aatgcgtcgg ttgtaggact | 1320 |
| aaataatgat cttccaaata ttagccaaag aggcattcag caattaaaga catttaaaat | 1380 |
| agttttctaa atgtttcttt ttctttttg agtgtgcaat atgtaacatg tctaaagtta | 1440 |
| gggcattttt cttggatctt tttgcagact agctaattag ctctcgcctc aggctttttc | 1500 |
| catatagttt gttttctttt tctgtcttgt aggtaagttg gctcacatca tgtaatagtg | 1560 |
| gctttcattt cttattaacc aaattaacct ttcaggaaag tatctctact ttcctgatgt | 1620 |
| tgataatagt aatggttcta gaaggatgaa cagttctccc ttcaactgta taccgtgtgc | 1680 |
| tccagtgttt tcttgtgttg ttttctctga tcacaacttt tctgctacct ggttttcatt | 1740 |
| attttcccac aattcttttg aaagatggta atctttctg aggtttagcg ttttaagccc | 1800 |
| tacgatggga tcattatttc atgactggtg cgttcctaaa ctctgaaatc agccttgcac | 1860 |
| aagtacttga gaataaatga gcatttttta aaatgtgtga gcatgtgctt tcccagatgc | 1920 |
| tttatgaatg tctttttcact tatatcaaaa ccttacagct ttgttgcaac cccttcttcc | 1980 |

```
tgcgccttat ttttccttt cttctccaat tgagaaaact aggagaagca tagtatgcag    2040
gcaagtctcc ttctgttaga agactaaaca tacgtaccca ccatgaatgt atgatacatg    2100
aaatttggcc ttcaatttta atagcagttt tattttattt tttctcctat gactggagct    2160
ttgtgttctc tttacagttg agtcatggaa tgtaggtgtc tgcttcacat cttttagtag    2220
gtatagcttg tcaaagatgg tgatctggaa catgaaaata atttactaat gaaatatgt     2280 ttaaatttat actgtgattt gacacttgca tcatgtttag atagcttaag aacaatggaa    2340
gtcacagtac ttagtggatc tataaataag aaagtccata gttttgataa atattctctt    2400
taattgagat gtacagagag tttcttgctg ggtcaatagg atagtatcat tttggtgaaa    2460
accatgtctc tgaaattgat gttttagttt cagtgttccc tatccctcat tctccatctc    2520
cttttgaagc tcttttgaat gttgaattgt cataagcta aaatccaaga aatttcagct     2580
gacaacttcg aaaattataa tatggtatat tgccctcctg gtgtgtggct gcacacattt    2640
tatcagggaa agttttttga tctaggattt attgctaact aactgaaaag agaagaaaaa    2700
atatctttta tttatgatta taaaatagct ttttcttcga tataacagat tttttaagtc    2760
attattttgt gccaatcagt tttctgaagt ttcccttaca caaaaggata gctttatttt    2820
aaaatctaaa gtttctttta atagttaaaa atgtttcaga agaattataa aactttaaaa    2880
ctgcaaggga tgttggagtt tagtactact ccctcaagat ttaaaaagct aaatatttta    2940
agactgaaca tttatgttaa ttattaccag tgtgtttgtc atattttcca tggatatttg    3000
ttcattacct ttttccattg aaaagttaca ttaaactttt catacacttg aattgatgag    3060
ctacctaata taaaaatgag aaaaccaata tgcattttaa agttttaact ttagagttta    3120
taaagttcat atataccccta gttaaagcac ttaagaaaat atggcatgtt tgactttag    3180 ttcctagaga gttttttgttt ttgttttttgt tttttttga acggagtct tgctatgtct    3240 cccaggctgg agggcagtgg catgatctcg gctcactaca acttccacct cccgggttca    3300
agcaattctc ctgcctcagc ctccagagta gctgggatta caggcgccca ccaccacacc    3360
cggcagattt ttgtattttt ggtagagacg cggtttcatc atgtttggcc aggctggtct    3420
cgaactcctg acctcaggtg atccgcctgc cttggcctcc caaagtgttg ggattacagg    3480
catgagccac tgcgcctggc cagctagaga gttttaaag cagagctgag cacacactgg    3540
atgcgtttga atgtgtttgt gtagtttgtt gtgaaattgt tacatttagc aggcagatcc    3600
agaagcacta gtgaactgtc atcttggtgg ggttggctta aatttaattg actgtttaga    3660
ttccatttct taattgattg gccagtatga aaagatgcca gtgcaagtaa ccatagtatc    3720 aaaaagtta aaaattattc aaagctatag tttatacatc aggtactgcc atttactgta    3780
aaccacctgc aagaaagtca ggaacaacta aattcacaag aactgtcctg ctaagaagtg    3840
tattaaagat ttccattttg ttttactaat tgggaacatc ttaatgttta atatttaaac    3900
tattggtatc attttttctaa tgtataattt gtattactgg gatcaagtat gtacagtggt    3960
gatgctagta gaagtttaag ccttggaaat accactttca tattttcaga tgtcatggat    4020
ttaatgagta atttatgttt ttaaaattca gaatagttaa tctctgatct aaaaccatca    4080
atctatgttt tttacggtaa tcatgtaaat atttcagtaa tataaactgt ttgaaaggc     4140 tgctgcaggt aaactctata ctaggatctt ggccaaataa tttacaattc acagaatatt    4200
ttatttaagg tggtgctttt ttttttgtc cttaaaactt gattttttctt aactttattc    4260 atgatgccaa agtaaatgag gaaaaaaact caaaaccagt tgagtatcat tgcagacaaa    4320
actaccagta gtccatattg tttaatatta agttgaataa aataaatttt atttcagtca    4380
```

```
gagcctaaat cacatttga ttgtctgaat ttttgatact attttttaaaa tcatgctagt    4440 ggcggctggg cgtggtagct cacgcctgta atcccagcat tttgggaggc cgaagtgggg    4500
ggatcacgag gtcgggagtt cgagaccagc ttggccaaaa tggtgaaacc ccatctgtac    4560
taaaaactac aaaaattagc tgggcgcggt ggcaggtgcc tgtaatccca gctacctggg    4620
agtctgaggc aggagaattg cttgaaccct ggcgacagag gatgcagtga gccaagatgg    4680
tgccactgta ctccagactg ggcgacagag tgagactctg tctcaaaaaa aaaaaaaaaa    4740
tcatgctagt gccaagagct actaaattct aaaaccggc ccattggacc tgtacagata     4800
aaaaatagat tcagtgcata atcaaaatat gataatttta aaatcttaag tagaaaaata    4860
aatcttgatg ttttaaattc ttacgaggat tcaatagtta atattgatga tctcccggct    4920
gggtgcagtg gctcacgcct gtaatcccag cagttctgga ggctgaggtg ggcgaatcac    4980
ttcaggccag gagttcaaga ccagtctggg caacatggtg aaacctcgtt tctactaaaa    5040
atacaaaaat tagccgggcg tggttgcaca cacttgtaat cccagctact caggaggcta    5100
agaatcgcat gagcctagga ggcagaggtt gcagagtgcc aagggctcac cactgcattc    5160
cagcctgccc aacagagtga gacactgttt ctgaaaaaaa aaaatatata tatatatata    5220
tatatgtgtg tatatatata tgtatatata tatgacttcc tattaaaaac tttatcccag    5280
tcgggggcag tggctcacgc ctgtaatccc aacactttgg gaggctgagg caggtggatc    5340
acctgaagtc cggagtttga ccagcctg ccaacatgg tgaaacccca tctctactaa       5400
aaatacaaaa cttaagccag gtatggtggc gggcacctgt aatcccagtt acttgggagg    5460
ctgaggcagg agaatcgttt aaacccagga ggtggaggtt gcagtgagct gagatcgtgc    5520
cattgcactc tagcctgggc aacaagagta aaactccatc ttaaaggttt gtttgttttt    5580
ttttaatccg gaaacgaaga ggcgttgggc cgctatttc ttttctttc tttctttctt      5640 tcttttttt ttttctgag acggagtcta gctctgctgc ccaggctgga gtacaatgac      5700
acgatgttgg ctcactgcaa cctccacctc ctgggttcaa gcgattctcc tgcctcagcc    5760
tcccaagtac ctgggattac aggcacctgc cactacacct ggcgaatatt tgttttttt    5820 agtagagacg ggcttttacc atgttaggct ggtctcaaac tcctgacctc aggtgatctg    5880
cctgccttgg cctcccaaag tgctgggatt acaggtgcag gccaccacac ccggccttgg    5940
gccactgttt tcaaagtgaa ttgtttgttg tatcgagtcc ttaagtatgg atatatatgt    6000
gaccctaatt aagaactacc agattggatc aactaatcat gtcagcaatg taaataactt    6060
tatttttcat attcaaaata aaactttct tttattctg gcccctttat aaccagcatc      6120
tttttgcttt aaaaaatgac ctggctttgt attttttag tcttaaacat aataaaaata    6180 ttttgttct aatttgcttt catgagtgaa gattattgac atcgttggta aattctagaa     6240
ttttgatttt gtttttaat ttgaagaaaa tctttgctat tattatttt tccaagtggt     6300 ctggcatttt aagaattagt gctaataacg taacttctaa atttgtcgta attggcatgt    6360
ttaatagcat atcaaaaaac attttaagcc tgtggattca tagacaaagc aatgagaaac    6420
attagtaaaa tataaatgga tattcctgat gcatttagga agctctcaat tgtctcttgc    6480
atagttcaag gaatgttttc tgaattttt taatgctttt ttttttttg aaagaggaaa    6540 acatacattt ttaaatgtga ttatctaatt tttacaacac tgggctatta ggaataactt    6600
tttaaaaatt actgttctgt ataaatattt gaaattcaag tacagaaaat atctgaaaca    6660
aaaagcattg ttgtttggcc atgatacaag tgcactgtgg cagtgccgct tgctcaggac    6720
```

| | |
|---|---|
| ccagccctgc agcccttctg tgtgtgctcc ctcgttaagt tcatttgctg ttattacaca | 6780 |
| cacaggcctt cctgtctggt cgttagaaaa gccgggcttc caaagcactg ttgaacacag | 6840 |
| gattctgttg ttagtgtgga tgttcaatga gttgtatttt aaatatcaaa gattattaaa | 6900 |
| taaagataat gtttgctttt cta | 6923 |

<210> SEQ ID NO 84
<211> LENGTH: 8646
<212> TYPE: DNA
<213> ORGANISM: Homo sapiens

<400> SEQUENCE: 84

| | |
|---|---|
| gatgtcccga gctgctatcc ccggctcggc ccgggcagcc gccttctgag cccccgaccc | 60 |
| gaggcgccga gccgccgccg cccgatgggc tgggccgtgg agcgtctccg cagtcgtagc | 120 |
| tccagccgcc gcgctcccag ccccggcagc ctcagcatca gcggcggcgg cggcggcggc | 180 |
| ggcgtcttcc gcatcgttcg ccgcagcgta acccggagcc ctttgctctt tgcagaatgg | 240 |
| cccgcttcgg agacgagatg ccggcccgct acggggagg aggctccggg gcagccgccg | 300 |
| gggtggtcgt gggcagcgga ggcgggcgag gagccggggg cagccggcag ggcgggcagc | 360 |
| ccggggcgca aaggatgtac aagcagtcaa tggcgcagag agcgcggacc atggcactct | 420 |
| acaaccccat ccccgtccga cagaactgcc tcacggttaa ccggtctctc ttcctcttca | 480 |
| gcgaagacaa cgtggtgaga aaatacgcca aaaagatcac cgaatggcct cccttgaat | 540 |
| atatgatttt agccaccatc atagcgaatt gcatcgtcct cgcactggag cagcatctgc | 600 |
| ctgatgatga caagaccccg atgtctgaac ggctggatga cacagaacca tacttcattg | 660 |
| gaattttttg tttcgaggct ggaattaaaa tcattgccct tgggtttgcc ttccacaaag | 720 |
| gctcctactt gaggaatggc tggaatgtca tggactttgt ggtggtgcta acgggcatct | 780 |
| tggcgacagt tgggacggag tttgacctac ggacgctgag ggcagttcga gtgctgcggc | 840 |
| cgctcaagct ggtgtctgga atcccaagtt tacaagtcgt cctgaagtcg atcatgaagg | 900 |
| cgatgatccc tttgctgcag atcggcctcc tctattttt tgcaatcctt atttttgcaa | 960 |
| tcatagggtt agaattttat atgggaaaat tcataccac ctgctttgaa gaggggacag | 1020 |
| atgacattca gggtgagtct ccggctccat gtgggacaga agagcccgcc cgcacctgcc | 1080 |
| ccaatgggac caaatgtcag ccctactggg aagggcccaa caacgggatc actcagttcg | 1140 |
| acaacatcct gtttgcagtg ctgactgttt tccagtgcat aaccatggaa gggtggactg | 1200 |
| atctcctcta caatagcaac gatgcctcag ggaacacttg gaactggttg tacttcatcc | 1260 |
| ccctcatcat catcggctcc tttttatgc tgaaccttgt gctgggtgtg ctgtcagggg | 1320 |
| agtttgccaa agaaagggaa cgggtggaga accggcgggc ttttctgaag ctgaggcggc | 1380 |
| aacaacagat tgaacgtgag ctcaatgggt acatggagtg gatctcaaaa gcagaagagg | 1440 |
| tgatcctcgc cgaggatgaa actgacgggg agcagaggca tccctttgat ggagctctgc | 1500 |
| ggagaaccac cataaagaaa agcaagacag atttgctcaa ccccgaagag gctgaggatc | 1560 |
| agctggctga tatagcctct gtgggttctc ccttcgcccg agccagcatt aaaagtgcca | 1620 |
| agctggagaa ctcgaccttt tttcacaaaa aggagaggag gatgcgtttc tacatccgcc | 1680 |
| gcatggtcaa aactcaggcc ttctactgga ctgtactcag tttggtagct ctcaacacgc | 1740 |
| tgtgtgttgc tattgttcac tacaaccagc ccgagtggct ctccgacttc ctttactatg | 1800 |
| cagaattcat tttcttagga ctctttatgt ccgaaatgtt tataaaaatg tacgggcttg | 1860 |
| ggacgcggcc ttacttccac tcttccttca actgctttga ctgtgggggtt atcattggga | 1920 |

-continued

```
gcatcttcga ggtcatctgg gctgtcataa aacctggcac atcctttgga atcagcgtgt    1980
tacgagccct caggttattg cgtattttca aagtcacaaa gtactgggca tctctcagaa    2040
acctggtcgt ctctctcctc aactccatga agtccatcat cagcctgttg tttctccttt    2100
tcctgttcat tgtcgtcttc gcccttttgg gaatgcaact cttcggcggc cagtttaatt    2160
tcgatgaagg gactcctccc accaacttcg atacttttcc agcagcaata atgacggtgt    2220
ttcagatcct gacgggcgaa gactggaacg aggtcatgta cgacgggatc aagtctcagg    2280
ggggcgtgca gggcggcatg gtgttctcca tctatttcat tgtactgacg ctctttggga    2340
actacaccct cctgaatgtg ttcttggcca tcgctgtgga caatctggcc aacgcccagg    2400
agctcaccaa ggtggaggcg gacgagcaag aggaagaaga agcagcgaac cagaaacttg    2460
ccctacagaa agccaaggag gtggcagaag tgagtcctct gtccgcggcc aacatgtcta    2520
tagctgtgaa agagcaacag aagaatcaaa agccagccaa gtccgtgtgg gagcagcgga    2580
ccagtgagat gcgaaagcag aacttgctgg ccagccggga ggccctgtat aacgaaatgg    2640
acccggacga gcgctggaag gctgcctaca cgcggcacct gcggccagac atgaagacgc    2700
acttggaccg gccgctggtg gtggacccgc aggagaaccg caacaacaac accaacaaga    2760
gccgggcggc cgagcccacc gtggaccagc gcctcggcca gcagcgcgcc gaggacttcc    2820
tcaggaaaca ggcccgctac cacgatcggg cccgggaccc cagcggctcg gcgggcctgg    2880
acgcacggag gccctgggcg ggaagccagg aggccgagct gagccgggag ggaccctacg    2940
gccgcgagtc ggaccaccac gcccgggagg gcagcctgga gcaacccggg ttctgggagg    3000
gcgaggccga gcgaggcaag gccggggacc cccaccggag gcacgtgcac cggcaggggg    3060
gcagcaggga gagccgcagc gggtccccgc gcacgggcgc ggacggggag catcgacgtc    3120
atcgcgcgca ccgcaggccc ggggaggagg gtccggagga caaggcggag cggagggcgc    3180
ggcaccgcga gggcagccgg ccggcccggg gcggcgaggg cgagggcgag gccccgacg    3240
ggggcgagcg caggagaagg caccggcatg gcgctccagc cacgtacgag ggggacgcgc    3300
ggagggagga caaggagcgg aggcatcgga ggaggaaaga gaaccagggc tccggggtcc    3360
ctgtgtcggg ccccaacctg tcaaccaccc ggccaatcca gcaggacctg ggccgccaag    3420
acccacccct ggcagaggat attgacaaca tgaagaacaa caagctggcc accgcggagt    3480
cggccgctcc ccacgcagc cttggccacg ccggcctgcc ccagagccca gccaagatgg    3540
gaaacagcac cgaccccggc cccatgctgg ccatccctgc catggccacc aaccccccaga    3600
acgccgccac ccgccggacg cccaacaacc cggggaaccc atccaatccc ggccccccca    3660
agacccccga gaatagcctt atcgtcacca accccagcgg caccagacc aattcagcta    3720
agactgccga gaaacccgac cacaccacag tggacatccc ccagcctgc ccacccccc    3780
tcaaccacac cgtcgtacaa gtgaacaaaa acgccaaccc agacccactg ccaaaaaaag    3840
aggaagagaa gaaggaggag gaggaagacg accgtgggga agacgccct aagccaatgc    3900
ctccctatag ctccatgttc atcctgtcca cgaccaaccc ccttcgccgc ctgtgccatt    3960
acatcctgaa cctgcgctac tttgagatgt gcatcctcat ggtcattgcc atgagcagca    4020
tcgccctggc cgccgaggac cctgtgcagc ccaacgcacc tcggaacaac gtgctgcgat    4080
actttgacta cgttttttaca ggcgtcttta cctttgagat ggtgatcaag atgattgacc    4140
tggggctcgt cctgcatcag ggtgcctact tccgtgacct ctggaatatt ctcgacttca    4200
tagtggtcag tgggggccctg gtagcctttg ccttcactgg caatagcaaa ggaaaagaca    4260
```

```
tcaacacgat taaatccctc cgagtcctcc gggtgctacg acctcttaaa accatcaagc    4320
ggctgccaaa gctcaaggct gtgtttgact gtgtggtgaa ctcacttaaa aacgtcttca    4380
acatcctcat cgtctacatg ctattcatgt tcatcttcgc cgtggtggct gtgcagctct    4440
tcaaggggaa attcttccac tgcactgacg agtccaaaga gtttgagaaa gattgtcgag    4500
gcaaataccT cctctacgag aagaatgagg tgaaggcgcg agaccgggag tggaagaagt    4560
atgaattcca ttacgacaat gtgctgtggg ctctgctgac cctcttcacc gtgtccacgg    4620
gagaaggctg gccacaggtc ctcaagcatt cggtggacgc cacctttgag aaccagggcc    4680
ccagccccgg gtaccgcatg gagatgtcca ttttctacgt cgtctacttt gtggtgttcc    4740
ccttcttctt tgtcaatatc tttgtggcct tgatcatcat caccttccag gagcaagggg    4800
acaagatgat ggaggaatac agcctggaga aaaatgagag ggcctgcatt gatttcgcca    4860
tcagcgccaa gccgctgacc cgacacatgc cgcagaacaa gcagagcttc cagtaccgca    4920
tgtggcagtt cgtggtgtct ccgcctttcg agtacgat catggccatg atcgccctca    4980
acaccatcgt gcttatgatg aagttctatg ggcttctgt tgcttatgaa aatgccctgc    5040
gggtgttcaa catcgtcttc acctccctct tctctctgga atgtgtgctg aaagtcatgg    5100
cttttgggat tctgaattat ttccgcgatg cctggaacat cttcgacttt gtgactgttc    5160
tgggcagcat caccgatatc ctcgtgactg agtttgggaa tccgaataac ttcatcaacc    5220
tgagctttct ccgcctcttc cgagctgccc ggctcatcaa acttctccgt cagggttaca    5280
ccatccgcat tcttctctgg acctttgtgc agtccttcaa ggccctgcct tatgtctgtc    5340
tgctgatcgc catgctcttc ttcatctatg ccatcattgg gatgcaggtg tttggtaaca    5400
ttggcatcga cgtggaggac gaggacagtg atgaagatga gttccaaatc actgagcaca    5460
ataacttccg gaccttcttc caggcccctca tgcttctctt ccggagtgcc accggggaag    5520
cttggcacaa catcatgctt tcctgcctca gcgggaaacc gtgtgataag aactctggca    5580
tcctgactcg agagtgtggc aatgaatttg cttattttta ctttgtttcc ttcatcttcc    5640
tctgctcgtt tctgatgctg aatctctttg tcgccgtcat catggacaac tttgagtacc    5700
tcacccgaga ctcctccatc ctgggccccc accacctgga tgagtacgtg cgtgtctggg    5760
ccgagtatga ccccgcagct tggggccgca tgccttacct ggacatgtat cagatgctga    5820
gacacatgtc tccgccccctg ggtctgggga agaagtgtcc ggccagagtg gcttacaagc    5880
ggcttctgcg gatggacctg cccgtcgcag atgacaacac cgtccacttc aattccaccc    5940
tcatggctct gatccgcaca gccctggaca tcaagattgc caaggagga gccgacaaac    6000
agcagatgga cgctgagctg cggaaggaga tgatggcgat ttggcccaat ctgtcccaga    6060
agacgctaga cctgctggtc acacctcaca gtccacgga cctcaccgtg gggaagatct    6120
acgcagccat gatgatcatg gagtactacc ggcagagcaa ggccaagaag ctgcaggcca    6180
tgcgcgagga gcaggaccgg acaccctca tgttccagcg catggagccc cgtccccaa    6240
cgcaggaagg gggacctggc cagaacgccc tccctccac ccagctggac ccaggaggag    6300
ccctgatggc tcacgaaagc ggcctcaagg agagcccgtc ctgggtgacc cagcgtgccc    6360
aggagatgtt ccagaagacg ggcacatgga gtccggaaca aggccccct accgacatgc    6420
ccaacagcca gctaactctc cagtccgtgg agatgcgaga gatgggcaga gatggctact    6480
ccgacagcga gcactaccttc cccatggaag gccaggggccg ggctgcctcc atgcccgcc    6540
tccctgcaga gaaccagagg agaagggcc ggccacgtgg gaataacctc agtaccatct    6600
cagacaccag ccccatgaag cgttcagcct ccgtgctggg ccccaaggcc cgacgcctgg    6660
```

```
acgattactc gctggagcgg gtcccgcccg aggagaacca gcggcaccac cagcggcgcc    6720
gcgaccgcag ccaccgcgcc tctgagcgct ccctgggccg ctacaccgat gtggacacag    6780
gcttggggac agacctgagc atgaccaccc aatccgggga cctgccgtcg aaggagcggg    6840
accaggagcg gggccggccc aaggatcgga agcatcgaca gcaccaccac caccaccacc    6900
accaccacca tcccccgccc cccgacaagg accgctatgc ccaggaacgg ccggaccacg    6960
gccgggcacg ggctcgggac cagcgctggt cccgctcgcc cagcgagggc cgagagcaca    7020
tggcgcaccg gcagggcagt agttccgtaa gtggaagccc agcccctca acatctggta     7080 ccagcactcc gcggcgggc cgccgccagc tcccccagac cccctccacc cccggccac      7140 acgtgtccta ttcccctgtg atccgtaagg ccggcggctc ggggcccccg cagcagcagc    7200
agcagcagca gcagcagcag cagcagcagg cggtggccag gccgggccgg cggccacca     7260 gcggccctcg gaggtaccca ggcccacgg ccgagcctct ggccggagat cggccgccca     7320 cgggggggcca cagcagcggc cgctcgccca ggatggagag cgggtccca ggcccggcc      7380 ggagcgagtc ccccagggcc tgtcgacacg gcggggcccg gtggccggca tctggcccgc    7440
acgtgtccga ggggccccg ggtccccggc accatggcta ctaccggggc tccgactacg     7500
acgaggccga tgcccgggc agcggggcg gcgaggaggc catggccggg gcctacgacg      7560 cgccacccc cgtacgacac gcgtcctcgg gcgccaccgg gcgctcgccc aggactcccc     7620
gggcctcggg cccggcctgc gcctcgcctt ctcggcacgg ccggcgactc cccaacggct    7680 actaccggc gcacggactg gccaggcccc gcgggccggg ctccaggaag ggcctgcacg     7740
aaccctacag cgagagtgac gatgattggt gctaagcccg ggcgaggtgg cgcccgcccg    7800 gcccccacg cacccacgc acacacccca cccgaggagc cgcgcagagg ccgcgggggc      7860
ccagcacaga gggcccggga gagggccagc cgggagaccc cagactctgg agaggccagg    7920
gctgggccac aagggtgtcc cgcagagacc ctcggccaaa agagaccctc ctgggcagcc    7980
acggcgcccc ccaaccagcc ccgatccccc cacccacgac aggggctctc gggtgggagg    8040
cagggagcag acaaaccaca cagccaaggg atttgaatta actcagccat ttttggagaa    8100
cttttgggaa catgaaaaaa aaaaaaaaa aaaaaaaaaa aaacatttt aaagaaaaa       8160 acggggagaa aaaatagct tctattgatg agtttatca tctcaattga atctttcctt     8220
tccctgatga agacagctgg tggccgagtg cggcaaagaa gccagaagga accagaatcc    8280
cagtgcccta cacccaccac cagacacact cacacccaca cacgttctca gacacacaca    8340
agagtgcttg ccggttatac caaaccctac tattactgcc tgcagaaatc aatttaaaaa    8400
aataataata acaataaaca attttaaaaa ggacaaaaaa attaatgatt gagaaaagag    8460 gcatttttt ctgacatttg gtcctgcttg aaacaacaaa agaagaagaa aaacccacca    8520
tcaccaccga ttcctttgct tctttttcc tttttccta ccttgtttga aaaccgtggg     8580
cttgggactg tgaattattg catgacattc aaaagaaaa aaaaaataaa aaaaagttga    8640
atcaaa                                                              8646
```

<210> SEQ ID NO 85
<211> LENGTH: 7242
<212> TYPE: DNA
<213> ORGANISM: Homo sapiens

<400> SEQUENCE: 85

```
gaaaaagggt gaaagagaaa cttggcgacc tcccggagga gttcgcgaag cgaccaggag      60
```

```
cgtgttgcca tcgtcctcac ccggcaccca attccaccac agagtcggga tttcgtcggt    120
gatcgtgatg gggtgctttt attttctct ttgattttca aaaaatgtct atgtgactgt     180
ccctatctta agggggaagtt gaaagtgggg gcggggggtgc tcaatgagaa acgttgcctt  240
gtgtgtagtt gtttggagca cactgcaaat tatattggca tctctttcca aaagtcactt   300
tgattcaact tcgatagctt tctcgtaaat ggcacgttta ggtggtgaga ggtggatgag   360
gaaacaggca ccagtgcagc tgatttgacc tccagtggga tagatacgat tagcaccagg   420
atcgtgtctc attttgaacc cagatctgaa cagaattaag acgaacgagc tttcacaatt   480
gcagcagatg aagatccatt ggtaaattga tcaggatttt tggcctaccc tccaaagaaa   540
aggagcggaa agaatgtcgg agcgggccgc ggatgacgtc agggggggagc cgcgccgcgc  600 ggcggcggcg gcgggcggag cagcggccgc ggccgcccgg cagcagcagc agcagcagca   660
gcagcagcag ccgccgcctc cgcagcccca gcggcagcag caccccgccac cgccgccacg   720 gcgcacacgg ccggaggacg gcgggcccgg cgccgcctcc acctcggccg ccgcaatggc   780
gacggtcggg gagcgcaggc ctctgcccag tcctgaagtg atgctgggac agtcgtggaa   840
tctgtgggtt gaggcttcca aacttcctgg gaaggacggg acagaattgg acgaaagttt   900
caaggagttt gggaaaaacc gcgaagtcat ggggctctgt cggaagaca tgccaatatt    960 tggtttctgt ccagcccatg atgatttcta cttggtggtg tgtaacgact gtaatcaggt   1020
tgtcaaaccg caggcatttc aatcacatta tgaaagaaga catagctcat ccagcaagcc   1080
gcctttggcc gttcctccca cttcagtatt ttccttcttc ccttctctgt ccaaaagcaa   1140
aggaggcagt gcaagtggaa gcaaccgttc ttccagtgga ggtgttctta gcgcatcctc   1200
atcaagttcc aagttgttga aatcacccaa agagaaactg cagctcaggg ggaacaccag   1260
gccaatgcat cccattcagc aaagtagagt tccccatggt agaatcatga caccctctgt   1320
gaaagtggaa aagattcatc cgaaaatgga tggcacacta ctgaaatctg cggtggggcc   1380
aacctgtcct gctactgtga gttccttagt caagcctggc cttaactgcc cctcaatacc   1440
aaagccaacc ttgccttcac ctggacagat tctgaatggc aaagggcttc ctgcaccgcc   1500
cactctggaa aagaaacctg aagacaattc caataatagg aaattttaa ataagagatt    1560 atcagaaaga gagtttgatc ctgacatcca ctgtggggtt attgatctcg acaccaagaa   1620
gccctgcacc cggtctttga catgcaagac acattcctta acccagcgca gggctgtcca   1680
gggtagaaga aaacgatttg atgtgttatt agccgagcac aaaaacaaaa ccagggaaaa   1740
ggaattgatt cgccatccgg actctcagca accaccgcag cctctcaggg acccgcatcc   1800
cgcccctcct agaacgtcac aggagccgca ccaaaaccct cacggagtga ttccttccga   1860
atcaaagcct tttgtagcta gtaaacctaa acctcacacc cccagtcttc caaggcctcc   1920
aggctgccct gctcagcaag gtgggagtgc ccccattgac cctcctccag tccatgaatc   1980
tccacaccct cccctgcctg ccactgagcc agcttctcgg ttatccagtg aggagggcga   2040
aggcgatgac aaagaagagt ctgttgaaaa actggactgt cattattcag gtcatcatcc   2100
tcagccagca tcttttttgca catttgggag ccggcagata ggaagaggct attacgtgtt   2160
tgactccagg tggaatcgac ttcgctgcgc cctcaacctc atggtggaga agcatctgaa   2220
tgcacagcta tggaagaaaa tcccaccagt gcccagtacc acctcaccca tctccacacg   2280
tattcctcac cggacaaaact ctgtgccgac atcacaatgt ggagtcagct atctggcagc   2340
agccaccgtc tctacatccc cagtcctgct ctcatctacc tgcatctccc caaatagcaa   2400
atcggtacca gctcatggaa ccacactaaa tgcacagcct gctgcttcag gggcgatgga   2460
```

```
tcctgtgtgc agtatgcaat ccagacaagt gtcctcttca tcctcatccc cttccacgcc    2520
ctctggcctt tcctcggttc cttcctcccc catgtccagg aaacctcaga aattgaaatc    2580
cagcaaatct ttgaggccca aggagtcttc tggtaacagc actaactgtc aaaatgccag    2640
tagcagtacc agtggcggct caggaaagaa acgcaaaaac agttcccac tgttggttca     2700 ctcttcctcc tcctcttcct cctcctcctc ttcttctcat tccatggagt cttttaggaa    2760
aaactgtgtg gctcactctg ggcctcccta cccctcaacg gtaacatctt cccatagcat    2820
cggcctcaac tgtgtgacga ataaagcaaa tgcggtgaac gtccggcatg accagtcagg    2880
gaggggcccc cccaccggga gccctgctga atccatcaag aggatgagtg tgatggtgaa    2940
cagcagtgat tctactcttt ctcttgggcc attcattcac cagtccaatg aactgcctgt    3000
caactcccac ggcagttttt cccactcaca cactcctcta gacaaactca taggaaagaa    3060
aagaaagtgc tcacccagct cgagcagcat caacaacagc agcagcaaac ccacaaaggt    3120
tgccaaagtg ccagccgtga acaatgtcca catgaaacac acaggcacca tcccaggggc    3180
acaaggactg atgaacagtt ccctccttca tcagccaaag gcacgtccct gacagctgaa    3240
aatagcacgg ggaggaataa tgcggacact tttgaggaca agttacacct ccactcagca    3300
ctctggactc cacgatgcct ttgagtctgt tttcccaacc tcctgtgggc ctcaagggta    3360
gaaacctgcc gggctgttgt tttaacgagg atttccctga agctatgtct ctagcagtga    3420
gtactcataa aggacactgg atcaagttca gccaccgaat tgcttttatc agtgttaaag    3480
tggtctgaac tgcttgctac caatctgtga agttttgg ttttgtttt gttttttaac        3540 ttgcagtata tcacagagcc actcttcaag tagattggct gggcaaaaga atgttttggc    3600
aagagcgtta ctgtagacct ttctccctcc ttccttttac taccattttt tttaacact     3660 gtcatctgta ggtcactctc cagcagttag gcaccttaac tggagaccag aaaccttcca    3720
gagaacacag ggctgcatcc cgagcaaccc tctgaagaag ggaattaggc tttagatttt    3780
gatagcaatg ttccaggaat gaaatataga tgttagccca agacaccatg acaaaatagc    3840
ccagcctttt gagagtaatt tgggaaaaga agctgtcaga agtttctaac ttacaaactg    3900
gtttgaaatt tttgatgccc agacagcaag tataaatcat tttggaggct tacttttcat    3960
gatacaaaag caattctgtg tgattttttt ttttaagaag aaagaaaatg caagctagtt    4020
ttgagaaagg aaggccaaat tgggtcgggg gagggtggga gtgaggaagt taaaatcact    4080
atagggagaa aaacttttt tcaagatttc caaagagatg aaattttctt aatccttta      4140 agttttcata gtaaacagta tggcagattg ggttggttgt cctacctggt ctattttaa     4200 aagtcacctt ttaaagtgac attattagat acacttaaat gtttccaagg cactctctac    4260
attacccttg ttttctctt tggatactgt cctgggacta agtgtagatt tctgcttcaa     4320
gcacttctgg cattgtgtgt ttttgtatgc actccccttc atgccacttc agatgtttat    4380
ttggatgtgg ttggggacga gagcagacac caaggaaagg gagttggaga gaatgtaagt    4440
cctgacctga aggtcttttg tgatgcatgt ataggattgc cctgacacac accctccttt    4500
cttgggatta taccagccat cttcctgaga gttttggagc cctctaggat atttttttcta   4560 gtaccccacc ccccacccct aaagaaagac cttaatatgt taaaacagca ttgcttggag    4620
aaggtgtcat tgaattccgg gacgagccgg agcctttaaa tgggtgcttc caccactaca    4680
ggctcctgac acgagtaaca ggcactgttg cttagaagaa cacacgaagt tgccgaacac    4740
agggtaaaat ttccaaggcg ctgatcgttg ccctggccag ggcctgatga gagccagtca    4800
```

```
gtacattctt tttttcctac agttcttggg tttcaaactt cagtttcagg gaatttcaag    4860
tcaacaacag gtagaatgaa taaacttggt taccagccta ataatgtgaa ttgctacaga    4920
attattctta ttatgtaaga aaacaaaaac tttatgcaga tactttagct ataaattgat    4980
gtaaaatact gattttttta aaggaaggag agaacagtat cttgttcaat tattatgcaa    5040
tcaatcagta aatgttttta aaatgatact acaggagagc ttagtaagga gagggcatgg    5100
atgggccagt tggcatagt tgggagaaat cagtctggtt tccatcccag tcggggaaga    5160
gagaggtgag agggaatcag aacgtaccta gttgattcct tggtgacaag tgcaatgggg    5220
tatgggtaga atttattttc agagccaaga ggacttgatg gttataaata aagttgcctt    5280
tagcaatgga atttacagat cgatcatgtt gttccgaaag atgtgaatag gatccacaat    5340
aacaagttga ttcagactaa tgtagatatt tagattagca agtattgaac atttgatttc    5400
ttagactgag gttttaaatg aatttcatta tttctcccgg taatacacag agcatcggga    5460
ttaggaaatt agccattttg gattctgtct gccacaaaca gacctattct aaacagtgct    5520
attaaatttt agactgttgt tcaaatattt tattttctcc taaactactt tttatggtga    5580
tgaataatta agaccattta aaacacggga gtacaagtat ttttttgaat taaattaact    5640
tgcaaaaacc aaatttgcag tggttgggtt gtttctagac agactttggt atcaatttaa    5700
aaccaagata atttttatat tcttttccaat agaatttcat gacaactcct gcagttttct    5760
taacctacaa aaaaaaaaa aaagtgctgc aatgatgaac aaagaattat acaaaaccta    5820
cttttgtatc tttattttgg aatttcttgt tctattataa atatggaagt atccctattt    5880
cagaagacat attttgttaa aaatgaattg tacatattta aatatgtatt tttgcacagg    5940 tcttttttc tgatatcctg ttttggtaca attgagatca tctagtattt atttattaat    6000
taataaaagt aaataccttt ttataatttg aagtggttca ctgccaagcc aatagttcta    6060
gaacctgcct cctttacagt tttaagggat gcctctgttc tgtgaaaagt ctttgtccct    6120
tttagtgtct cggagtgga ttcatacaga tgaagtgggc attgcttctt cctggttgcc    6180
tggtttcccg atagactaca tgtaactaag tgacacactg cttttctttt gttagtattt    6240
tatgtgtggg agtatgtgac tgcgtgtgtg tgtgcctgtg cgtgtgtgtg tatactcagc    6300
acatgtatgt tactatgtga tgtggtttaa aactaatgga aaaactgaa agtgcctgaa    6360 actagtttta agcttagaca gaatctcttt aaaaagactt gaatgttcag ttgaactttt    6420
ggagtttgct ttttccacct aaatattgtt tctaaaattt tagggcggaa gttgaaaacc    6480
accaatgctg gtaattttat aaggtatttt aaaattaaga cctcttggtt catagtaatt    6540
caattggtga tggattgcct ggtggcacca agggttacag atcttttgt cagccagcaa    6600 cttacacgat gtgtccgttt tgttattcac tcatgaaata caatttaaaa tatttaaaat    6660
attttgtatt ccaaaaatat aatacaaaga agtacctctg agaacattga aaaaatgta    6720 taatttgaaa aatgtaactt ataagggcag ctgtcttcct gcaagagttc tgttgccaag    6780
gaatttctta atgtcgctca ttctgtccag ggggtttggg gcgattgggc tttgaaaaaa    6840
tattcttaaa agtttgttta gcagaaaata atcacttttta cattttgtgc aaaacatttt    6900
acattttcag ataatttaaa tgagcactac atactgtcag tgtgaatgta gggccttgaa    6960 agcatttgc tttttttttt tttttttttt ttttgagctt ggttataaaa gcaatctcct    7020
gtgttaaaaa cgtgtgaata gtttgataat ttgtacacat aatcaagagc atctcagctg    7080
gactttgtgt tggctgctgt atagaacatg aacaaatgtc aagggataga aaattacttt    7140
ggatatttaa aagagaagaa atatatagtc tatttgtttt gtaacaagtt tctgtaaata    7200
```

```
aaataattta tactatttat aagaaaaaaa aaaaaaaaaa aa                 7242
```

<210> SEQ ID NO 86
<211> LENGTH: 2300
<212> TYPE: DNA
<213> ORGANISM: Homo sapiens

<400> SEQUENCE: 86

```
ggccaggcaa gcctgaatcc tgtccctgcc atctcgccac tgcagctcgg gtccagaaag   60
gcaccatttt gtcgcggctg cccgctctcc caggggagg agggatcttt tttgcatttt   120
ggagcggctg ccaaggaggg aacctgttg ggcatctccc cagacccgct tgtgagcgcc   180
tccgggcgg gcgggcggga ccagacccct cggggcacgg cgtatcttgg cacccggagg   240
cagcggaggc aggcgcagca tcctcgctgg gaactggagc tggagtgagc gcaccgcgcg   300
ggaggagccg ccgcagcctc gcagaacccg agtggaggag gtgacagctc cattgccggg   360
tttttatttt ttttctctcc gcctccccgt ctcctcctca ggctcggacc atggtgcagt   420
cccactggct cccctgcccc cctctcctgt gagactggct gcggggaggg atcatggata   480
cttgtctgcc ggcttctggt tcccacgcaa gtaagcctgc tgtcaatgga ggaggacatt   540
gataccgca aaatcaacaa cagtttcctg cgcgaccaca gctatgcgac cgaagctgac   600
attatctcta cggtagaatt caaccacacg ggagaattac tagcgacagg ggacaagggg   660
ggtcgggttg taatatttca acgagagcag gagagtaaaa atcaggttca tcgtaggggt   720
gaatacaatg tttacagcac attccagagc catgaacccg agttcgatta cctgaagagt   780
ttagaaatag aagaaaaaat caataaaata agatggctcc cccagcagaa tgcagcttac   840
tttcttctgt ctactaatga taaaactgtg aagctgtgga agtcagcga gcgtgataag   900
aggccagaag gctacaatct gaaagatgag gagggccggc tccgggatcc tgccaccatc   960
acaaccctgc gggtgcctgt cctgagaccc atggacctga tggtggaggc cacccccacga   1020
agagtatttg ccaacgcaca cacatatcac atcaactcca tatctgtcaa cagcgactat   1080
gaaacctaca tgtccgctga tgacctgagg attaacctat ggaactttga ataaccaat   1140
caaagtttta atattgtgga cattaagcca gccaacatgg aggagctcac ggaggtgatc   1200
acagcagccg agttccaccc ccatcattgc aacaccttcg tgtacagcag cagcaaaggg   1260
acaatccggc tgtgtgacat gcgggcatct gccctgtgtg acaggcacac caaatttttt   1320
gaagagccgg aagatccaag caacagatca ttttctctg aaattatctc ttcgatttcg   1380
gatgtgaagt tcagccacag tgggaggtat atcatgacca gggactactt gaccgtcaaa   1440
gtctgggatc tcaacatgga aaaccgcccc atcgagactt accaggttca tgactacctc   1500
cgcagcaagc tgtgttccct ctatgaaaat gactgcattt tgataaatt tgagtgtgtg   1560
tggaatgggt cagacagtgt catcatgaca ggctcctaca caacttctt caggatgttc   1620
gacagaaaca ccaagcgtga tgtgacccct gaggcttcga gggaaaacag caagcccgg   1680
gctatcctca aaccccgaaa agtgtgtgtg ggggcaagc ggagaaaga cgagatcagt   1740
gtcgacagtc tggactttag caaaaagatc ttgcatacag cttggcatcc ttcagaaaat   1800
attatagcag tggcggctac aaataaccta tatatattcc aggacaaggt taactaggtg   1860
gacaagttat tacttaataa tctcacatac tgaatactag tcaaacaagt ttttaaatgt   1920
ttctttgggt cttcatttga tgcattgact ttaatttccc tatacaggaa atgattggaa   1980
tagaattaaa aggagtccaa cattcccagc tccccagttc taagaaactt tgtcaaacc   2040
```

```
caataggttt gggacacttc tgtttagaat tgaaagctgc cagctaacag taattcttcc    2100
atagttgact tgaacttctg atgcttttat tgcccagttt tctctggtgg gtccagtgtt    2160
ttgttcctag gtgtctgctg cgataaaatg aggttgtctg tagtatttaa ggagaaaaga    2220
gataagtttt ttttaattaa gcaattccat ttgattgaaa aaaatcaaca aaaaataaac    2280
accgtttact cttagacaaa                                                2300
```

<210> SEQ ID NO 87
<211> LENGTH: 1921
<212> TYPE: DNA
<213> ORGANISM: Homo sapiens

<400> SEQUENCE: 87

```
ggcggaagtg acattatcaa cgcgcgccag gggttcagtg aggtcgggca ggttcgctgt      60
ggcgggcgcc tgggccgccg gctgtttaac ttcgcttccg ctggcccata gtgatctttg     120
cagtgaccca gcatcactgt ttcttggcgt gtgaagataa cccaaggaat tgaggaagtt     180
gctgagaaga gtgtgctgga gatgctctag gaaaaaattg aatagtgaga cgagttccag     240
cgcaagggtt tctggtttgc caagaagaaa gtgaacatca tggatcagaa caacagcctg     300
ccaccttacg ctcagggctt ggcctcccct cagggtgcca tgactcccgg aatccctatc     360
tttagtccaa tgatgcctta tggcactgga ctgaccccac agcctattca gaacaccaat     420
agtctgtcta ttttggaaga gcaacaaagg cagcagcagc aacaacaaca gcagcagcag     480
cagcagcagc agcaacagca acagcagcag cagcagcagc agcagcagca gcagcagcag     540
cagcagcagc agcagcagca acaggcagtg gcagctgcag ccgttcagca gtcaacgtcc     600
cagcaggcaa cacagggaac ctcaggccag gcaccacagc tcttccactc acagactctc     660
acaactgcac ccttgccggg caccactcca ctgtatccct ccccatgac tcccatgacc     720 cccatcactc ctgccacgcc agcttcggag agttctggga ttgtaccgca gctgcaaaat     780
attgtatcca cagtgaatct tggttgtaaa cttgacctaa agaccattgc acttcgtgcc     840
cgaaacgccg aatataatcc caagcggttt gctgcggtaa tcatgaggat aagagagcca     900
cgaaccacgg cactgatttt cagttctggg aaaatggtgt gcacaggagc caagagtgaa     960
gaacagtcca gactggcagc aagaaaatat gctagagttg tacagaagtt gggttttcca    1020
gctaagttct tggacttcaa gattcagaat atggtgggga ctgtgatgt gaagtttcct    1080 ataaggttag aaggccttgt gctcacccac caacaattta gtagttatga gccagagtta    1140
tttcctggtt taatctacag aatgatcaaa cccagaattg ttctcctttat ttttgtttct    1200 ggaaaagttg tattaacagg tgctaaagtc agagcagaaa tttatgaagc atttgaaaac    1260
atctacccta ttctaaaggg attcaggaag acgacgtaat ggctctcatg taccccttgcc    1320 tccccaccc ccttcttttt ttttttttaa acaaatcagt ttgttttggt accttttaaat    1380 ggtggtgttg tgagaagatg gatgttgagt tgcagggtgt ggcaccaggt gatgcccttc    1440
tgtaagtgcc caccgcggga tgccgggaag gggcattatt tgtgcactga aacaccgcg    1500 cagcgtgact gtgagttgct cataccgtgc tgctatctgg gcagcgctgc ccattattt    1560 atatgtagat tttaaacact gctgttgaca agttggtttg agggagaaaa ctttaagtgt    1620
taaagccacc tctataattg attggacttt ttaattttaa tgttttttccc catgaaccac    1680 agttttttata tttctaccag aaaagtaaaa atctttttta aaagtgttgt ttttctaatt    1740
tataactcct aggggttatt tctgtgccag acacattcca cctctccagt attgcaggac    1800
agaatatatg tgttaatgaa aatgaatggc tgtacatatt tttttctttc ttcagagtac    1860
```

| | |
|---|---|
| tctgtacaat aaatgcagtt tataaaagtg ttagattgtt gttaaaaaaa aaaaaaaaa | 1920 |
| a | 1921 |

<210> SEQ ID NO 88
<211> LENGTH: 10661
<212> TYPE: DNA
<213> ORGANISM: Homo sapiens

<400> SEQUENCE: 88

| | |
|---|---|
| cgagatcccg gggagccagc ttgctgggag agcgggacgg tccggagcaa gcccagaggc | 60 |
| agaggaggcg acagagggaa aaagggccga gctagccgct ccagtgctgt acaggagccg | 120 |
| aagggacgca ccacgccagc cccagcccgg ctccagcgac agccaacgcc tcttgcagcg | 180 |
| cggcggcttc gaagccgccg cccggagctg ccctttcctc ttcggtgaag ttttaaaag | 240 |
| ctgctaaaga ctcggaggaa gcaaggaaag tgcctggtag gactgacggc tgcctttgtc | 300 |
| ctcctcctct ccaccccgcc tccccccacc ctgccttccc ccctccccc gtcttctctc | 360 |
| ccgcagctgc ctcagtcggc tactctcagc caacccccct caccacccctt ctccccaccc | 420 |
| gccccccgc cccgtcggc ccagcgctgc cagcccgagt ttgcagagag gtaactccct | 480 |
| ttggctgcga gcgggcgagc tagctgcaca ttgcaaagaa ggctcttagg agccaggcga | 540 |
| ctggggagcg gcttcagcac tgcagccacg acccgcctgg ttaggctgca cgcggagaga | 600 |
| accctctgtt ttccccccact ctctctccac ctcctcctgc cttccccacc ccgagtgcgg | 660 |
| agccagagat caaagatga aaaggcagtc aggtcttcag tagccaaaaa acaaaacaaa | 720 |
| caaaacaaa aagccgaaa taaagaaaa agataataac tcagttctta tttgcaccta | 780 |
| cttcagtgga cactgaattt ggaaggtgga ggattttgtt ttttctttt aagatctggg | 840 |
| catcttttga atctacccctt caagtattaa gagacagact gtgagcctag cagggcagat | 900 |
| cttgtccacc gtgtgtcttc ttctgcacga gactttgagg ctgtcagagc gcttttttgcg | 960 |
| tggttgctcc cgcaagtttc cttctctgga gcttcccgca ggtgggcagc tagctgcagc | 1020 |
| gactaccgca tcatcacagc ctgttgaact cttctgagca agagaagggg aggcggggta | 1080 |
| agggaagtag gtggaagatt cagccaagct caaggatgga agtgcagtta gggctgggaa | 1140 |
| gggtctaccc tcggccgccg tccaagacct accgaggagc tttccagaat ctgttccaga | 1200 |
| gcgtgcgcga agtgatccag aacccgggcc ccaggcaccc agaggccgcg agcgcagcac | 1260 |
| ctcccggcgc cagtttgctg ctgctgcagc agcagcagca gcagcagcag cagcagcagc | 1320 |
| agcagcagca gcagcagcag cagcagcagc agcaagagac tagcccccagg cagcagcagc | 1380 |
| agcagcaggg tgaggatggt tctccccaag cccatcgtag aggccccaca ggctacctgg | 1440 |
| tcctggatga ggaacagcaa ccttcacagc cgcagtcggc cctggagtgc accccgaga | 1500 |
| gaggttgcgt cccagagcct ggagccgccg tggccgccag caagggctg ccgcagcagc | 1560 |
| tgccagcacc tccggacgag gatgactcag ctgccccatc cacgttgtcc ctgctgggcc | 1620 |
| ccactttccc cggcttaagc agctgctccg ctgaccttaa agacatcctg agcgaggcca | 1680 |
| gcaccatgca actccttcag caacagcagc aggaagcagt atccgaaggc agcagcagcg | 1740 |
| ggagagcgag ggaggcctcg ggggctccca cttcctccaa ggacaattac ttaggggca | 1800 |
| cttcgaccat ttctgacaac gccaaggagt tgtgtaaggc agtgtcggtg tccatgggcc | 1860 |
| tgggtgtgga ggcgttggag catctgagtc caggggaaca gcttcggggg gattgcatgt | 1920 |
| acgccccact tttgggagtt ccacccgctg tgcgtcccac tccttgtgcc ccattggccg | 1980 |

```
aatgcaaagg ttctctgcta gacgacagcg caggcaagag cactgaagat actgctgagt    2040
attccccttt caagggaggt tacaccaaag ggctagaagg cgagagccta ggctgctctg    2100
gcagcgctgc agcagggagc tccgggacac ttgaactgcc gtctaccctg tctctctaca    2160
agtccggagc actggacgag gcagctgcgt accagagtcg cgactactac aactttccac    2220
tggctctggc cggaccgccg cccctccgc cgcctcccca tccccacgct cgcatcaagc      2280
tggagaaccc gctggactac ggcagcgcct gggcggctgc ggcggcgcag tgccgctatg    2340
gggacctggc gagcctgcat ggcgcgggtg cagcgggacc cggttctggg tcaccctcag    2400
ccgccgcttc ctcatcctgg cacactctct tcacagccga agaaggccag ttgtatggac    2460
cgtgtggtgg tggtgggggt ggtggcggcg gcggcggcgg cggcggcggc ggcggcggcg    2520
gcggcggcgg cggcgaggcg ggagctgtag cccctacgg ctacactcgg cccctcagg      2580 ggctggcggg ccaggaaagc gacttcaccg cacctgatgt gtggtaccct ggcggcatgg    2640
tgagcagagt gccctatccc agtcccactt gtgtcaaaag cgaaatgggc cctggatgg    2700 atagctactc cggaccttac ggggacatgc gtttggagac tgccagggac catgttttgc    2760
ccattgacta ttactttcca ccccagaaga cctgcctgat ctgtggagat gaagcttctg    2820
ggtgtcacta tggagctctc acatgtggaa gctgcaaggt cttcttcaaa agagccgctg    2880
aagggaaaca gaagtacctg tgcgccagca gaaatgattg cactattgat aaattccgaa    2940
ggaaaaattg tccatcttgt cgtcttcgga atgttatga agcagggatg actctgggag     3000
cccggaagct gaagaaactt ggtaatctga actacagga ggaaggagag gcttccagca     3060
ccaccagccc cactgaggag acaacccaga agctgacagt gtcacacatt gaaggctatg    3120
aatgtcagcc catcttttctg aatgtcctgg aagccattga gccaggtgta gtgtgtgctg   3180
gacacgacaa caaccagccc gactcctttg cagccttgct ctctagcctc aatgaactgg    3240
gagagagaca gcttgtacac gtggtcaagt gggccaaggc cttgcctggc ttccgcaact    3300
tacacgtgga cgaccagatg gctgtcattc agtactcctg gatggggctc atggtgtttg    3360
ccatgggctg gcgatccttc accaatgtca actccaggat gctctacttc gcccctgatc    3420
tggttttcaa tgagtaccgc atgcacaagt cccggatgta cagccagtgt gtccgaatga    3480
ggcacctctc tcaagagttt ggatggctcc aaatcacccc ccaggaattc ctgtgcatga    3540
aagcactgct actcttcagc attattccag tggatgggct gaaaaatcaa aaattctttg    3600
atgaacttcg aatgaactac atcaaggaac tcgatcgtat cattgcatgc aaaagaaaaa    3660
atcccacatc ctgctcaaga cgcttctacc agctcaccaa gctcctggac tccgtgcagc    3720
ctattgcgag agagctgcat cagttcactt ttgacctgct aatcaagtca cacatggtga    3780
gcgtggactt tccggaaatg atggcagaga tcatctctgt gcaagtgccc aagatcctt    3840 ctgggaaagt caagcccatc tatttccaca cccagtgaag cattggaaac cctatttccc    3900 cacccccagct catgccccct ttcagatgtc ttctgcctgt tataactctg cactactcct    3960
ctgcagtgcc ttgggaatt tcctctattg atgtacagtc tgtcatgaac atgttcctga    4020
attctatttg ctgggctttt tttttctctt tctctccttt ctttttcttc ttccctccct    4080
atctaaccct cccatggcac cttcagactt tgcttcccat tgtggctcct atctgtgttt    4140
tgaatggtgt tgtatgcctt taaatctgtg atgatcctca tatggcccag tgtcaagttg    4200
tgcttgttta cagcactact ctgtgccagc cacacaaacg tttacttatc ttatgccacg    4260
ggaagtttag agagctaaga ttatctgggg aaatcaaaac aaaaacaagc aaacaaaaaa    4320
aaaaagcaaa aacaaaacaa aaaataagcc aaaaaccctt gctagtgttt tttcctcaaa    4380
```

```
aataaataaa taaataaata aatacgtaca tacatacaca catacataca aacatataga   4440
aatccccaaa gaggccaata gtgacgagaa ggtgaaaatt gcaggccat ggggagttac    4500
tgattttttc atctcctccc tccacgggag actttatttt ctgccaatgg ctattgccat   4560
tagagggcag agtgacccca gagctgagtt gggcaggggg gtggacagag aggagaggac   4620
aaggagggca atggagcatc agtacctgcc cacagccttg gtccctgggg gctagactgc   4680
tcaactgtgg agcaattcat tatactgaaa atgtgcttgt tgttgaaaat ttgtctgcat   4740
gttaatgcct cacccccaaa ccctttctc tctcactctc tgcctccaac ttcagattga    4800
cttcaatag tttttctaag acctttgaac tgaatgttct cttcagccaa aacttggcga    4860
cttccacaga aaagtctgac cactgagaag aaggagagca gagatttaac cctttgtaag   4920
gccccatttg gatccaggtc tgcttttctca tgtgtgagtc agggaggagc tggagccaga  4980
ggagaagaaa atgatagctt ggctgttctc ctgcttagga cactgactga atagttaaac   5040
tctcactgcc actaccttt cccaccttt aaaagacctg aatgaagttt ctgccaaac      5100
tccgtgaagc cacaagcacc ttatgtcctc ccttcagtgt tttgtgggcc tgaatttcat   5160
cacactgcat ttcagccatg gtcatcaagc ctgtttgctt cttttgggca tgttcacaga   5220
ttctctgtta agagccccca ccaccaagaa ggttagcagg ccaacagctc tgacatctat   5280
ctgtagatgc cagtagtcac aaagatttct taccaactct cagatcgctg gagcccttag   5340
acaaactgga aagaaggcat caaagggatc aggcaagctg ggcgtcttgc ccttgtcccc   5400
cagagatgat accctcccag caagtggaga agttctcact tccttctta gagcagctaa    5460
aggggctacc cagatcaggg ttgaagagaa aactcaatta ccagggtggg aagaatgaag   5520
gcactagaac cagaaaccct gcaaatgctc ttcttgtcac ccagcatatc cacctgcaga   5580
agtcatgaga agagagaagg aacaaagagg agactctgac tactgaatta aaatcttcag   5640
cggcaaagcc taaagccaga tggacaccat ctggtgagtt tactcatcat cctcctctgc   5700
tgctgattct gggctctgac attgcccata ctcactcaga ttccccacct ttgttgctgc   5760
ctcttagtca gagggaggcc aaaccattga gactttctac agaaccatgg cttctttcgg   5820
aaaggtctgg ttggtgtggc tccaatactt tgccacccat gaactcaggg tgtgccctgg   5880
gacactggtt ttatatagtc ttttggcaca cctgtgttct gttgacttcg ttcttcaagc   5940
ccaagtgcaa gggaaaatgt ccacctactt tctcatcttg gcctctgcct ccttacttag   6000
ctcttaatct catctgttga actcaagaaa tcaagggcca gtcatcaagc tgcccatttt   6060
aattgattca ctctgtttgt tgagaggata gtttctgagt gacatgatat gatccacaag   6120
ggtttccttc cctgatttct gcattgatat taatagccaa acgaacttca aaacagcttt   6180
aaataacaag ggagaggga acctaagatg agtaatatgc caatccaaga ctgctggaga   6240
aaactaaagc tgacaggttc cctttttggg gtgggataga catgttctgg ttttctttat   6300
tattacacaa tctggctcat gtacaggatc acttttagct gttttaaaca gaaaaaaata   6360
tccaccactc ttttcagtta cactaggtta cattttaata ggtcctttac atctgttttg   6420
gaatgatttt catcttttgt gatacacaga ttgaattata tcattttcat atctctcctt   6480
gtaaatacta gaagctctcc tttacattc tctatcaaat ttttcatctt tatgggtttc    6540
ccaattgtga ctcttgtctt catgaatata tgttttcat ttgcaaaagc caaaaatcag    6600
tgaaacagca gtgtaattaa agcaacaac tggattactc caaatttcca aatgacaaaa    6660
ctagggaaaa atagcctaca caagccttta ggcctactct ttctgtgctt gggtttgagt   6720
```

```
gaacaaagga gattttagct tggctctgtt ctcccatgga tgaaaggagg aggatttttt    6780
ttttcttttg gccattgatg ttctagccaa tgtaattgac agaagtctca ttttgcatgc    6840
gctctgctct acaaacagag ttggtatggt tggtatactg tactcacctg tgagggactg    6900
gccactcaga cccacttagc tggtgagcta aagatgagg atcactcact ggaaaagtca     6960
caaggaccat ctccaaacaa gttggcagtg ctcgatgtgg acgaagagtg aggaagagaa    7020
aaagaaggag caccagggag aaggctccgt ctgtgctggg cagcagacag ctgccaggat    7080
cacgaactct gtagtcaaag aaaagagtcg tgtggcagtt tcagctctcg ttcattgggc    7140
agctcgccta ggcccagcct ctgagctgac atgggagttg ttggattctt tgtttcatag    7200 cttttttctat gccataggca atattgttgt tcttggaaag tttattattt ttttaactcc    7260
cttactctga gaaagggata ttttgaagga ctgtcatata tctttgaaaa aagaaaatct    7320
gtaatacata tattttttatg tatgttcact ggcactaaaa aatatagaga gcttcattct    7380
gtcctttggg tagttgctga ggtaattgtc caggttgaaa aataatgtgc tgatgctaga    7440
gtccctctct gtccatactc tacttctaaa tacatatagg catacatagc aagttttatt    7500
tgacttgtac tttaagagaa aatatgtcca ccatccacat gatgcacaaa tgagctaaca    7560
ttgagcttca agtagcttct aagtgtttgt ttcattaggc acagcacaga tgtggccttt    7620
ccccccttct ctcccttgat atctggcagg gcataaaggc ccaggccact tcctctgccc    7680
cttcccagcc ctgcaccaaa gctgcatttc aggagactct ctccagacag cccagtaact    7740
acccgagcat ggcccctgca tagccctgga aaaataagag gctgactgtc tacgaattat    7800
cttgtgccag ttgcccaggt gagagggcac tgggccaagg gagtggtttt catgtttgac    7860
ccactacaag gggtcatggg aatcaggaat gccaaagcac cagatcaaat ccaaaactta    7920
aagtcaaaat aagccattca gcatgttcag tttcttggaa aaggaagttt ctaccccctga   7980 tgcctttgta ggcagatctg ttctcaccat taatcttttt gaaaatcttt taaagcagtt    8040
tttaaaaaga gagatgaaag catcacatta tataaccaaa gattacattg tacctgctaa    8100
gataccaaaa ttcataaggg cagggggga gcaagcatta gtgcctcttt gataagctgt     8160
ccaaagacag actaaaggac tctgctggtg actgacttat aagagctttg tgggtttttt    8220
tttccctaat aatatacatg tttagaagaa ttgaaaataa tttcgggaaa atgggattat    8280
gggtccttca ctaagtgatt ttataagcag aactggcttt cctttctct agtagttgct      8340 gagcaaattg ttgaagctcc atcattgcat ggttggaaat ggagctgttc ttagccactg    8400
tgtttgctag tgcccatgtt agcttatctg aagatgtgaa acccttgctg ataagggagc    8460
atttaaagta ctagattttg cactagaggg acagcaggca gaaatcctta tttctgccca    8520
ctttggatgg cacaaaaagt tatctgcagt tgaaggcaga aagttgaaat acattgtaaa    8580
tgaatatttg tatccatgtt tcaaaattga aatatatata tatatatata tatatatata    8640
tatatatata tagtgtgtgt gtgtgttctg atagctttaa ctttctctgc atctttatat    8700
ttggttccag atcacacctg atgccatgta cttgtgagag aggatgcagt tttgttttgg    8760
aagctctctc agaacaaaca agacacctgg attgatcagt taactaaaag ttttctcccc    8820
tattgggttt gacccacagg tcctgtgaag gagcagaggg ataaaaagag tagaggacat    8880
gatacattgt actttactag ttcaagacag atgaatgtgg aaagcataaa aactcaatgg    8940
aactgactga gatttaccac agggaaggcc caaacttggg gccaaaagcc tacccaagtg    9000
attgaccagt ggccccctaa tgggacctga gctgttggaa gaagagaact gttccttggt    9060
cttcaccatc cttgtgagag aagggcagtt tcctgcattg gaacctggag caagcgctct    9120
```

```
atctttcaca caaattccct cacctgagat tgaggtgctc ttgttactgg gtgtctgtgt      9180
gctgtaattc tggttttgga tatgttctgt aaagattttg acaaatgaaa atgtgttttt      9240
ctctgttaaa acttgtcaga gtactagaag ttgtatctct gtaggtgcag gtccatttct      9300
gcccacaggt agggtgtttt tctttgatta agagattgac acttctgttg cctaggacct      9360
cccaactcaa ccatttctag gtgaaggcag aaaaatccac attagttact cctcttcaga      9420
catttcagct gagataacaa atcttttgga attttttcac ccatagaaag agtggtagat      9480
atttgaattt agcaggtgga gtttcatagt aaaaacagct tttgactcag ctttgattta      9540
tcctcatttg atttggccag aaagtaggta atatgcattg atttggcttct gattccaatt     9600
```

```
ccctccgatc tggatagctt ggacgggcgg agccttaatg atgatggcag cagcgaccct    600
agggatatcg accaggacaa ccgaagcacg tcccccagta tctacagccc tggaagtgtg    660
gagaatgact ctgactcatc ttctggcctg tcccagggcc cagcccgccc ctaccaccca    720
cctccactct ttcctccttc ccctcaaccg ccagacagca cccctcgaca gccagaggct    780
agctttgaac cccatccttc tgtgacaccc actggatatc atgctcccat ggagcccccc    840
acatctcgaa tgttccaggc tcctcctggg cccctcccc ctcacccaca gctctatcct    900
gggggcactg gtggagtttt gtctggaccc ccaatgggtc caagggggg agggctgcc     960 tcatcagtgg ggggccctaa tgggggtaag cagcaccccc cacccactac tcccatttca    1020
gtatcaagct ctgggctag tggtgctccc ccaacaaagc cgcctaccac tccagtgggt    1080
ggtgggaacc taccttctgc tccaccacca gccaacttcc cccatgtgac accgaacctg    1140
cctcccccac ctgccctgag acccctcaac aatgcatcag cctctccccc tggcctgggg    1200
gcccaaccac tacctggtca tctgccctct ccccacgcca tgggacaggg tatgggtgga    1260
cttcctcctg gcccagagaa gggcccaact ctggctcctt cacccactc tctgcctcct    1320 gcttcctctt ctgctccagc gcccccatg aggtttcctt attcatcctc tagtagtagc    1380
tctgcagcag cctcctcttc cagttcttcc tcctcttcct ctgcctcccc cttcccagct    1440
tcccaggcat tgcccagcta ccccccactct ttccctcccc caacaagcct ctctgtctcc    1500
aatcagcccc ccaagtatac tcagccttct ctcccatccc aggctgtgtg gagccagggt    1560 ccccccaccac ctcctcccta tggccgcctc ttagccaaca gcaatgccca tccaggcccc    1620
ttccctccct ctactggggc ccagtccacc gcccacccac cagtctcaac acatcaccat    1680
caccaccagc aacagcaaca gcagcagcag cagcagcagc agcagcagca gcagcagcag    1740
cagcatcacg gaaactctgg gcccctcct cctggagcat ttccccaccc actggagggc    1800
ggtagctccc accacgcaca cccttacgcc atgtctccct ccctggggtc tctgaggccc    1860
tacccaccag ggccagcaca cctgccccca cctcacagcc aggtgtccta cagccaagca    1920
ggccccaatg gccctccagt tctcttcctct tccaactctt cctcttccac ttctcaaggg    1980
tcctacccat gttcacaccc ctcccccttcc cagggccctc aaggggcgcc ctacccttc     2040 ccaccggtgc ctacggtcac cacctcttcg gctaccctt ccacggtcat tgccaccgtg    2100
gcttcctcgc cagcaggcta caaaacggcc tccccacctg gcccccacc gtacggaaag    2160 agagccccgt cccccggggc ctacaagaca gccacccccac ccggatacaa acccgggtcg    2220 cctcctcct tccgaacggg gaccccaccg ggctatcgag gaacctcgcc acctgcaggc    2280
ccagggacct tcaagccggg ctcgcccacc gtgggacctg ggccctgcc acctgcgggg    2340 ccctcaggcc tgccatcgct gccaccacca cctgcggccc ctgcctcagg gccgcccctg    2400
agcgccacgc agatcaaaca ggagccggct gaggagtatg agaccccga gagcccggtg    2460 cccccagccc gcagccctc gcccctccc aaggtggtag atgtacccag ccatgccagt    2520
cagtctgcca ggttcaacaa acacctggat cgcggcttca actcgtgcgc gcgcagcgac    2580
ctgtacttcg tgccactgga gggctccaag ctggccaaga gcgggccga cctggtggag    2640 aaggtgcggc gcgaggccga gcagcgcgcg gcgaagaaa aggagcgcga gcgcgagcgg    2700
gaacgcgaga aagagcgcga gcgcgagaag gagcgcgagc ttgaacgcag cgtgaagttg    2760
gctcaggagg gccgtgctcc ggtggaatgc ccatctctgg gcccagtgcc ccatcgccct    2820
ccatttgaac cgggcagtgc ggtggctaca gtgccccct acctgggtcc tgacactcca    2880
gccttgcgca ctctcagtga atatgcccgg cctcatgtca tgtctcctgg caatcgcaac    2940
```

-continued

```
catccattct acgtgccct gggggcagtg gacccggggc tcctgggtta caatgtcccg    3000
gccctgtaca gcagtgatcc agctgccgg gagagggaac gggaagcccg tgaacgagac    3060
ctccgtgacc gcctcaagcc tggctttgag gtgaagccta gtgagctgga acccctacat   3120
ggggtccctg ggccgggctt ggatcccttt ccccgacatg ggggcctggc tctgcagcct   3180
ggcccacctg gcctgcaccc tttcccttt catccgagcc tggggcccct ggagcgagaa    3240
cgtctagcgc tggcagctgg gccagccctg cggcctgaca tgtcctatgc tgagcggctg   3300
gcagctgaga ggcagcacgc agaaagggtg gcggccctgg gcaatgaccc actggcccgg   3360
ctgcagatgc tcaatgtgac tccccatcac caccagcact cccacatcca ctcgcacctg   3420
cacctgcacc agcaagatgc tatccatgca gcctctgcct cggtgcaccc tctcattgac   3480
cccctggcct cagggtctca ccttacccgg atccctacc cagctggaac tctccctaac    3540
cccctgcttc ctcaccctct gcacgagaac gaagttcttc gtcaccagct ctttgctgcc   3600
ccttaccggg acctgccggc ctccctttct gccccgatgt cagcagctca tcagctgcag   3660
gccatgcacg cacagtcagc tgagctgcag cgcttggcgc tggaacagca gcagtggctg   3720
catgcccatc acccgctgca cagtgtgccg ctgcctgccc aggaggacta ctacagtcac   3780
ctgaagaagg aaagcgacaa gccactgtag aacctgcgat caagagagca ccatggctcc   3840
tacattggac cttggagcac ccccaccctc ccccaccgt gcccttggcc tgccacccag    3900
agccaagagg gtgctgctca gttgcagggc ctccgcagct ggacagagag tggggaggg    3960 agggacagac agaaggccaa ggcccgatgt ggtgtgcaga ggtggggagg tggcgaggat   4020
ggggacagaa agcgcacaga atcttggacc aggtctctct tccttgtccc ccctgctttt   4080
ctcctccccc atgcccaacc cctgtggccg ccgcccctcc cctgcccgt tggtgtgatt    4140 atttcatctg ttagatgtgg ctgttttgcg tagcatcgtg tgccacccct gccctcccc    4200 gatccctgtg tgcgcgcccc ctctgcaatg tatgccccctt gccccttccc cacactaata   4260
atttatatat ataaatatct atatgacgct cttaaaaaaa catcccaacc aaaaccaacc   4320
aaacaaaaac atcctcacaa ctccccagga aaaaaaaaaa aaaaaaa              4367
```

<210> SEQ ID NO 90
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)

```
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 90
nugnugnugn ugnugnugnu g                                              21

<210> SEQ ID NO 91
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine

<400> SEQUENCE: 91
nugcugcugc ugcugcugcu g                                              21

<210> SEQ ID NO 92
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine

<400> SEQUENCE: 92
cugnugcugn ugcugnugcu g                                              21

<210> SEQ ID NO 93
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 93
nugcugnugc ugnugcugnu g                                              21
```

```
<210> SEQ ID NO 94
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 94
cugcugnugn ugnugcugcu g                                    21

<210> SEQ ID NO 95
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (10)..(10)
<223> OTHER INFORMATION: n is 5-methylcytosine

<400> SEQUENCE: 95
cugcugcugn ugcugcugcu g                                    21

<210> SEQ ID NO 96
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 96
nugcugcugc ugcugcugnu g                                    21

<210> SEQ ID NO 97
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
```

```
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 97
cngcngcngc ngcngcngcn g                                              21

<210> SEQ ID NO 98
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil

<400> SEQUENCE: 98
cngcugcugc ugcugcugcu g                                              21

<210> SEQ ID NO 99
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil

<400> SEQUENCE: 99
cugcngcugc ngcugcngcu g                                              21

<210> SEQ ID NO 100
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
```

```
<220> FEATURE:
<221> NAME/KEY: misc_feature
<222> LOCATION: (20)..(20)
<223> OTHER INFORMATION: n is 5-methyluracil

<400> SEQUENCE: 100
cngcugcngc ugcngcugcn g                                              21

<210> SEQ ID NO 101
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil

<400> SEQUENCE: 101
cugcugcngc ngcngcugcu g                                              21

<210> SEQ ID NO 102
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 102
cngcugcugc ugcugcugcn g                                              21

<210> SEQ ID NO 103
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil

<400> SEQUENCE: 103
cugcugcngc ugcngcugcu g                                              21

<210> SEQ ID NO 104
<211> LENGTH: 21
<212> TYPE: RNA
<213> ORGANISM: Artificial
<220> FEATURE:
```

```
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methyluracil

<400> SEQUENCE: 104
nngnngnngn ngnngnngnn g                                     21

<210> SEQ ID NO 105
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
```

<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methyluracil

<400> SEQUENCE: 105
cugcugnngn ngnngcugcu g                                               21

<210> SEQ ID NO 106
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine

<400> SEQUENCE: 106
nngcugcugc ugcugcugnn g                                               21

<210> SEQ ID NO 107
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:

```
<221> NAME/KEY: misc_feature
<222> LOCATION: (19)..(19)
<223> OTHER INFORMATION: n is 5-methylcytosine

<400> SEQUENCE: 107
nugnugnugn ugnugnugnu g                                              21

<210> SEQ ID NO 108
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 108
nugcugnugc ugnugcugnu g                                              21

<210> SEQ ID NO 109
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine

<400> SEQUENCE: 109
nugnugnugn ugnugnugnu gnug                                           24
```

<210> SEQ ID NO 110
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil

<400> SEQUENCE: 110
cngcngcngc ngcngcngcn gcng                                          24

<210> SEQ ID NO 111
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)

```
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 111
nugnugnugn ugnugnugnu gnugnug                                              27

<210> SEQ ID NO 112
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil

<400> SEQUENCE: 112
cngcngcngc ngcngcngcn gcngcng                                              27

<210> SEQ ID NO 113
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
```

```
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine

<400> SEQUENCE: 113
nugnugnugn ugnugnugnu gnugnugnug                                30

<210> SEQ ID NO 114
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
```

```
<221> NAME/KEY: misc_feature
<222> LOCATION: (29)..(29)
<223> OTHER INFORMATION: n is 5-methyluracil

<400> SEQUENCE: 114
cngcngcngc ngcngcngcn gcngcngcng                                    30

<210> SEQ ID NO 115
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (31)..(31)
<223> OTHER INFORMATION: n is 5-methylcytosine

<400> SEQUENCE: 115
nugnugnugn ugnugnugnu gnugnugnug nug                                33

<210> SEQ ID NO 116
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
```

```
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil
<220> FEATURE:
<221> NAME/KEY: misc_feature
<222> LOCATION: (32)..(32)
<223> OTHER INFORMATION: n is 5-methyluracil

<400> SEQUENCE: 116
cngcngcngc ngcngcngcn gcngcngcng cng                                    33

<210> SEQ ID NO 117
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
```

```
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (31)..(31)
<223> OTHER INFORMATION: n is 5-methylcytosine
<220> FEATURE:
<221> NAME/KEY: misc_feature
<222> LOCATION: (34)..(34)
<223> OTHER INFORMATION: n is 5-methylcytosine

<400> SEQUENCE: 117
nugnugnugn ugnugnugnu gnugnugnug nugnug                            36

<210> SEQ ID NO 118
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil
<220> FEATURE:
<221> NAME/KEY: misc_feature
<222> LOCATION: (32)..(32)
<223> OTHER INFORMATION: n is 5-methyluracil
<220> FEATURE:
<221> NAME/KEY: misc_feature
<222> LOCATION: (35)..(35)
<223> OTHER INFORMATION: n is 5-methyluracil

<400> SEQUENCE: 118
```
cngcngcngc ngcngcngcn gcngcngcng cngcng        36

<210> SEQ ID NO 119
<211> LENGTH: 12
<212> TYPE: RNA
<213> ORGANISM: Artificial
<220> FEATURE:
<223> OTHER INFORMATION: Oligonculeotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 119
ngnngnngnn gn        12

<210> SEQ ID NO 120
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine

<400> SEQUENCE: 120
ngcngcngcn gc        12

<210> SEQ ID NO 121
<211> LENGTH: 15
<212> TYPE: RNA

```
<213> ORGANISM: Artificial
<220> FEATURE:
<223> OTHER INFORMATION: Oligoncleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 121
ngnngnngnn gnngn                                                15

<210> SEQ ID NO 122
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 122
ngcngcngcn gcngc                                                15
```

```
<210> SEQ ID NO 123
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 123
ngnngnngnn gnngnngn                                                   18

<210> SEQ ID NO 124
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
```

```
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine

<400> SEQUENCE: 124
ngcngcngcn gcngcngc                                              18

<210> SEQ ID NO 125
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
```

```
<222> LOCATION: (21)..(21)
<223> OTHER INFORMATION: n is 5-methylcytosine

<400> SEQUENCE: 125
ngnngnngnn gnngnngnng n                                              21

<210> SEQ ID NO 126
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 126
ngcngcngcn gcngcngcng c                                              21

<210> SEQ ID NO 127
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
```

```
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 127
ngnngnngnn gnngnngnng nngn                                              24

<210> SEQ ID NO 128
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
```

```
<220> FEATURE:
<221> NAME/KEY: misc_feature
<222> LOCATION: (22)..(22)
<223> OTHER INFORMATION: n is 5-methylcytosine

<400> SEQUENCE: 128
ngcngcngcn gcngcngcng cngc                                              24

<210> SEQ ID NO 129
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
```

```
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine

<400> SEQUENCE: 129
ngnngnngnn gnngnngnng nngnngn                                             27

<210> SEQ ID NO 130
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is a, c, g, or u
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 130
ngcngcngcn gcngcngcng cngcngc                                             27

<210> SEQ ID NO 131
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
```

```
<222> LOCATION: (4)..(4)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine

<400> SEQUENCE: 131
ngnngnngnn gnngnngnng nngnngnngn                              30

<210> SEQ ID NO 132
<211> LENGTH: 30
<212> TYPE: RNA
```

<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine

<400> SEQUENCE: 132
ngcngcngcn gcngcngcng cngcngcngc                                     30

<210> SEQ ID NO 133
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine

```
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine

<400> SEQUENCE: 133
nngnngnngn ng                                                            12

<210> SEQ ID NO 134
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine

<400> SEQUENCE: 134
cngcngcngc ng                                                            12

<210> SEQ ID NO 135
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
```

```
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine

<400> SEQUENCE: 135
nngnngnngn ngnng                                                     15

<210> SEQ ID NO 136
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine

<400> SEQUENCE: 136
cngcngcngc ngcng                                                     15

<210> SEQ ID NO 137
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
```

```
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 137
nngnngnngn ngnngnng                                              18

<210> SEQ ID NO 138
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 138
cngcngcngc ngcngcng                                              18

<210> SEQ ID NO 139
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
```

```
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine

<400> SEQUENCE: 139
nngnngnngn ngnngnngnn g                                        21

<210> SEQ ID NO 140
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
```

-continued

```
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine

<400> SEQUENCE: 140
cngcngcngc ngcngcngcn g                                              21

<210> SEQ ID NO 141
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
```

```
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine

<400> SEQUENCE: 141
nngnngnngn ngnngnngnn gnng                                                 24

<210> SEQ ID NO 142
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine

<400> SEQUENCE: 142
cngcngcngc ngcngcngcn gcng                                                 24

<210> SEQ ID NO 143
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
```

```
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine

<400> SEQUENCE: 143
nngnngnngn ngnngnngnn gnngnng                                           27

<210> SEQ ID NO 144
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
```

```
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (20)..(20)
<223> OTHER INFORMATION: n is a, c, g, or u
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine

<400> SEQUENCE: 144
cngcngcngc ngcngcngcn gcngcng                                          27

<210> SEQ ID NO 145
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
```

```
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (23)..(23)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine

<400> SEQUENCE: 145
nngnngnngn ngnngnngnn gnngnngnng                                         30

<210> SEQ ID NO 146
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (8)..(8)
<223> OTHER INFORMATION: n is 5-methylcytosine
<220> FEATURE:
<221> NAME/KEY: misc_feature
<222> LOCATION: (11)..(11)
<223> OTHER INFORMATION: n is 5-methylcytosine
<220> FEATURE:
<221> NAME/KEY: misc_feature
<222> LOCATION: (14)..(14)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (20)..(20)
<223> OTHER INFORMATION: n is 5-methylcytosine
<220> FEATURE:
<221> NAME/KEY: misc_feature
<222> LOCATION: (23)..(23)
```

```
<223> OTHER INFORMATION: n is 5-methylcytosine
<220> FEATURE:
<221> NAME/KEY: misc_feature
<222> LOCATION: (26)..(26)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine

<400> SEQUENCE: 146
cngcngcngc ngcngcngcn gcngcngcng                                    30

<210> SEQ ID NO 147
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 147
uunuunuunu un                                                       12

<210> SEQ ID NO 148
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
```

```
<222> LOCATION: (11)..(11)
<223> OTHER INFORMATION: n is 5-methyluracil

<400> SEQUENCE: 148
nncnncnncn nc                                                              12

<210> SEQ ID NO 149
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 149
uunuunuunu unuun                                                           15

<210> SEQ ID NO 150
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
```

```
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil

<400> SEQUENCE: 150
nncnncnncn ncnnc                                                        15

<210> SEQ ID NO 151
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is a, c, g, or u
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 151
uunuunuunu unuunuun                                                     18

<210> SEQ ID NO 152
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
```

```
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil

<400> SEQUENCE: 152
nncnncnncn ncnncnnc                                              18

<210> SEQ ID NO 153
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 153
uunuunuunu unuunuunuu n                                          21

<210> SEQ ID NO 154
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
```

```
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil

<400> SEQUENCE: 154
nncnnncnnc ncnncnncnn c                                      21

<210> SEQ ID NO 155
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
```

```
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine

<400> SEQUENCE: 155 nnnnnnnnn nnnnnnnnn n                                          21

<210> SEQ ID NO 156
<211> LENGTH: 21
<212> TYPE: RNA
```

```
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine

<400> SEQUENCE: 156
nnnuucuucu ucuucuucnn n                                              21

<210> SEQ ID NO 157
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methyluracil
```

```
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (21)..(21)
<223> OTHER INFORMATION: n is 5-methylcytosine

<400> SEQUENCE: 157
nnnuucnnnu ucnnnuucnn n                                              21

<210> SEQ ID NO 158
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 158
uunuunuunu unuunuunuu nuun                                           24

<210> SEQ ID NO 159
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
```

<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil

<400> SEQUENCE: 159
nncnncnncn ncnncnncnn cnnc                                      24

<210> SEQ ID NO 160
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature

```
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine

<400> SEQUENCE: 160
uunuunuunu unuunuunuu nuunuun                                      27

<210> SEQ ID NO 161
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is a, c, g, or u
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
```

```
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil

<400> SEQUENCE: 161
nncnncnncn ncnncnncnn cnncnnc                                27

<210> SEQ ID NO 162
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine

<400> SEQUENCE: 162
uunuunuunu unuunuunuu nuunuunuun                             30
```

```
<210> SEQ ID NO 163
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
```

```
<223> OTHER INFORMATION: n is 5-methyluracil
<220> FEATURE:
<221> NAME/KEY: misc_feature
<222> LOCATION: (28)..(28)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil

<400> SEQUENCE: 163
nncnncnncn ncnncnncnn cnncnncnnc                                30

<210> SEQ ID NO 164
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine
<220> FEATURE:
<221> NAME/KEY: misc_feature
<222> LOCATION: (33)..(33)
<223> OTHER INFORMATION: n is 5-methylcytosine

<400> SEQUENCE: 164
uunuunuunu unuunuunuu nuunuunuun uun                            33

<210> SEQ ID NO 165
<211> LENGTH: 33
<212> TYPE: RNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (28)..(28)
<223> OTHER INFORMATION: n is 5-methyluracil
<220> FEATURE:
<221> NAME/KEY: misc_feature
<222> LOCATION: (29)..(29)
<223> OTHER INFORMATION: n is 5-methyluracil
<220> FEATURE:
```

<221> NAME/KEY: misc_feature
<222> LOCATION: (31)..(31)
<223> OTHER INFORMATION: n is 5-methyluracil
<220> FEATURE:
<221> NAME/KEY: misc_feature
<222> LOCATION: (32)..(32)
<223> OTHER INFORMATION: n is 5-methyluracil

<400> SEQUENCE: 165 nncnncncn ncnncnncnn cnncnncnnc nnc          33

<210> SEQ ID NO 166
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine
<220> FEATURE:
<221> NAME/KEY: misc_feature
<222> LOCATION: (33)..(33)
<223> OTHER INFORMATION: n is 5-methylcytosine
<220> FEATURE:
<221> NAME/KEY: misc_feature
<222> LOCATION: (36)..(36)
<223> OTHER INFORMATION: n is 5-methylcytosine

<400> SEQUENCE: 166
uunuunuunu unuunuunuu nuunuunuun uunuun          36

<210> SEQ ID NO 167
<211> LENGTH: 36
<212> TYPE: RNA
<213> ORGANISM: Artificial
<220> FEATURE:
<223> OTHER INFORMATION: Oligonucleotide -continued

```
<220> FEATURE:
<221> NAME/KEY: misc_feature
<222> LOCATION: (1)..(1)
<223> OTHER INFORMATION: n is 5-methyluracil
<220> FEATURE:
<221> NAME/KEY: misc_feature
<222> LOCATION: (2)..(2)
<223> OTHER INFORMATION: n is 5-methyluracil
<220> FEATURE:
<221> NAME/KEY: misc_feature
<222> LOCATION: (4)..(4)
<223> OTHER INFORMATION: n is 5-methyluracil
<220> FEATURE:
<221> NAME/KEY: misc_feature
<222> LOCATION: (5)..(5)
<223> OTHER INFORMATION: n is 5-methyluracil
<220> FEATURE:
<221> NAME/KEY: misc_feature
<222> LOCATION: (7)..(7)
<223> OTHER INFORMATION: n is 5-methyluracil
<220> FEATURE:
<221> NAME/KEY: misc_feature
<222> LOCATION: (8)..(8)
<223> OTHER INFORMATION: n is 5-methyluracil
<220> FEATURE:
<221> NAME/KEY: misc_feature
<222> LOCATION: (10)..(10)
<223> OTHER INFORMATION: n is 5-methyluracil
<220> FEATURE:
<221> NAME/KEY: misc_feature
<222> LOCATION: (11)..(11)
<223> OTHER INFORMATION: n is 5-methyluracil
<220> FEATURE:
<221> NAME/KEY: misc_feature
<222> LOCATION: (13)..(13)
<223> OTHER INFORMATION: n is 5-methyluracil
<220> FEATURE:
<221> NAME/KEY: misc_feature
<222> LOCATION: (14)..(14)
<223> OTHER INFORMATION: n is 5-methyluracil
<220> FEATURE:
<221> NAME/KEY: misc_feature
<222> LOCATION: (16)..(16)
<223> OTHER INFORMATION: n is 5-methyluracil
<220> FEATURE:
<221> NAME/KEY: misc_feature
<222> LOCATION: (17)..(17)
<223> OTHER INFORMATION: n is 5-methyluracil
<220> FEATURE:
<221> NAME/KEY: misc_feature
<222> LOCATION: (19)..(19)
<223> OTHER INFORMATION: n is 5-methyluracil
<220> FEATURE:
<221> NAME/KEY: misc_feature
<222> LOCATION: (20)..(20)
<223> OTHER INFORMATION: n is 5-methyluracil
<220> FEATURE:
<221> NAME/KEY: misc_feature
<222> LOCATION: (22)..(22)
<223> OTHER INFORMATION: n is 5-methyluracil
<220> FEATURE:
<221> NAME/KEY: misc_feature
<222> LOCATION: (23)..(23)
<223> OTHER INFORMATION: n is 5-methyluracil
<220> FEATURE:
<221> NAME/KEY: misc_feature
<222> LOCATION: (25)..(25)
<223> OTHER INFORMATION: n is 5-methyluracil
<220> FEATURE:
<221> NAME/KEY: misc_feature
<222> LOCATION: (26)..(26)
<223> OTHER INFORMATION: n is 5-methyluracil
<220> FEATURE:
<221> NAME/KEY: misc_feature
<222> LOCATION: (28)..(28)
<223> OTHER INFORMATION: n is 5-methyluracil
<220> FEATURE:
<221> NAME/KEY: misc_feature
<222> LOCATION: (29)..(29)
```

```
<223> OTHER INFORMATION: n is 5-methyluracil
<220> FEATURE:
<221> NAME/KEY: misc_feature
<222> LOCATION: (31)..(31)
<223> OTHER INFORMATION: n is 5-methyluracil
<220> FEATURE:
<221> NAME/KEY: misc_feature
<222> LOCATION: (32)..(32)
<223> OTHER INFORMATION: n is 5-methyluracil
<220> FEATURE:
<221> NAME/KEY: misc_feature
<222> LOCATION: (34)..(34)
<223> OTHER INFORMATION: n is 5-methyluracil
<220> FEATURE:
<221> NAME/KEY: misc_feature
<222> LOCATION: (35)..(35)
<223> OTHER INFORMATION: n is 5-methyluracil

<400> SEQUENCE: 167
nncnncnncn ncnncnncnn cnncnncnnc nncnnc                                36

<210> SEQ ID NO 168
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 168
ggnggnggng gn                                                          12

<210> SEQ ID NO 169
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 169
```
ggnggnggng gnggn                                                    15

<210> SEQ ID NO 170
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 170
ggnggnggng gnggnggn                                                 18

<210> SEQ ID NO 171
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 171
ggnggnggng gnggnggngg n                                             21

```
<210> SEQ ID NO 172
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 172
ggnggcggcg gcggcggcgg n                                               21

<210> SEQ ID NO 173
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 173
ggnggcggng gcggnggcgg n                                               21

<210> SEQ ID NO 174
<211> LENGTH: 21
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine

<400> SEQUENCE: 174
ggcggcggng gnggnggcgg c                                               21

<210> SEQ ID NO 175
<211> LENGTH: 24
<212> TYPE: RNA
<213> ORGANISM: Artificial
<220> FEATURE:
<223> OTHER INFORMATION: Oligonucleotide
```

```
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 175
ggnggnggng gnggnggngg nggn                                              24

<210> SEQ ID NO 176
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
```

<223> OTHER INFORMATION: n is 5-methylcytosine

<400> SEQUENCE: 176
ggnggnggng gnggnggngg nggnggn                              27

<210> SEQ ID NO 177
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is 5-methylcytosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (15)..(15)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine
<220> FEATURE:
<221> NAME/KEY: misc_feature
<222> LOCATION: (27)..(27)
<223> OTHER INFORMATION: n is 5-methylcytosine
<220> FEATURE:
<221> NAME/KEY: misc_feature
<222> LOCATION: (30)..(30)
<223> OTHER INFORMATION: n is 5-methylcytosine

<400> SEQUENCE: 177
ggnggnggng gnggnggngg nggnggnggn                           30

<210> SEQ ID NO 178
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine

<400> SEQUENCE: 178
nggnggnggn gg                                                        12

<210> SEQ ID NO 179
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 179
nggnggnggn ggngg                                                     15

<210> SEQ ID NO 180
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine

<400> SEQUENCE: 180
nggnggnggn ggnggngg                                                  18

<210> SEQ ID NO 181
<211> LENGTH: 21
<212> TYPE: RNA

```
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine

<400> SEQUENCE: 181
nggnggnggn ggnggnggng g                                    21

<210> SEQ ID NO 182
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine

<400> SEQUENCE: 182
nggnggnggn ggnggnggng gngg                                 24
```

<210> SEQ ID NO 183
<211> LENGTH: 27
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 183
nggnggnggn ggnggnggng gnggngg                                27

<210> SEQ ID NO 184
<211> LENGTH: 30
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)

```
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (28)..(28)
<223> OTHER INFORMATION: n is 5-methylcytosine

<400> SEQUENCE: 184
nggnggnggn ggnggnggng gnggnggngg                                    30

<210> SEQ ID NO 185
<211> LENGTH: 15
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

<400> SEQUENCE: 185
ngnnungnnu ngnnu                                                    15

<210> SEQ ID NO 186
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
```

```
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine

<400> SEQUENCE: 186
ngnnungnnu ngnnungnnu                                           20

<210> SEQ ID NO 187
<211> LENGTH: 20
<212> TYPE: RNA
<213> ORGANISM: Artificial
<220> FEATURE:
<223> OTHER INFORMATION: Oligonucelotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
```

```
<221> NAME/KEY: misc_feature
<222> LOCATION: (19)..(19)
<223> OTHER INFORMATION: n is 2,6-diaminopurine

<400> SEQUENCE: 187
ngnnuagaau agaaungnnu                                              20

<210> SEQ ID NO 188
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

<400> SEQUENCE: 188
ngnnuagaau ngnnuagaau                                              20

<210> SEQ ID NO 189
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine

<400> SEQUENCE: 189
ngaauagnnu ngaauagnnu                                              20
```

<210> SEQ ID NO 190
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 2,6-diaminopurine
<220> FEATURE:
<221> NAME/KEY: misc_feature
<222> LOCATION: (23)..(23)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 2,6-diaminopurine

<400> SEQUENCE: 190
ngnnungnnu ngnnungnnu ngnnu                                 25

<210> SEQ ID NO 191
<211> LENGTH: 30
<212> TYPE: RNA
<213> ORGANISM: Artificial
<220> FEATURE:

```
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 2,6-diaminopurine
<220> FEATURE:
<221> NAME/KEY: misc_feature
<222> LOCATION: (23)..(23)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine
<220> FEATURE:
<221> NAME/KEY: misc_feature
<222> LOCATION: (28)..(28)
<223> OTHER INFORMATION: n is 2,6-diaminopurine
<220> FEATURE:
<221> NAME/KEY: misc_feature
<222> LOCATION: (29)..(29)
<223> OTHER INFORMATION: n is 2,6-diaminopurine

<400> SEQUENCE: 191
ngnnungnnu ngnnungnnu ngnnungnnu                                        30
```

```
<210> SEQ ID NO 192
<211> LENGTH: 35
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 2,6-diaminopurine
<220> FEATURE:
<221> NAME/KEY: misc_feature
<222> LOCATION: (3)..(3)
<223> OTHER INFORMATION: n is 2,6-diaminopurine
<220> FEATURE:
<221> NAME/KEY: misc_feature
<222> LOCATION: (4)..(4)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (8)..(8)
<223> OTHER INFORMATION: n is 2,6-diaminopurine
<220> FEATURE:
<221> NAME/KEY: misc_feature
<222> LOCATION: (9)..(9)
<223> OTHER INFORMATION: n is 2,6-diaminopurine
<220> FEATURE:
<221> NAME/KEY: misc_feature
<222> LOCATION: (11)..(11)
<223> OTHER INFORMATION: n is 2,6-diaminopurine
<220> FEATURE:
<221> NAME/KEY: misc_feature
<222> LOCATION: (13)..(13)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (16)..(16)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (19)..(19)
<223> OTHER INFORMATION: n is 2,6-diaminopurine
<220> FEATURE:
<221> NAME/KEY: misc_feature
<222> LOCATION: (21)..(21)
<223> OTHER INFORMATION: n is 2,6-diaminopurine
<220> FEATURE:
<221> NAME/KEY: misc_feature
<222> LOCATION: (23)..(23)
<223> OTHER INFORMATION: n is 2,6-diaminopurine
<220> FEATURE:
<221> NAME/KEY: misc_feature
<222> LOCATION: (24)..(24)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine
<220> FEATURE:
<221> NAME/KEY: misc_feature
<222> LOCATION: (28)..(28)
<223> OTHER INFORMATION: n is 2,6-diaminopurine
<220> FEATURE:
<221> NAME/KEY: misc_feature
<222> LOCATION: (29)..(29)
<223> OTHER INFORMATION: n is 2,6-diaminopurine
<220> FEATURE:
```

```
<221> NAME/KEY: misc_feature
<222> LOCATION: (31)..(31)
<223> OTHER INFORMATION: n is 2,6-diaminopurine
<220> FEATURE:
<221> NAME/KEY: misc_feature
<222> LOCATION: (33)..(33)
<223> OTHER INFORMATION: n is 2,6-diaminopurine
<220> FEATURE:
<221> NAME/KEY: misc_feature
<222> LOCATION: (34)..(34)
<223> OTHER INFORMATION: n is 2,6-diaminopurine

<400> SEQUENCE: 192
ngnnungnnu ngnnungnnu ngnnungnnu ngnnu                           35

<210> SEQ ID NO 193
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine

<400> SEQUENCE: 193
naggnaggna gg                                                    12

<210> SEQ ID NO 194
<211> LENGTH: 12
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine

<400> SEQUENCE: 194
cnggcnggcn gg                                                    12

<210> SEQ ID NO 195
<211> LENGTH: 16
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
```

```
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine

<400> SEQUENCE: 195
cnggcnggcn ggcngg                                                     16

<210> SEQ ID NO 196
<211> LENGTH: 16
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine

<400> SEQUENCE: 196
naggnaggna ggnagg                                                     16

<210> SEQ ID NO 197
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 197
naggnaggna ggnaggnagg                                                 20

<210> SEQ ID NO 198
<211> LENGTH: 20
<212> TYPE: RNA
<213> ORGANISM: Artificial
<220> FEATURE:
```

<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine

<400> SEQUENCE: 198
cnggcnggcn ggcnggcngg                                        20

<210> SEQ ID NO 199
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine

<400> SEQUENCE: 199
naggcaggna ggcaggnagg                                        20

<210> SEQ ID NO 200
<211> LENGTH: 20
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine

<400> SEQUENCE: 200
cnggcaggcn ggcaggcngg                                        20

<210> SEQ ID NO 201
<211> LENGTH: 24
<212> TYPE: RNA
<213> ORGANISM: Artificial

```
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine

<400> SEQUENCE: 201
naggnaggna ggnaggnagg nagg                                              24

<210> SEQ ID NO 202
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine

<400> SEQUENCE: 202
cnggcnggcn ggcnggcngg cngg                                              24

<210> SEQ ID NO 203
<211> LENGTH: 28
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
```

<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine

<400> SEQUENCE: 203
naggnaggna ggnaggnagg naggnagg                                    28

<210> SEQ ID NO 204
<211> LENGTH: 28
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine

<400> SEQUENCE: 204
cnggcnggcn ggcnggcngg cnggcngg                                    28

<210> SEQ ID NO 205
<211> LENGTH: 32
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine

```
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine

<400> SEQUENCE: 205
naggnaggna ggnaggnagg naggnaggna gg                                    32

<210> SEQ ID NO 206
<211> LENGTH: 32
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
<222> LOCATION: (26)..(26)
<223> OTHER INFORMATION: n is 2,6-diaminopurine
<220> FEATURE:
<221> NAME/KEY: misc_feature
<222> LOCATION: (30)..(30)
<223> OTHER INFORMATION: n is 2,6-diaminopurine

<400> SEQUENCE: 206
cnggcnggcn ggcnggcngg cnggcnggcn gg                                    32

<210> SEQ ID NO 207
```

```
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (5)..(5)
<223> OTHER INFORMATION: n is 5-methylcytosine
<220> FEATURE:
<221> NAME/KEY: misc_feature
<222> LOCATION: (9)..(9)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (17)..(17)
<223> OTHER INFORMATION: n is 5-methylcytosine
<220> FEATURE:
<221> NAME/KEY: misc_feature
<222> LOCATION: (21)..(21)
<223> OTHER INFORMATION: n is 5-methylcytosine
<220> FEATURE:
<221> NAME/KEY: misc_feature
<222> LOCATION: (25)..(25)
<223> OTHER INFORMATION: n is 5-methylcytosine
<220> FEATURE:
<221> NAME/KEY: misc_feature
<222> LOCATION: (29)..(29)
<223> OTHER INFORMATION: n is 5-methylcytosine
<220> FEATURE:
<221> NAME/KEY: misc_feature
<222> LOCATION: (33)..(33)
<223> OTHER INFORMATION: n is 5-methylcytosine

<400> SEQUENCE: 207
naggnaggna ggnaggnagg naggnaggna ggnagg                                 36

<210> SEQ ID NO 208
<211> LENGTH: 36
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (2)..(2)
<223> OTHER INFORMATION: n is 2,6-diaminopurine
<220> FEATURE:
<221> NAME/KEY: misc_feature
<222> LOCATION: (6)..(6)
<223> OTHER INFORMATION: n is 2,6-diaminopurine
<220> FEATURE:
<221> NAME/KEY: misc_feature
<222> LOCATION: (10)..(10)
<223> OTHER INFORMATION: n is 2,6-diaminopurine
<220> FEATURE:
<221> NAME/KEY: misc_feature
<222> LOCATION: (14)..(14)
<223> OTHER INFORMATION: n is 2,6-diaminopurine
<220> FEATURE:
<221> NAME/KEY: misc_feature
<222> LOCATION: (18)..(18)
<223> OTHER INFORMATION: n is 2,6-diaminopurine
<220> FEATURE:
<221> NAME/KEY: misc_feature
<222> LOCATION: (22)..(22)
<223> OTHER INFORMATION: n is 2,6-diaminopurine
<220> FEATURE:
<221> NAME/KEY: misc_feature
```

```
<222> LOCATION: (26)..(26)
<223> OTHER INFORMATION: n is 2,6-diaminopurine
<220> FEATURE:
<221> NAME/KEY: misc_feature
<222> LOCATION: (30)..(30)
<223> OTHER INFORMATION: n is 2,6-diaminopurine
<220> FEATURE:
<221> NAME/KEY: misc_feature
<222> LOCATION: (34)..(34)
<223> OTHER INFORMATION: n is 2,6-diaminopurine

<400> SEQUENCE: 208
cnggcnggcn ggcnggcngg cnggcnggcn ggcngg                                 36

<210> SEQ ID NO 209
<211> LENGTH: 17
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine

<400> SEQUENCE: 209
ggcucnggcu cnggcuc                                                      17

<210> SEQ ID NO 210
<211> LENGTH: 18
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is an abasic monomer
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (10)..(10)
<223> OTHER INFORMATION: n is an abasic monomer
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (16)..(16)
<223> OTHER INFORMATION: n is an abasic monomer
<220> FEATURE:
<221> NAME/KEY: misc_feature
<222> LOCATION: (18)..(18)
<223> OTHER INFORMATION: n is 5-methylcytosine

<400> SEQUENCE: 210
ggcncnggcn cnggcncn                                                     18

<210> SEQ ID NO 211
<211> LENGTH: 18
<212> TYPE: RNA
<213> ORGANISM: Artificial
<220> FEATURE:
<223> OTHER INFORMATION: Oligonucleotide
<220> FEATURE:
```

```
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine

<400> SEQUENCE: 211
ggcucnggcu cnggcucn                                                    18

<210> SEQ ID NO 212
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 212
ggcucnggcu cnggcucngg cucn                                             24

<210> SEQ ID NO 213
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is an abasic monomer
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (10)..(10)
<223> OTHER INFORMATION: n is an abasic monomer
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (16)..(16)
<223> OTHER INFORMATION: n is an abasic monomer
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (22)..(22)
<223> OTHER INFORMATION: n is an abasic monomer
```

```
<220> FEATURE:
<221> NAME/KEY: misc_feature
<222> LOCATION: (24)..(24)
<223> OTHER INFORMATION: n is 5-methylcytosine

<400> SEQUENCE: 213
ggcncnggcn cnggcncngg cncn                                              24

<210> SEQ ID NO 214
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (16)..(16)
<223> OTHER INFORMATION: n is inosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (24)..(24)
<223> OTHER INFORMATION: n is 5-methylcytosine

<400> SEQUENCE: 214
ggcncnggcn cnggcncngg cncn                                              24

<210> SEQ ID NO 215
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (6)..(6)
<223> OTHER INFORMATION: n is 5-methylcytosine
<220> FEATURE:
<221> NAME/KEY: misc_feature
<222> LOCATION: (12)..(12)
<223> OTHER INFORMATION: n is 5-methylcytosine
<220> FEATURE:
<221> NAME/KEY: misc_feature
<222> LOCATION: (18)..(18)
<223> OTHER INFORMATION: n is 5-methylcytosine
<220> FEATURE:
<221> NAME/KEY: misc_feature
<222> LOCATION: (24)..(24)
<223> OTHER INFORMATION: n is 5-methylcytosine

<400> SEQUENCE: 215
```
ggccunggcc unggccungg ccun                                              24

<210> SEQ ID NO 216
<211> LENGTH: 18
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine

<400> SEQUENCE: 216
ggnunnggnu nnggnunn                                                     18

<210> SEQ ID NO 217
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 217
ggnunnggnu nnggnunngg nunn                                              24

<210> SEQ ID NO 218
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is inosine
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is inosine
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is inosine
<220> FEATURE:

```
<221> NAME/KEY: misc_feature
<222> LOCATION: (17)..(17)
<223> OTHER INFORMATION: n is C or 5-methylcytosine
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is inosine
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 218
ggnnnnggnn nnggnnnngg nnnn                                      24

<210> SEQ ID NO 219
<211> LENGTH: 24
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (3)..(3)
<223> OTHER INFORMATION: n is C or 5-methylcytosine
<220> FEATURE:
<221> NAME/KEY: misc_feature
<222> LOCATION: (4)..(4)
<223> OTHER INFORMATION: n is an abasic monomer
<220> FEATURE:
<221> NAME/KEY: misc_feature
<222> LOCATION: (5)..(5)
<223> OTHER INFORMATION: n is C or 5-methylcytosine
<220> FEATURE:
<221> NAME/KEY: misc_feature
<222> LOCATION: (6)..(6)
<223> OTHER INFORMATION: n is C or 5-methylcytosine
<220> FEATURE:
<221> NAME/KEY: misc_feature
<222> LOCATION: (9)..(9)
<223> OTHER INFORMATION: n is C or 5-methylcytosine
<220> FEATURE:
<221> NAME/KEY: misc_feature
<222> LOCATION: (10)..(10)
<223> OTHER INFORMATION: n is an abasic monomer
<220> FEATURE:
<221> NAME/KEY: misc_feature
<222> LOCATION: (11)..(11)
<223> OTHER INFORMATION: n is C or 5-methylcytosine
<220> FEATURE:
<221> NAME/KEY: misc_feature
<222> LOCATION: (12)..(12)
<223> OTHER INFORMATION: n is C or 5-methylcytosine
<220> FEATURE:
<221> NAME/KEY: misc_feature
<222> LOCATION: (15)..(15)
<223> OTHER INFORMATION: n is C or 5-methylcytosine
<220> FEATURE:
<221> NAME/KEY: misc_feature
<222> LOCATION: (16)..(16)
<223> OTHER INFORMATION: n is an abasic monomer
<220> FEATURE:
<221> NAME/KEY: misc_feature
<222> LOCATION: (17)..(17)
<223> OTHER INFORMATION: n is C or 5-methylcytosine
```

```
<220> FEATURE:
<221> NAME/KEY: misc_feature
<222> LOCATION: (18)..(18)
<223> OTHER INFORMATION: n is C or 5-methylcytosine
<220> FEATURE:
<221> NAME/KEY: misc_feature
<222> LOCATION: (21)..(21)
<223> OTHER INFORMATION: n is C or 5-methylcytosine
<220> FEATURE:
<221> NAME/KEY: misc_feature
<222> LOCATION: (22)..(22)
<223> OTHER INFORMATION: n is an abasic monomer
<220> FEATURE:
<221> NAME/KEY: misc_feature
<222> LOCATION: (23)..(23)
<223> OTHER INFORMATION: n is C or 5-methylcytosine
<220> FEATURE:
<221> NAME/KEY: misc_feature
<222> LOCATION: (24)..(24)
<223> OTHER INFORMATION: n is C or 5-methylcytosine

<400> SEQUENCE: 219
ggnnnnggnn nnggnnnngg nnnn                                          24

<210> SEQ ID NO 220
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (4)..(4)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (10)..(10)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (16)..(16)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is an abasic monomer
<220> FEATURE:
<221> NAME/KEY: misc_feature
<222> LOCATION: (23)..(23)
<223> OTHER INFORMATION: n is an abasic monomer
<220> FEATURE:
<221> NAME/KEY: misc_feature
<222> LOCATION: (24)..(24)
<223> OTHER INFORMATION: n is an abasic monomer
<220> FEATURE:
<221> NAME/KEY: misc_feature
<222> LOCATION: (25)..(25)
<223> OTHER INFORMATION: n is an abasic monomer

<400> SEQUENCE: 220
```
nugnugnugn ugnugnugnu gnnnn 25

```
<210> SEQ ID NO 221
<211> LENGTH: 25
<212> TYPE: RNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(1)
<223> OTHER INFORMATION: n is 5-methylcytosine
<220> FEATURE:
<221> NAME/KEY: misc_feature
<222> LOCATION: (7)..(7)
<223> OTHER INFORMATION: n is 5-methylcytosine
<220> FEATURE:
<221> NAME/KEY: misc_feature
<222> LOCATION: (13)..(13)
<223> OTHER INFORMATION: n is 5-methylcytosine
<220> FEATURE:
<221> NAME/KEY: misc_feature
<222> LOCATION: (19)..(19)
<223> OTHER INFORMATION: n is 5-methylcytosine
<220> FEATURE:
<221> NAME/KEY: misc_feature
<222> LOCATION: (22)..(22)
<223> OTHER INFORMATION: n is an abasic monomer
<220> FEATURE:
<221> NAME/KEY: misc_feature
<222> LOCATION: (23)..(23)
<223> OTHER INFORMATION: n is an abasic monomer
<220> FEATURE:
<221> NAME/KEY: misc_feature
<222> LOCATION: (24)..(24)
<223> OTHER INFORMATION: n is an abasic monomer
<220> FEATURE:
<221> NAME/KEY: misc_feature
<222> LOCATION: (25)..(25)
<223> OTHER INFORMATION: n is an abasic monomer

<400> SEQUENCE: 221
```
nugcugnugc ugnugcugnu gnnnn 25

RNA MODULATING OLIGONUCLEOTIDES WITH IMPROVED CHARACTERISTICS FOR THE TREATMENT OF NEUROMUSCULAR DISORDERS

RELATED APPLICATIONS

This application is a continuation of U.S. patent application Ser. No. 15/676,569, filed Aug. 14, 2017, which is a division of U.S. patent application Ser. No. 14/522,002, filed Oct. 23, 2014, now U.S. Pat. No. 9,745,576, which is a continuation of International Patent Application No. PCT/NL2013/050306, filed Apr. 23, 2013, which claims priority to U.S. Patent Application Ser. No. 61/636,914, filed Apr. 23, 2012, and European Patent Application No. 12165139.2, filed Apr. 23, 2012, the disclosures of which are incorporated herein by reference in their entirety.

Reference to Sequence Listing Submitted Electronically

The content of the electronically submitted sequence listing in ASCII text file (Name: 617845_VCO9-002PCCONDIVCON_Sequence_Listing.txt; Size: 298,997 bytes; Created: Oct. 22, 2019) is incorporated herein by reference in its entirety.

FIELD

The invention relates to the field of human genetics, more specifically neuromuscular disorders. The invention in particular relates to the use of antisense oligonucleotides (AONs) with improved characteristics enhancing clinical applicability as further defined herein.

BACKGROUND OF THE INVENTION

Neuromuscular diseases are characterized by impaired functioning of the muscles due to either muscle or nerve pathology (myopathies and neuropathies). The neuropathies are characterized by neurodegeneration and impaired nerve control leading to problems with movement, spasticity or paralysis. Examples include Huntington's disease (HD), several types of spinocerebellar ataxia (SCA), Friedreich's ataxia (FA), Amyotrophic Lateral Sclerosis (ALS) and Frontotemporal dementia (FTD). A subset of neuropathies is caused by a cis-element repeat instability. For instance, HD is caused by a triplet (CAG)n repeat expansion in exon 1 of the HTT gene. Expansion of these repeats results in expansion of a glutamine stretch at the N-terminal end of the 348 kDa cytoplasmic huntingtin protein. Huntingtin has a characteristic sequence of 6 to 29 glutamine amino acid residues in the normal form; the mutated huntingtin causing the disease has more than 38 residues. The continuous expression of mutant huntingtin molecules in neuronal cells results in the formation of large protein deposits which eventually give rise to cell death, especially in the frontal lobes and the basal ganglia (mainly in the caudate nucleus). The severity of the disease is generally proportional to the number of extra residues. AONs specifically targeting the expanded CAG repeats (such as PS57 (CUG)$_7$ as a 2'-O-methyl phosphorothioate RNA; SEQ ID NO:1 Evers et al.) can be applied to effectively reduce mutant huntingtin transcript and (toxic) protein levels in HD patient-derived cells. For treatment of neuropathies, systemically administered AONs need to pass the blood brain barrier. Thus, there is a need for optimization of oligochemistry allowing and/or exhibiting improved brain delivery.

The myopathies include genetic muscular dystrophies that are characterized by progressive weakness and degeneration of skeletal, heart and/or smooth muscle. Examples of myopathies are Duchenne muscular dystrophy (DMD), myotonic dystrophy type 1 (DM1), and myotonic dystrophy type 2 (DM2). DM1 and DM2 are both also caused by cis-element repeat instability; DM1 by a trinucleotide (CTG)$_n$ repeat expansion in the 3' untranslated region of exon 15 in the DMPK gene, and DM2 by a tetranucleotide (CCTG)$_n$ repeat expansion in the DM2/ZNF9 gene. Also here, AONs specifically targeting the expanded repeats, such as PS58, (CAG)$_7$, a 2'-O-methyl phosphorothioate RNA for DM1 (Mulders et al.), have been shown to efficiently induce the specific degradation of the (toxic) expanded repeat transcripts. In contrast to DMD where the gene defect is associated with increased permeability of the muscle fiber membranes for small compounds as AONs, for most other myopathies an enhanced AON distribution to and uptake by muscle tissue is essential to obtain a therapeutic effect. Thus, also here there is a need for optimization of oligochemistry allowing and/or exhibiting improved muscle delivery.

The particular characteristics of a chosen chemistry at least in part affect the delivery of an AON to the target transcript: administration route, biostability, biodistribution, intra-tissue distribution, and cellular uptake and trafficking. In addition, further optimization of oligonucleotide chemistry is conceived to enhance binding affinity and stability, enhance activity, improve safety, and/or to reduce cost of goods by reducing length or improving synthesis and/or purification procedures. Multiple chemical modifications have become generally and/or commercially available to the research community (such as 2'-O-methyl RNA and 5-substituted pyrimidines and 2,6-diaminopurines), whereas most others still present significant synthetic effort to obtain. Especially preliminary encouraging results have been obtained using 2'-O-methyl phosphorothioate RNA containing modifications on the pyrimidine and purine bases as identified herein.

In conclusion, to enhance the therapeutic applicability of AONs for treating human cis-element repeat instability associated genetic disorders as exemplified herein, there is a need for AONs with further improved characteristics.

DESCRIPTION OF THE INVENTION

Oligonucleotide

In a first aspect, the invention provides an oligonucleotide comprising 2'-O-methyl RNA nucleotide residues, having a backbone wherein at least one phosphate moiety is replaced by a phosphorothioate moiety, and comprising one or more 5-methylpyrimidine and/or one or more 2,6-diaminopurine bases; or an oligonucleotide consisting of 2'-O-methyl RNA nucleotide residues and having a backbone wherein all phosphate moieties are replaced by phosphorothioate moieties, and comprising one or more 5-methylpyrimidine and/or or one or more 2,6-diaminopurine bases, for use as a medicament for treating human cis-element repeat instability associated genetic disorders.

In the context of the invention, "backbone" is used to identify the chain of alternating ribose rings and internucleoside linkages, to which the nucleobases are attached. The term "linkage" is used for the connection between two ribose units (i.e. "internucleoside linkage"), which is generally a phosphate moiety. Thus, an oligonucleotide having 10 nucleotides may contain 9 linkages, linking the 10 ribose units together. Additionally, there may be one or more last linkage(s) present at one or both sides of the oligonucleotide, which is only connected to one nucleotide. The terms "linkage" and "internucleoside linkage" are also meant to indicate such a pendant linkage. At least one of the linkages in the backbone of the oligonucleotide according to the invention consists of a phosphorothioate moiety, linking two ribose units. Thus, at least one of the naturally occurring 3' to 5' phosphodiester moieties present in RNA is replaced by a phosphorothioate moiety.

Within the context of the invention, "a" in each of the following expressions means "at least one": a 2'-O-methyl RNA nucleotide residue, a 2'-O-methyl RNA residue, a phosphorothioate moiety, a 2'-O-methyl phosphorothioate RNA residue, a 5-methylpyrimidine base, a 5-methylcytosine base, a 5-methyluracil base, a thymine base, a 2,6-diaminopurine base.

Preferably, the oligonucleotide according to the invention is an oligonucleotide with less than 37 nucleotides. Said oligonucleotide may have 12, 13, 14, 15, 16, 17, 18, 19, 20, 21, 22, 23, 24, 25, 26, 27, 28, 29, 30, 31, 32, 33, 34, 35, or 36 nucleotides. Such oligonucleotide may also be identified as an oligonucleotide having from 12 to 36 nucleotides.

Accordingly, an oligonucleotide of the invention, comprising a 2'-O-methyl RNA nucleotide residue having a backbone wherein at least one phosphate moiety is replaced by a phosphorothioate moiety, comprises less than 37 nucleotides (i.e. it comprises 12, 13, 14, 15, 16, 17, 18, 19, 20, 21, 22, 23, 24, 25, 26, 27, 28, 29, 30, 31, 32, 33, 34, 35 or 36 nucleotides) and a 5-methylpyrimidine and/or a 2,6-diaminopurine base.

Accordingly, an oligonucleotide of the invention, consisting of 2'-O-methyl RNA nucleotide residues and having a backbone wherein all phosphate moieties are replaced by phosphorothioate, and comprises less than 34 nucleotides (i.e. it comprises 12, 13, 14, 15, 16, 17, 18, 19, 20, 21, 22, 23, 24, 25, 26, 27, 28, 29, 30, 31, 32, 33, 34, 35 or 36 nucleotides) and a 5-methylpyrimidine and/or a 2,6-diaminopurine base.

In a preferred embodiment, the oligonucleotide of the invention comprises a 2'-(O)-methyl phosphorothioate RNA nucleotide residue, or consists of 2'-O-methyl phosphorothioate RNA nucleotide residues. Such oligonucleotide comprises a 2'-(O)-methyl RNA residue, which is connected through a phosphorothioate linkage to the next nucleotide in the sequence. This next nucleotide may be, but not necessarily, another 2'-O-methyl phosphorothioate RNA nucleotide residue. Alternatively, such oligonucleotide consists of 2'-O-methyl phosphorothioate RNA nucleotide residues, wherein all nucleotides comprise a 2'-O-methyl moiety and a phosphorothioate moiety. Preferably, such oligonucleotide consists of 2'-O-methyl phosphorothioate RNA nucleotide residues. Such chemistry is known to the skilled person. Throughout the application, an oligonucleotide comprising a 2'-O-methyl RNA residue and a phosphorothioate linkage may be replaced by an oligonucleotide comprising a 2'-(O)-methyl phosphorothioate RNA nucleotide residue or an oligonucleotide comprising a 2'-O-methyl phosphorothioate RNA residue. Throughout the application, an oligonucleotide consisting of 2'-O-methyl RNA residues linked by or connected through phosphorothioate linkages or an oligonucleotide consisting of 2'-O-methyl phosphorothioate RNA nucleotide residues may be replaced by an oligonucleotide consisting of 2'-O-methyl phosphorothioate RNA.

In addition, an oligonucleotide of the invention comprises at least one base modification that increases binding affinity to target strands, increases melting temperature of the resulting duplex of said oligonucleotide with its target, and/or decreases immunostimulatory effects, and/or increases biostability, and/or improves biodistribution and/or intra-tissue distribution, and/or cellular uptake and trafficking. In an embodiment, an oligonucleotide of the invention comprises a 5-methylpyrimidine and/or a 2,6-diaminopurine base. A 5-methylpyrimidine base is selected from a 5-methylcytosine and/or a 5-methyluracil and/or a thymine, in which thymine is identical to 5-methyluracil. Where an oligonucleotide of the invention has two or more such base modifications, said base modifications may be identical, for example all such modified bases in the oligonucleotide are 5-methylcytosine, or said base modifications may be combinations of different base modifications, for example the oligonucleotide may have one or more 5-methylcytosines and one or more 5-methyluracils.

In a preferred embodiment, an oligonucleotide of the invention (i.e. an oligonucleotide comprising 2'-O-methyl RNA nucleotide residues, having a backbone wherein at least one phosphate moiety is replaced by a phosphorothioate moiety, and comprising one or more 5-methylpyrimidine and/or one or more 2,6-diaminopurine bases; or an oligonucleotide consisting of 2'-O-methyl RNA nucleotide residues and having a backbone wherein all phosphate moieties are replaced by phosphorothioate moieties, and comprising one or more 5-methylpyrimidine and/or one or more 2,6-diaminopurine bases) is such that it does not comprise a 2'-deoxy 2'-fluoro nucleotide (i.e. 2'-deoxy 2'-fluoro-adenosine, -guanosine, -uridine and/or -cytidine). Such oligonucleotide comprising a 2'-fluoro (2'-F) nucleotide has been shown to be able to recruit the interleukin enhancer-binding factor 2 and 3 (ILF2/3) and is thereby able to induce exon skipping in the targeted pre-mRNA (Rigo F, et al, WO2011/097614). In the current invention, the oligonucleotide used preferably does not recruit such factors and/or the oligonucleotide of the invention does not form heteroduplexes with RNA that are specifically recognized by the ILF2/3. The mechanism of action of the oligonucleotide of the current invention is assumed to be distinct from the one of an oligonucleotide with a 2'-F nucleotide: the oligonucleotide of the invention is expected to primarily induce the specific degradation of the (toxic) expanded repeat transcripts.

'Thymine' and '5-methyluracil' may be interchanged throughout the document. In analogy, 2,6-diaminopurine is identical to 2-aminoadenine and these terms may be interchanged throughout the document.

The term "base modification" or "modified base" as identified herein refers to the modification of a naturally occurring base in RNA (i.e. pyrimidine or purine base) or to the de novo synthesis of a base. This de novo synthesized base could be qualified as "modified" by comparison to an existing base.

An oligonucleotide of the invention comprising a 5-methylcytosine and/or a 5-methyluracil and/or a 2,6-diaminopurine base means that at least one of the cytosine nucleobases of said oligonucleotide has been modified by substitution of the proton at the 5-position of the pyrimidine ring with a methyl group (i.e. a 5-methylcytosine), and/or that at least one of the uracil nucleobases of said oligonucleotide has been modified by substitution of the proton at the 5-position of the pyrimidine ring with a methyl group (i.e. a 5-methyluracil), and/or that at least one of the adenine nucleobases of said oligonucleotide has been modified by substitution of the proton at the 2-position with an amino group (i.e. a 2,6-diaminopurine), respectively. Within the context of the invention, the expression "the substitution of a proton with a methyl group in position 5 of the pyrimidine ring" may be replaced by the expression "the substitution of a pyrimidine with a 5-methylpyrimidine," with pyrimidine referring to only uracil, only cytosine or both. Likewise, within the context of the invention, the expression "the substitution of a proton with an amino group in position 2 of adenine" may be replaced by the expression "the substitution of an adenine with a 2,6-diaminopurine." If said oligonucleotide comprises 1, 2, 3, 4, 5, 6, 7, 8, 9 or more cytosines, uracils, and/or adenines, at least 1, 2, 3, 4, 5, 6, 7, 8, 9 or more cytosines, uracils and/or adenines respectively have been modified this way. Preferably all cytosines, uracils and/or adenines have been modified this way or replaced by 5-methylcytosine, 5-methyluracil and/or 2,6-diaminopurine, respectively. No need to say that the invention could only be applied to oligonucleotides comprising at least one cytosine, uracil, or adenine, respectively, in their sequence.

We discovered that the presence of a 5-methylcytosine, 5-methyluracil and/or a 2,6-diaminopurine in an oligonucleotide of the invention has a positive effect on at least one of the parameters or an improvement of at least one parameters of said oligonucleotides. In this context, parameters may include: binding affinity and/or kinetics, silencing activity, biostability, (intra-tissue) distribution, cellular uptake and/or trafficking, and/or immunogenicity of said oligonucleotide, as explained below.

Binding affinity and kinetics depend on the AON's thermodynamic properties. These are at least in part determined by the melting temperature of said oligonucleotide (Tm; calculated with e.g. the oligonucleotide properties calculator (www.unc.edu/∫cail/biotool/oligo/index.html or eu.idtdna.com/analyzer/Applications/OligoAnalyzer/) for single stranded RNA using the basic Tm and the nearest neighbor model), and/or the free energy of the oligonucleotide-target exon complex (using RNA structure version 4.5 or RNA mfold version 3.5). If a Tm is increased, the exon skipping activity typically increases, but when a Tm is too high, the AON is expected to become less sequence-specific. An acceptable Tm and free energy depend on the sequence of the oligonucleotide. Therefore, it is difficult to give preferred ranges for each of these parameters.

An activity of an oligonucleotide of the invention is to inhibit the formation of a mutant protein and/or silence or reduce or decrease the quantity of a disease-associated or disease-causing or mutant transcript containing an extended or unstable number of repeats in a cell of a patient, in a tissue of a patient and/or in a patient as explained later herein. An oligonucleotide of the invention comprising or consisting of a 2'-O-methyl phosphorothioate RNA and a 5-methylcytosine and/or a 5-methyluracil and/or a 2,6-diaminopurine base is expected to be able to silence or reduce or decrease the quantity of said transcript more efficiently than what an oligonucleotide comprising or consisting of a 2'-O-methyl phosphorothioate RNA but without any 5-methylcytosine, without any 5-methyluracil and without any 2,6-diaminopurine base will do. This difference in terms of efficiency may be of at least 1%, 5%, 10%, 15%, 20%, 25%, 30%, 35%, 40%, 45%, 50%, 55%, 60%, 65%, 70%, 75%, 80%, 85%, 90%, 95%, 100%. The reduction or decrease may be assessed by Northern Blotting or (semi-) quantitative RT-PCR for transcript levels (preferably as carried out in the experimental part) or by Western blotting for protein levels. An oligonucleotide of the invention may first be tested in the cellular system like patient-derived fibroblasts as described in Example 1.

Biodistribution and biostability are preferably at least in part determined by a validated hybridization ligation assay adapted from Yu et al., 2002. In an embodiment, plasma or homogenized tissue samples are incubated with a specific capture oligonucleotide probe. After separation, a DIG-labeled oligonucleotide is ligated to the complex and detection followed using an anti-DIG antibody-linked peroxidase. Non-compartmental pharmacokinetic analysis is performed using WINNONLIN software package (model 200, version 5.2, Pharsight, Mountainview, Calif.). Levels of AON (ug) per mL plasma or mg tissue are monitored over time to assess area under the curve (AUC), peak concentration ($C_{max}$), time to peak concentration ($T_{max}$), terminal half life and absorption lag time ($t_{lag}$). Such a preferred assay has been disclosed in the experimental part.

AONs may stimulate an innate immune response by activating the Toll-like receptors (TLR), including TLR9 and TLR7 (Krieg et al., 1995). The activation of TLR9 typically occurs due to the presence of non-methylated CG sequences present in oligodeoxynucleotides (ODNs), by mimicking bacterial DNA which activates the innate immune system through TLR9-mediated cytokine release. The 2'-O-methyl modification is however suggested to markedly reduce such possible effect. TLR7 has been described to recognize uracil repeats in RNA (Diebold et al., 2006).

Activation of TLR9 and TLR7 result in a set of coordinated immune responses that include innate immunity (macrophages, dendritic cells (DC), and NK cells)(Krieg et al., 1995; Krieg, 2000). Several chemo- and cytokines, such as IP-10, TNFα, IL-6, MCP-1 and IFNα (Wagner, 1999; Popovic et al., 2006) have been implicated in this process. The inflammatory cytokines attract additional defensive cells from the blood, such as T and B cells. The levels of these cytokines can be investigated by in vitro testing. In short, human whole blood is incubated with increasing concentrations of AONs after which the levels of the cytokines are determined by standard commercially available ELISA kits. A decrease in immunogenicity preferably corresponds to a detectable decrease of concentration of at least one of the cytokines mentioned above by comparison to the concentration of corresponding cytokine in an assay in a cell treated with an oligonucleotide comprising at least one 5-methylcytosine and/or 5-methyluracil, and/or 2,6-diaminopurine compared to a cell treated with a corresponding oligonucleotide having no 5-methylcytosines, 5-methyluracils, or 2,6-diaminopurines.

Accordingly, a preferred oligonucleotide of the invention has an improved parameter, such as an acceptable or a decreased immunogenicity and/or a better biodistribution and/or acceptable or improved RNA binding kinetics and/or thermodynamic properties by comparison to a corresponding oligonucleotide consisting of a 2'-O-methyl phosphorothioate RNA without a 5-methylcytosine, without a 5-methyluracil and without a 2,6-diaminopurine. Each of these parameters could be assessed using assays known to the skilled person or preferably as disclosed herein.

Below other chemistries and modifications of the oligonucleotide of the invention are defined. These additional chemistries and modifications may be present in combination with the chemistry already defined for said oligonucleotide, i.e. the presence of a 5-methylcytosine, a 5-methyluracil and/or a 2,6-diaminopurine, and the oligonucleotide comprising or consisting of 2'-O-methyl phosphorothioate RNA.

A preferred oligonucleotide of the invention comprises or consists of an RNA molecule or a modified RNA molecule.

In a preferred embodiment, an oligonucleotide is single stranded. The skilled person will understand that it is however possible that a single stranded oligonucleotide may form an internal double stranded structure. However, this oligonucleotide is still named a single stranded oligonucleotide in the context of this invention. A single stranded oligonucleotide has several advantages compared to a double stranded siRNA oligonucleotide: (i) its synthesis is expected to be easier than two complementary siRNA strands; (ii) there is a wider range of chemical modifications possible to enhance uptake in cells, a better (physiological) stability and to decrease potential generic adverse effects; (iii) siRNAs have a higher potential for non-specific effects (including off-target genes) and exaggerated pharmacology (e.g. less control possible of effectiveness and selectivity by treatment schedule or dose) and (iv) siRNAs are less likely to act in the nucleus and cannot be directed against introns.

In addition to the modifications described above, the oligonucleotide of the invention may comprise further modifications such as different types of nucleic acid nucleotide residues or nucleotides as described below. Different types of nucleic acid nucleotide residues may be used to generate an oligonucleotide of the invention. Said oligonucleotide may have at least one backbone modification (internucleoside linkage and/or sugar modification) and/or at least one base modification compared to an RNA-based oligonucleotide.

A base modification includes a modified version of the natural purine and pyrimidine bases (e.g. adenine, uracil, guanine, cytosine, and thymine), such as hypoxanthine (e.g. inosine), orotic acid, agmatidine, lysidine, pseudouracil, 2-thiopyrimidine (e.g. 2-thiouracil, 2-thiothymine), G-clamp and its derivatives, 5-substituted pyrimidine (e.g. 5-halouracil, 5-propynyluracil, 5-propynylcytosine, 5-aminomethyluracil, 5-hydroxymethyluracil, 5-aminomethylcytosine, 5-hydroxymethylcytosine, Super T), 7-deazaguanine, 7-deazaadenine, 7-aza-2,6-diaminopurine, 8-aza-7-deazaguanine, 8-aza-7-deazaadenine, 8-aza-7-deaza-2,6-diaminopurine, Super G, Super A, and N4-ethylcytosine, or derivatives thereof; $N^2$-cyclopentylguanine (cPent-G), $N^2$-cyclopentyl-2-aminopurine (cPent-AP), and $N^2$-propyl-2-aminopurine (Pr-AP), or derivatives thereof; and degenerate or universal bases, like 2,6-difluorotoluene or absent bases like abasic sites (e.g. 1-deoxyribose, 1,2-dideoxyribose, 1-deoxy-2-O-methylribose; or pyrrolidine derivatives in which the ring oxygen has been replaced with nitrogen (azaribose)). Examples of derivatives of Super A, Super G and Super T can be found in U.S. Pat. No. 6,683,173 (Epoch Biosciences), which is incorporated here entirely by reference. cPent-G, cPent-AP and Pr-AP were shown to reduce immunostimulatory effects when incorporated in siRNA (Peacock H. et al.).

In an embodiment, an oligonucleotide of the invention comprises an abasic site or an abasic monomer. Within the context of the invention, such monomer may be called an abasic site or an abasic monomer. An abasic monomer or abasic site is a nucleotide residue or building block that lacks a nucleobase by comparison to a corresponding nucleotide residue comprising a nucleobase. Within the invention, an abasic monomer is thus a building block part of an oligonucleotide but lacking a nucleobase. Such abasic monomer may be present or linked or attached or conjugated to a free terminus of an oligonucleotide.

In a more preferred embodiment, an oligonucleotide of the invention comprises 1-10 or more abasic monomers.

Therefore, 1, 2, 3, 4, 5, 6, 7, 8, 9, 10 or more abasic monomers may be present in an oligonucleotide of the invention.

An abasic monomer may be of any type known and conceivable by the skilled person, non-limiting examples of which are depicted below:

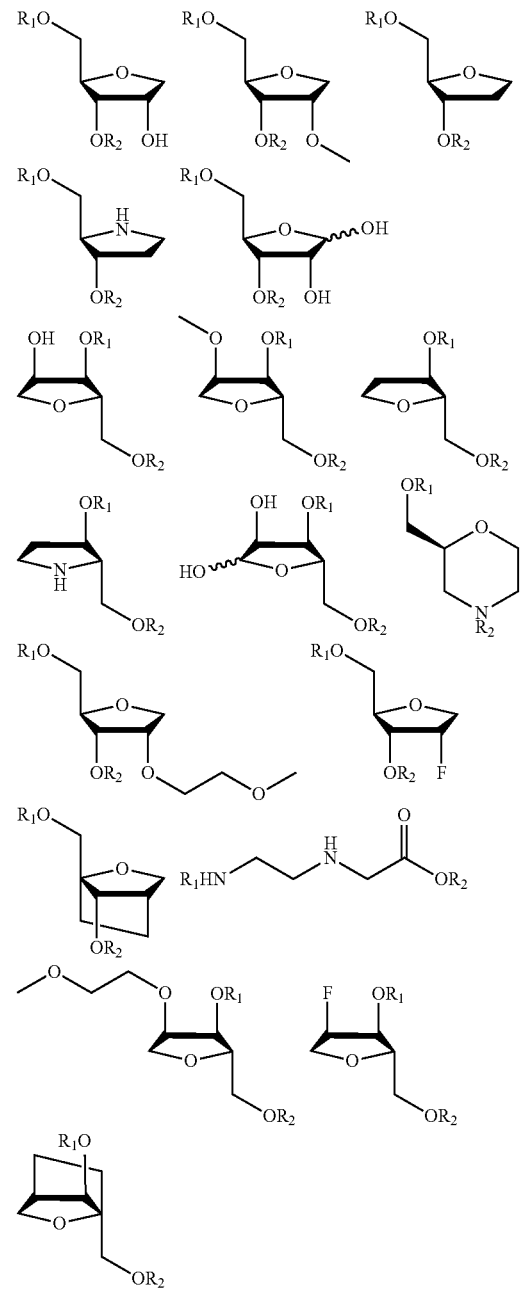

Herein, $R_1$ and $R_2$ are independently H, an oligonucleotide or other abasic site(s), provided that not both $R_1$ and $R_2$ are H and $R_1$ and $R_2$ are not both an oligonucleotide. An abasic monomer(s) can be attached to either or both termini of the oligonucleotide as specified before. It should be noted that an oligonucleotide attached to one or two an abasic site(s) or abasic monomer(s) may comprise less than 12 nucleotides. In this respect, the oligonucleotide according to the invention may comprise at least 12 nucleotides, optionally including one or more abasic sites or abasic monomers at one or both termini.

In the sequence listing, an oligonucleotide of the invention comprising an abasic monomer may be represented by its nucleotide or base sequence; the abasic monomer not being represented since it may be considered as linked or attached or conjugated to a free terminus of an oligonucleotide. This is the case for base sequences SEQ ID NO: 107 and 108. In table 2, the full sequence of preferred oligonucleotides comprising SEQ ID NO:107 or 108 is provided: such oligonucleotide comprises SEQ ID NO: 107 or 108 and 4 abasic monomers at the 3' terminus of the corresponding SEQ ID NO: 107 or 108. SEQ ID NO: 220 and 221 correspond to SEQ ID NO: 107 and 108 further comprising 4 additional abasic monomers at the 3' terminus of the oligonucleotide.

When an abasic monomer is present within a base sequence of an oligonucleotide, said abasic monomer is identified in the sequence listing as part of the sequence of said oligonucleotide as in SEQ ID NO:210 and 213.

In tables 1 and 2, an abasic monomer is identified using the letter Q.

Depending on its length an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 base modifications. It is also encompassed by the invention to introduce more than one distinct base modification in said oligonucleotide.

A "sugar modification" indicates the presence of a modified version of the ribosyl moiety as naturally occurring in RNA (i.e. the furanosyl moiety), such as bicyclic sugars, tetrahydropyrans, morpholinos, 2'-modified sugars, 4'-modified sugars, 5'-modified sugars, and 4'-substituted sugars. Examples of suitable sugar modifications include, but are not limited to, 2'-O-modified RNA nucleotide residues, such as 2'-O-alkyl or 2'-O-(substituted)alkyl e.g. 2'-O-methyl, 2'-O-(2-cyanoethyl), 2'-O-(2-methoxy)ethyl (2'-MOE), 2'-O-(2-thiomethyl)ethyl, 2'-O-butyryl, 2'-O-propargyl, 2'-O-allyl, 2'-O-(2-amino)propyl, 2'-O-(2-(dimethylamino) propyl), 2'-O-(2-amino)ethyl, 2'-O-(2-(dimethylamino) ethyl); 2'-deoxy (DNA); 2'-O-(haloalkoxy)methyl (Arai K. et al.) e.g. 2'-O-(2-chloroethoxy)methyl (MCEM), 2'-O-(2, 2-dichloroethoxy)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl](DCME); 2'-halo e.g. 2'-F, FANA (2'-F arabinosyl nucleic acid); carbasugar and azasugar modifications; 3'-O-alkyl e.g. 3'-O-methyl, 3'-O-butyryl, 3'-O-propargyl, 5'-alkyl e.g. 5'-methyl; and their derivatives.

Another sugar modification includes "bridged" or "bicylic" nucleic acid (BNA), e.g. locked nucleic acid (LNA), xylo-LNA, α-L-LNA, β-D-LNA, cEt (2'-0,4'-C constrained ethyl) LNA, cMOEt (2'-0,4'-C constrained methoxyethyl) LNA, ethylene-bridged nucleic acid (ENA), BNA$^{NC}$[N-Me] (as described in Chem. Commun. 2007, 3765, which is incorporated in its entirety by reference); tricyclo DNA (tcDNA); unlocked nucleic acid (UNA); 5'-methyl substituted BNAs (as described in U.S. patent application Ser. No. 13/530,218, which is incorporated in its entirety by reference); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (as e.g. in PMO, PMOPlus, PMO-X) and their derivatives, preferably locked nucleic acid (LNA), xylo-LNA, α-L-LNA, β-D-LNA, cEt (2'-0,4'-C constrained ethyl) LNA, cMOEt (2'-0,4'-C constrained methoxyethyl) LNA, ethylene-bridged nucleic acid (ENA), tricyclo DNA (tcDNA); cyclohexenyl nucleic acid (CeNA), altriol nucleic acid (ANA), hexitol nucleic acid (HNA), fluorinated HNA (F-HNA), pyranosyl-RNA (p-RNA), 3'-deoxypyranosyl-DNA (p-DNA); morpholino (as e.g. in PMO, PMOPlus, PMO-X) and their derivatives. A preferred tcDNA is tc-PS-DNA (tricyclo DNA comprising phosphorothioate internucleoside linkage). Depending on its length, an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or 36 sugar modifications. It is also encompassed by the invention to introduce more than one distinct sugar modification in said oligonucleotide. In an embodiment, an oligonucleotide as defined herein comprises or consists of an LNA or a derivative thereof. BNA derivatives are for example described in WO 2011/097641, which is incorporated in its entirety by reference. In a more preferred embodiment, an oligonucleotide of the invention is fully 2'-O-methyl modified. Examples of PMO-X are described in WO2011150408, which is incorporated here in its entirety by reference.

In a preferred embodiment, the oligonucleotide according to the invention comprises, apart from the mandatory 2'-O-methyl sugar modification, at least one other sugar modification selected from 2'-O-methyl, 2'-O-(2-methoxy)ethyl, morpholino, a bridged nucleotide or BNA, or the oligonucleotide comprises both bridged nucleotides and 2'-deoxy modified nucleotides (BNA/DNA mixmers). More preferably, the oligonucleotide according to the invention is modified over its full length with a sugar modification selected from 2'-O-methyl, 2'-O-(2-methoxy)ethyl, morpholino, bridged nucleic acid (BNA) or BNA/DNA mixmer.

In a more preferred embodiment, the oligonucleotide according to the invention comprises is fully 2'-O-methyl modified, preferably fully 2'-O-methyl phosphorothioate modified.

A "backbone modification" indicates the presence of a modified version of the ribosyl moiety ("sugar modification"), as indicated above, and/or the presence of a modified version of the phosphodiester as naturally occurring in RNA ("internucleoside linkage modification"). Examples of internucleoside linkage modifications, which are compatible with the present invention, are phosphorothioate (PS), chirally pure phosphorothioate, phosphorodithioate (PS2), phosphonoacetate (PACE), phosphonoacetamide (PACA), thiophosphonoacetate, thiophosphonoacetamide, phosphorothioate prodrug, H-phosphonate, methyl phosphonate, methyl phosphonothioate, methyl phosphate, methyl phosphorothioate, ethyl phosphate, ethyl phosphorothioate, boranophosphate, boranophosphorothioate, methyl boranophosphate, methyl boranophosphorothioate, methyl boranophosphonate, methyl boranophosphonothioate, and their derivatives. Another modification includes phosphoramidite, phosphoramidate, N3'→P5' phosphoramidate, phosphordiamidate, phosphorothiodiamidate, sulfamate, dimethylenesulfoxide, sulfonate, triazole, oxalyl, carbamate, methyleneimino (MMI), and thioacetamido nucleic acid (TANA); and their derivatives. Depending on its length, an oligonucleotide of the invention may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 backbone modifications. It is also encompassed by the invention to introduce more than one distinct backbone modification in said oligonucleotide.

An oligonucleotide of the invention comprises at least one phosphorothioate modification. In a more preferred embodiment, an oligonucleotide of the invention is fully phosphorothioate modified.

Other chemical modifications of an oligonucleotide of the invention include peptide-base nucleic acid (PNA), boron-cluster modified PNA, pyrrolidine-based oxy-peptide nucleic acid (POPNA), glycol- or glycerol-based nucleic acid (GNA), threose-based nucleic acid (TNA), acyclic threoninol-based nucleic acid (aTNA), morpholino-based oligonucleotide (PMO, PPMO, PMO-X), cationic morpholino-based oligomers (PMOPlus), oligonucleotides with integrated bases and backbones (ONIBs), pyrrolidine-amide oligonucleotides (POMs); and their derivatives.

In another embodiment, an oligonucleotide comprises a peptide nucleic acid and/or a morpholino phosphorodiamidate or a derivative thereof.

Thus, the preferred oligonucleotide according to one aspect of the invention comprises:
(a) at least one base modification selected from 5-methylpyrimidine and 2,6-diaminopurine; and/or
(b) at least one sugar modification, which is 2'-O-methyl, and/or
(c) at least one backbone modification, which is phosphorothioate.

Thus, a preferred oligonucleotide according to this aspect of the invention comprises a base modification (a) and no sugar modification (b) and no backbone modification (c). Another preferred oligonucleotide according to this aspect of the invention comprises a sugar modification (b) and no base modification (a) and no backbone modification (c). Another preferred oligonucleotide according to this aspect of the invention comprises a backbone modification (c) and no base modification (a) and no sugar modification (b). Also oligonucleotides having none of the above-mentioned modifications are understood to be covered by the present invention, as well as oligonucleotides comprising two, i.e. (a) and (b), (a) and (c) and/or (b) and (c), or all three of the modifications (a), (b) and (c), as defined above. In another preferred embodiment, any of the oligonucleotides as described in the previous paragraph may comprise:
(a) at least one (additional) base modification selected from 2-thiouracil, 2-thiothymine, 5-methylcytosine, 5-methyluracil, thymine, 2,6-diaminopurine; and/or
(b) at least one (additional) sugar modification selected from 2'-O-methyl, 2'-O-(2-methoxy)ethyl, 2'-deoxy (DNA), morpholino, a bridged nucleotide or BNA, or the oligonucleotide comprises both bridged nucleotides and 2'-deoxy modified nucleotides (BNA/DNA mixmers); and/or
(c) at least one (additional) backbone modification selected from (another) phosphorothioate or phosphordiamidate.

In another preferred embodiment, the oligonucleotide according to the invention is modified over its entire length with one or more of the same modification, selected from (a) one of the base modifications; and/or (b) one of the sugar modifications; and/or (c) one of the backbone modifications.

With the advent of nucleic acid mimicking technology, it has become possible to generate molecules that have a similar, preferably the same hybridization characteristics in kind not necessarily in amount as nucleic acid itself. Such functional equivalents are of course also suitable for use in the invention.

The skilled person will understand that not each sugar, base, and/or backbone may be modified the same way. Several distinct modified sugars, bases and/or backbones may be combined into one single oligonucleotide of the invention.

A person skilled in the art will also recognize that there are many synthetic derivatives of oligonucleotides.

Preferably, said oligonucleotide comprises RNA, as RNA/RNA duplexes are very stable. It is preferred that an RNA oligonucleotide comprises a modification providing the RNA with an additional property, for instance resistance to endonucleases, exonucleases, and RNaseH, additional hybridisation strength, increased stability (for instance in a bodily fluid), increased or decreased flexibility, increased activity, reduced toxicity, increased intracellular transport, tissue-specificity, etc. In addition, the mRNA complexed with the oligonucleotide of the invention is preferably not susceptible to RNaseH cleavage. Preferred modifications have been identified above.

Oligonucleotides containing at least in part naturally occurring DNA nucleotides are useful for inducing degradation of DNA-RNA hybrid molecules in the cell by RNase H activity (EC.3.1.26.4).

Naturally occurring RNA ribonucleotides or RNA-like synthetic ribonucleotides comprising oligonucleotides are encompassed herein to form double stranded RNA-RNA hybrids that act as enzyme-dependent antisense through the RNA interference or silencing (RNAi/siRNA) pathways, involving target RNA recognition through sense-antisense strand pairing followed by target RNA degradation by the RNA-induced silencing complex (RISC).

Alternatively or in addition, an oligonucleotide can interfere with the processing or expression of precursor RNA or messenger RNA (steric blocking, RNaseH independent processes) in particular but not limited to RNA splicing and exon skipping, by binding to a target sequence of RNA transcript and getting in the way of processes such as translation or blocking of splice donor or splice acceptor sites. Moreover, the oligonucleotide may inhibit the binding of proteins, nuclear factors and others by steric hindrance and/or interfere with the authentic spatial folding of the target RNA and/or bind itself to proteins that originally bind to the target RNA and/or have other effects on the target RNA, thereby contributing to the destabilization of the target RNA, preferably pre-mRNA, and/or to the decrease in amount of diseased or toxic transcript and/or protein in diseases like HD as identified later herein.

As herein defined, an oligonucleotide may comprise nucleotides with (RNaseH resistant) chemical substitutions at least one of its 5' or 3' ends, to provide intracellular stability, and comprises less than 9, more preferably less than 6 consecutive (RNaseH-sensitive) deoxyribose nucleotides in the rest of its sequence. The rest of the sequence is preferably the center of the sequence. Such oligonucleotide is called a gapmer.

Gapmers have been extensively described in WO 2007/089611. Gapmers are designed to enable the recruitment and/or activation of RNaseH. Without wishing to be bound by theory, it is believed that RNaseH is recruited and/or activated via binding to the central region of the gapmer made of deoxyriboses. An oligonucleotide of the invention which is preferably substantially independent of or independent of RNaseH is designed in order to have a central region which is substantially not able or is not able to recruit and/or activate RNaseH. In a preferred embodiment, the rest of the sequence of said oligonucleotide, more preferably its central part comprises less than 9, 8, 7, 6, 5, 4, 3, 2, 1, or no deoxyribose. Accordingly, this oligonucleotide of the invention is preferably partly to fully replaced as earlier defined herein. "Partly replaced" means that the oligonucleotide comprises at least some of nucleotides that have been replaced, preferably at least 50% of its nucleotides have been replaced, or at least 55%, 60%, 65%, 70%, 75%, 80%, 85%, 90% or 95% have been replaced. 100% replacement of nucleotides corresponds to "fully replaced".

Accordingly, the invention provides an oligonucleotide comprising a 2'-O-methyl phosphorothioate RNA residue or consisting of 2'-O-methyl phosphorothioate RNA and comprising a 5-methylpyrimidine and/or a 2,6-diaminopurine base. Most preferably, this oligonucleotide consists of 2'-O-methyl RNA residues connected through a phosphorothioate backbone and all of its cytosines and/or all of its uracils and/or all of its adenines, independently, have been replaced by 5-methylcytosine, 5-methyluracil and/or 2,6-diaminopurine, respectively. Thus, an oligonucleotide of the invention may have:

At least one and preferably all cytosines replaced with 5-methylcytosines,

At least one and preferably all cytosines replaced with 5-methylcytosines and at least one and preferably all uracils replaced with 5-methyluracils, At least one and preferably all cytosines replaced with 5-methylcytosines and at least one and preferably all adenines replaced with 2,6-diaminopurines, At least one and preferably all cytosines replaced with 5-methylcytosines and at least one and preferably all uracils replaced with 5-methyluracils and at least one and preferably all adenines replaced with 2,6-diaminopurines, At least one and preferably all uracils replaced with 5-methyluracils, At least one and preferably all uracils replaced with 5-methyluracils and at least one and preferably all adenines replaced with 2,6-diaminopurines, or At least one and preferably all adenines replaced with 2,6-diaminopurines.

An oligonucleotide of the invention is for use as a medicament for preventing delaying and/or treating a human cis-element repeat instability associated genetic disorders preferably as exemplified herein. A human cis-element repeat instability associated genetic disorders as identified herein is preferably a neuromuscular disorder. Preferably said oligonucleotide is for use in therapeutic RNA modulation. Therefore, the oligonucleotide according to the invention may be described as an antisense oligonucleotide (AON). An antisense oligonucleotide is an oligonucleotide which binds (or is able to bind), targets, hybridizes to (or is able to hybridize to) and/or is reverse complementary to a specific sequence of a transcript of a gene which is known to be associated with or involved in a human cis-element repeat instability associated genetic neuromuscular disorder.

According to the invention, an antisense oligonucleotide comprising or consisting of 2'-O-methyl RNA nucleotide residues, having a backbone wherein at least one phosphate moiety is replaced by a phosphorothioate moiety, and further comprising at least one of a 5-methylcytosine and/or a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a repetitive element in a RNA transcript having as repetitive nucleotide unit a repetitive nucleotide unit, which is selected from the $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$. Said oligonucleotide is preferably a single stranded oligonucleotide.

Although it is to be understood that an oligonucleotide of the invention binds (or is able to bind), hybridizes (or is able to hybridize), targets and/or is reverse complementary to a repetitive element present in a RNA transcript as identified above, it can not be ruled out that such oligonucleotide may also interfere with or bind (or is able to bind) or hybridize to (or is able to hybridize) a corresponding DNA, this RNA transcript is derived from.

A repeat or repetitive element or repetitive sequence or repetitive stretch is herein defined as a repetition of at least 3, 4, 5, 10, 100, 1000 or more, of a repetitive unit or repetitive nucleotide unit or repeat nucleotide unit (as $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$), comprising a tri-nucleotide repetitive unit, or alternatively a 4, 5 or 6 nucleotide repetitive unit, in a transcribed gene sequence in the genome of a subject, including a human subject. Accordingly, n is an integer and may be at least 3, 4, 5, 10, 100, 1000 or more. The invention is not limited to exemplified repetitive nucleotide units. Other repetitive nucleotide unit could be found on the following site neuromuscular.wustl.edu/mother/dnarep.htm. In the majority of patients, a 30 "pure" repeat or repetitive element or repetitive sequence or repetitive stretch as identified above (as $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$) is present in a transcribed gene sequence in the genome of said patient. However, it is also encompassed by the invention, that in some patients, said repeat or repetitive element or repetitive sequence or repetitive stretch as identified above is not qualified as "pure" or is qualified as a "variant" when for example said repeat or repetitive element or repetitive sequence or repetitive stretch as identified above is interspersed with at least 1, 2, or 3 nucleotide(s) that do not fit the nucleotide(s) of said repeat or repetitive element or repetitive sequence or repetitive stretch (Braida C., et al,).

An oligonucleotide according to the invention therefore may not need to be 100% reverse complementary to a targeted repeat. Usually an oligonucleotide of the invention may be at least 90%, 95%, 97%, 99% or 100% reverse complementary to a targeted repeat.

In an embodiment, an antisense oligonucleotide comprises or consists of 2'-O-methyl phosphorothioate RNA, comprises a 5-methylcytosine and/or a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a $(CAG)_n$ tract in a transcript and is particularly useful for the treatment, delay, amelioration and/or prevention of the human genetic diseases Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropallidoluysian atrophy (DRPLA) caused by CAG repeat expansions in the transcripts of the HTT (SEQ ID NO: 80), ATXN1 (SEQ ID NO:81), ATXN2 (SEQ ID NO: 82) ATXN3 (SEQ ID NO: 83), CACNA1A (SEQ ID NO:84), ATXN7 (SEQ ID NO: 85), PPP2R2B (SEQ ID NO: 86), TBP (SEQ ID NO: 87), AR (SEQ ID NO: 88) or ATN1 (SEQ ID NO: 89) genes.

Preferably, these genes are from human origin. In this embodiment, an oligonucleotide comprises or consists of 2'-O-methyl phosphorothioate RNA, comprises a 5-methylcytosine and/or a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a $(CAG)_n$ repeat as identified above and has as repetitive nucleotide unit $(CUG)_m$. The m in $(CUG)_m$ is preferably an integer which is 4, 5, 6, 7, 8, 9, 10, 11, 12. In a preferred embodiment, m is 5 or 6 or 7 or 8 or 9 or 10 or 11 or 12.

It is to be noted that for ALS and FTD, it is known that at least two distinct repeats in at least two distinct transcripts may be involved or may be responsible or linked with the disease. One has been identified in the previous paragraph (i.e. $(CAG)_n$ in a ATXN2 transcript). Another one is being identified later as a $(GGGGCC)_n$ repeat or tract in a C9ORF72 transcript. It means that for each of these two diseases, one may envisage to use either one of these two distinct oligonucleotides of the invention to specifically induce the specific degradation of the corresponding (toxic) expanded repeat transcripts.

Throughout the application, an oligonucleotide defined as being reverse complementary to, binding (being able to bind), hybridizing (being able to hybridize) or targeting a repeat as identified above and has or comprises a repetitive nucleotide unit may have any length comprised from 12 to 36 nucleotides. If we take the example of CUG as repetitive nucleotide unit comprised within said oligonucleotide, any oligonucleotide comprising UGC or GCU as repetitive nucleotide unit is also encompassed by the present invention. Depending on the length of said oligonucleotide (for example from 12 to 36 nucleotides), the given repetitive nucleotide unit may not be complete at the 5' and/or at the 3' side of said oligonucleotide. Each of said oligonucleotide is encompassed within the scope of said invention.

Alternatively, if we still take as an example the oligonucleotide having CUG as repetitive nucleotide unit, it may be represented by $H-(P)_p-(CUG)_m-(Q)_q-H$, wherein m is an integer as defined above. Each occurrence of P and Q is, individually, an abasic monomer as defined above or a nucleotide, such as A, C, G, U or an analogue or equivalent thereof and p and q are each individually an integer, preferably 0, 1, 2, 3, 4, 5, 6, 7, 8, 9, 10, 11, 12, 13, 14, 15, 16, 17, 18, 19, 20 or higher up to 100. Thus, p and q are each individually an integer from 0 to 100, preferably an integer from 0 to 20, more preferably an integer from 0 to 10, more preferably from 0 to 6, even more preferably from 0 to 3. Thus, when p is 0, P is absent and when q is 0, Q is absent. The skilled person will appreciate that an oligonucleotide will always start with and end with a hydrogen atom (H), regardless of the amount and nature of the nucleotides present in the oligonucleotide.

It will be appreciated that herein $(CUG)_m$ may be replaced by any repeating nucleotide unit within the context of the invention. Thus, a preferred oligonucleotide according to the invention may be represented by $H-(P)_p-(R)_r-(Q)_q-H$, wherein $(R)_r$ is a repeating nucleotide unit within the context of the invention and P, Q, p and q are as defined above.

In the context of the present invention, an "analogue" or an "equivalent" of a nucleotide is to be understood as a nucleotide which comprises at least one modification with respect to the nucleotides naturally occurring in RNA, such as A, C, G and U. Such a modification may be a internucleoside linkage modification and/or a sugar modification and/or a base modification, as explained and exemplified above.

Again taking the oligonucleotide having CUG as repetitive nucleotide unit, it is to be understood that the repeating sequence may start with either a C, a U or a G. Thus, in a preferred embodiment, p is not 0, and $(P)_p$ is represented by $(P')_p\text{UG}$ or $(P')_{p''}\text{G}$, wherein each occurrence of P' is, individually, an abasic site or a nucleotide, such as A, C, G, U or an analogue or equivalent thereof, and p' is p–2 and p" is p–1. Such oligonucleotides may be represented as:

$H-(P')_{p'}\text{UG-}(CUG)_m-(Q)_q-H$ or $H-(P')_{p''}\text{G-}(CUG)_m-(Q)_q-H$.

In an equally preferred embodiment, q is not 0, and $(Q)_q$ is represented by $CU(Q')_{q'}$ or $C(Q')_{q''}$, and each occurrence of Q' is, individually, an abasic site or a nucleotide, such as A, C, G, U or an analogue or equivalent thereof, and q' is q–2 and q" is q–1. Such oligonucleotides may be represented as:

$H-(P)_p-(CUG)_m-CU(Q')_{q'}-H$ or $H-(P)_p-(CUG)_m-C(Q')_{q''}-H$.

In another preferred embodiment, both p and q are not 0, and both $(P)_p$ and $(Q)_q$ are represented by $(P')_p\text{UG}$ or $(P')_{p''}\text{G}$ and $CU(Q')_{q'}$ or $C(Q')_{q''}$ respectively, wherein P', Q', p', p", q' and q" are as defined above. Such oligonucleotides may be represented as:

$H-(P')_{p'}\text{UG-}(CUG)_m-CU(Q')_{q'}-H$, $H-(P')_{p''}\text{G-}(CUG)_m-CU(Q')_{q'}-H$, $H-(P')_{p'}\text{UG-}(CUG)_m-C(Q')_{q''}-H$, or $H-(P')_{p''}\text{G-}(CUG)_m-C(Q')_{q''}-H$.

It is to be understood that p', p", q' and q" may not be negative integers. Thus, when $(P)_p$ is represented by $(P')_{p'}\text{UG}$ or $(P')_{p''}\text{G}$, p is at least 1 or at least 2 respectively, and when $(Q)_q$ is represented by $CU(Q')_{q'}$ or $C(Q')_{q''}$, q is at least 1 or at least 2 respectively. It is to be understood that all said here regarding the CUG repeat unit can be extended to any repeat unit within the context of the invention.

In a preferred embodiment, an oligonucleotide defined as being reverse complementary to, binding (or being able to bind), hybridizing (or being able to hybridize) or targeting a $(CAG)_n$ repeat comprises or consists of a repetitive nucleotide unit $(XYG)_m$ and has a length comprised from 12 to 36 nucleotides and wherein each X is C or 5-methylcytosine, and each Y is U or 5-methyluracil such that at least one X is 5-methylcytosine and/or at least one Y is 5-methyluracil. m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit $(XYG)_m$, wherein each X is C or 5-methylcytosine, and each Y is U or 5-methyluracil such that at least one X is 5-methylcytosine and/or at least one Y is 5-methyluracil, and m is an integer from 4 to 12 (SEQ ID NO:2 to 12).

An even more preferred oligonucleotide comprises or consists of a repetitive nucleotide unit $(XYG)_m$, wherein each X is 5-methylcytosine, and/or each Y is 5-methyluracil, and m is an integer from 4 to 12 (SEQ ID NO:2 to 12).

An even more preferred oligonucleotide therefore comprises or consists of a repetitive nucleotide unit $(XYG)_5$, $(XYG)_6$ or $(XYG)_7$, $(XYG)_8$, or $(XYG)_9$ wherein each X is C or 5-methylcytosine, and each Y is U or 5-methyluracil such that at least one X is 5-methylcytosine and/or at least one Y is 5-methyluracil. More preferred is an oligonucleotide comprising or consisting of $(XYG)_7$, wherein each X is C or 5-methylcytosine, and each Y is U or 5-methyluracil such that at least one X is 5-methylcytosine and/or at least one Y is 5-methyluracil (SEQ ID NO:7).

An even more preferred oligonucleotide comprises or consists of a repetitive nucleotide unit $(XYG)_7$, wherein each X is 5-methylcytosine and each Y is a uracil (SEQ ID NO: 2), or each X is a cytosine and each Y is 5-methyluracil (SEQ ID NO:3). An even more preferred oligonucleotide comprises SEQ ID NO:2 or 3 and has a length of 21, 22, 23, 24, 25, 26, 27, 28, 29, 30 nucleotides.

Most preferred oligonucleotides sequences comprising or consisting of a repetitive nucleotide unit $(XYG)_m$ have been identified in table 2 as SEQ ID NO:90-118.

A preferred oligonucleotide comprising or consisting of 2'-O-methyl phosphorothioate RNA comprises one of base sequences SEQ ID NO: 90-106 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 90-106 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 90-106 and has a length of 21 nucleotides.

A preferred oligonucleotide comprising or consisting of 2'-O-methyl phosphorothioate RNA comprises one of base sequences SEQ ID NO: 107 or 108 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 107 or 108 and has a length from 21-36 nucleotides, more preferably 21, 22, 23, 24, 25, 26, 27, 28, 29, 30, 31, 32, 33, 34, 35 or 36 nucleotides. Even more preferred oligonucleotide consists of 2'-O-methyl phosphorothioate RNA, has a base sequence that consists of one of the base sequences SEQ ID NO: 107 or 108 and has a length of 21 nucleotides.

Most preferred oligonucleotide consists of 2'-O-methyl phosphorothioate RNA, has a base sequence that consists of one of the base sequences SEQ ID NO: 107 or 108, has a length of 21 nucleotides and additionally comprises 4 abasic monomers at one of its termini, preferably at the 3' terminus. Said most preferred oligonucleotide is represented by a base sequence consisting of SEQ ID NO: 220 or 221.

A preferred oligonucleotide comprising or consisting of 2'-O-methyl phosphorothioate RNA comprises one of base sequences SEQ ID NO: 109 or 110 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 109 or 110 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 109 or 110 and has a length of 24 nucleotides.

A preferred oligonucleotide comprising or consisting of 2'-O-methyl phosphorothioate RNA comprises one of base sequences SEQ ID NO: 111 or 112 and has a length from 27-36 nucleotides, more preferably 27, 28, 29, 30, 31, 32, 33, 34, 35 or 36 nucleotides.

An even more preferred oligonucleotide consists of 2'-O-methyl phosphorothioate RNA and comprises one of the base sequences SEQ ID NO: 111 or 112 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 111 or 112 and has a length of 27 nucleotides.

A preferred oligonucleotide comprising or consisting of 2'-O-methyl phosphorothioate RNA comprises one of base sequences SEQ ID NO: 113 or 114 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 113 or 114 and has a length from 30-36 nucleotides, more preferably 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 113 or 114 and has a length of 30 nucleotides.

A preferred oligonucleotide comprising or consisting of 2'-O-methyl phosphorothioate RNA comprises one of base sequences SEQ ID NO: 115 or 116 and has a length from 33-36 nucleotides, more preferably 33, 34, 35 or 36 nucleotides. An even more preferred oligonucleotide consists of 2'-O-methyl phosphorothioate RNA and comprises one of the base sequences SEQ ID NO: 115 or 116 and has a length from 33-36 nucleotides, more preferably 33, 34, 35 or 36 nucleotides. Most preferred oligonucleotide consists of 2'-O-methyl phosphorothioate RNA, has a base sequence that consists of one of the base sequences SEQ ID NO: 115 or 116 and has a length of 33 nucleotides.

A preferred oligonucleotide comprising or consisting of 2'-O-methyl phosphorothioate RNA comprises one of base sequences SEQ ID NO: 117 or 118 and has a length of 36 nucleotides. Most preferred oligonucleotide consists of 2'-O-methyl phosphorothioate RNA, has a base sequence that consists of one of the base sequences SEQ ID NO: 117 or 118 and has a length of 36 nucleotides.

In another embodiment, an antisense oligonucleotide comprising or consisting of 2'-O-methyl phosphorothioate RNA, and comprising a 5-methylcytosine is represented by a nucleotide sequence comprising or consisting of a sequence that binds to (or is able to bind to), hybridizes (or is able to hybridize), targets and/or is reverse complementary to a $(GCG)_n$ repeat in a transcript and is particularly useful for the treatment, delay, amelioration and/or prevention of the human genetic diseases: infantile spasm syndrome, deidocranial dysplasia, blepharophimosis, hand-foot-genital disease, synpolydactyly, oculopharyngeal muscular dystrophy and/or holoprosencephaly, which are caused by repeat expansions in the ARX, CBFA1, FOXL2, HOXA13, HOXD13, OPDM/PABP2, TCFBR1 or ZIC2 genes. Preferably, these genes are from human origin.

In a preferred embodiment, an oligonucleotide defined as being reverse complementary to, binding (or being able to bind), hybridizing (or being able to hybridize) or targeting a $(GCG)_n$ repeat comprises or consists of a repetitive nucleotide unit $(XGX)_m$ and has a length comprised from 12 to 36 nucleotides and wherein each X is C or 5-methylcytosine, such that at least one X is 5-methylcytosine. m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit $(XGX)_m$, wherein at least one X is 5-methylcytosine, and m is an integer from 4 to 12 (SEQ ID NO: 13 to 21). An even more preferred oligonucleotide comprises or consists of a repetitive nucleotide unit $(XGX)_m$, wherein each X is 5-methylcytosine, and m is an integer from 4 to 12 (SEQ ID NO: 13 to 21).

An even more preferred oligonucleotide therefore comprises or consists of a repetitive nucleotide unit $(XGX)_7$ (SEQ ID NO: 16), wherein at least one X is 5-methylcytosine.

An even more preferred oligonucleotide comprises or consists of a repetitive nucleotide unit $(XGX)_7$ (SEQ ID NO: 16), wherein each X is 5-methylcytosine.

Most preferred oligonucleotides sequences comprising or consisting of a repetitive nucleotide unit $(XGX)_m$ have been identified in table 2 as SEQ ID NO:119-132.

A preferred oligonucleotide comprising or consisting of 2'-O-methyl phosphorothioate RNA comprises one of base sequences SEQ ID NO: 119 or 120 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 119 or 120 and has a length from 16-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 119 or 120 and has a length of 12 nucleotides.

A preferred oligonucleotide comprising or consisting of 2'-O-methyl phosphorothioate RNA comprises one of base sequences SEQ ID NO: 121 or 122 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 90-106 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 121 or 122 and has a length of 15 nucleotides.

A preferred oligonucleotide comprising or consisting of 2'-O-methyl phosphorothioate RNA comprises one of base sequences SEQ ID NO: 123 or 124 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 123 or 124 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 123 or 124 and has a length of 18 nucleotides.

A preferred oligonucleotide comprising or consisting of 2'-O-methyl phosphorothioate RNA comprises one of base sequences SEQ ID NO: 125 or 126 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 125 or 126 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 125 or 126 and has a length of 21 nucleotides. A preferred oligonucleotide comprising or consisting of 2'-O-methyl phosphorothioate RNA comprises one of base sequences SEQ ID NO: 127 or 128 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 127 or 128 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 127 or 128 and has a length of 24 nucleotides.

A preferred oligonucleotide comprising or consisting of 2'-O-methyl phosphorothioate RNA comprises one of base sequences SEQ ID NO: 129 or 130 and has a length from 27-36 nucleotides, more preferably 27, 28, 29, 30, 31, 32, 33, 34, 35 or 36 nucleotides.

An even more preferred oligonucleotide consists of 2'-O-methyl phosphorothioate RNA and comprises one of the base sequences SEQ ID NO: 129 or 130 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 129 or 130 and has a length of 27 nucleotides.

A preferred oligonucleotide comprising or consisting of 2'-O-methyl phosphorothioate RNA comprises one of base sequences SEQ ID NO: 131 or 132 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 131 or 132 and has a length from 30-36 nucleotides, more preferably 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 131 or 132 and has a length of 30 nucleotides.

In another embodiment, an oligonucleotide comprising or consisting of 2'-O-methyl phosphorothioate RNA and comprising a 5-methylcytosine, is represented by a nucleotide sequence comprising or consisting of a sequence that binds (or is able to bind), targets, hybridizes (or is able to hybridize) and/or is reverse complementary to a $(CGG)_n$ repeat in a transcript and is particularly useful for the treatment, delay, amelioration and/or prevention of human fragile X syndromes, caused by repeat expansion in the FMR1 gene. Preferably, these genes are from human origin.

In a preferred embodiment, an oligonucleotide defined as being reverse complementary to, binding (or is able to bind), hybridizing (or is able to hybridize) or targeting a $(CGG)_n$ repeat comprises or consists of a repetitive nucleotide unit $(XXG)_m$ and has a length comprised from 12 to 36 nucleotides and wherein each X is C or 5-methylcytosine, such that at least one X is 5-methylcytosine.

m is an integer. In the context of this embodiment, m may be 4, 5, 6, 7, 8, 9, 10, 11, 12.

A preferred value for m is 7.

A more preferred oligonucleotide therefore comprises or consists of a repetitive nucleotide unit $(XXG)_m$, wherein each X is C or 5-methylcytosine, such that at least one X is 5-methylcytosine, and m is an integer from 4 to 12 (SEQ ID NO: 22 to 30).

An even more preferred oligonucleotide comprises or consists of a repetitive nucleotide unit $(XXG)_m$, wherein each X is 5-methylcytosine, and m is an integer from 4 to 12 (SEQ ID NO: 22 to 30).

An even more preferred oligonucleotide therefore comprises or consists of a repetitive nucleotide unit $(XXG)_7$ (SEQ ID NO: 25), wherein each X is C or 5-methylcytosine, such that at least one X is 5-methylcytosine.

An even more preferred oligonucleotide comprises or consists of a repetitive nucleotide unit $(XXG)_7$ (SEQ ID NO: 25), wherein each X is 5-methylcytosine.

Most preferred oligonucleotides sequences comprising or consisting of a repetitive nucleotide unit $(XXG)_m$ have been identified in table 2 as SEQ ID NO: 133-146.

A preferred oligonucleotide comprising or consisting of 2'-O-methyl phosphorothioate RNA comprises one of base sequences SEQ ID NO: 133 or 134 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 133 or 134 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 133 or 134 and has a length of 12 nucleotides.

A preferred oligonucleotide comprising or consisting of 2'-O-methyl phosphorothioate RNA comprises one of base sequences SEQ ID NO: 135 or 136 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 135 or 136 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 135 or 136 and has a length of 15 nucleotides.

A preferred oligonucleotide comprising or consisting of 2'-O-methyl phosphorothioate RNA comprises one of base sequences SEQ ID NO: 137 or 138 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 137 or 138 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 137 or 138 and has a length of 18 nucleotides.

A preferred oligonucleotide comprising or consisting of 2'-O-methyl phosphorothioate RNA comprises one of base sequences SEQ ID NO: 139 or 140 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 139 or 140 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 139 or 140 and has a length of 21 nucleotides. A preferred oligonucleotide comprising or consisting of 2'-O-methyl phosphorothioate RNA comprises one of base sequences SEQ ID NO: 141 or 142 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 141 or 142 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 141 or 142 and has a length of 24 nucleotides.

A preferred oligonucleotide comprising or consisting of 2'-O-methyl phosphorothioate RNA comprises one of base sequences SEQ ID NO: 143 or 144 and has a length from 27-36 nucleotides, more preferably 27, 28, 29, 30, 31, 32, 33, 34, 35 or 36 nucleotides.

An even more preferred oligonucleotide consists of 2'-O-methyl phosphorothioate RNA and comprises one of the base sequences SEQ ID NO: 143 or 144 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 143 or 144 and has a length of 27 nucleotides.

A preferred oligonucleotide comprising or consisting of 2'-O-methyl phosphorothioate RNA comprises one of base sequences SEQ ID NO: 145 or 146 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 145 or 146 and has a length from 30-36 nucleotides, more preferably 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 145 or 146 and has a length of 30 nucleotides.

In another embodiment, an oligonucleotide comprising or consisting of 2'-O-methyl phosphorothioate RNA and comprising a 5-methylcytosine and/or a 5-methyluracil, is represented by a nucleotide sequence comprising or consisting of a sequence that binds (or is able to bind), targets, hybridizes (or is able to hybridize) and/or is reverse complementary to a $(GAA)_n$ repeat in a transcript and is particularly useful for the treatment, delay and/or prevention of the human genetic disorder Friedreich's ataxia.

In a preferred embodiment, an oligonucleotide defined as being reverse complementary to, binding (or being able to bind), hybridizing (or being able to hybridize) or targeting a $(GAA)_n$ repeat comprises or consists of a repetitive nucleotide unit $(YYX)_m$ and has a length comprised from 12 to 36 nucleotides and wherein each X is C or 5-methylcytosine, and each Y is U or 5-methyluracil such that at least one X is 5-methylcytosine and/or at least one Y is 5-methyluracil. m is an integer. In the context of this embodiment, m may be 4, 5, 6, 7, 8, 9, 10, 11, 12.

A preferred value for m is 7.

A more preferred oligonucleotide therefore comprises or consists of a repetitive nucleotide unit $(YYX)_m$, wherein each X is C or 5-methylcytosine, and each Y is U or 5-methyluracil such that at least one X is 5-methylcytosine and/or at least one Y is 5-methyluracil, and m is an integer from 4 to 12 (SEQ ID NO: 31 to 39).

An even more preferred oligonucleotide comprises or consists of a repetitive nucleotide unit $(YYX)_m$, wherein each X is 5-methylcytosine, and/or each Y is 5-methyluracil, and m is an integer from 4 to 12 (SEQ ID NO: 31 to 39).

An even more preferred oligonucleotide therefore comprises or consists of a repetitive nucleotide unit $(YYX)_7$ (SEQ ID NO: 34), wherein each X is C or 5-methylcytosine, and each Y is U or 5-methyluracil such that at least one X is 5-methylcytosine and/or at least one Y is 5-methyluracil.

An even more preferred oligonucleotide comprises or consists of a repetitive nucleotide unit $(YYX)_7$ (SEQ ID NO: 34), wherein each X is 5-methylcytosine, and/or each Y is 5-methyluracil.

Most preferred oligonucleotides sequences comprising or consisting of a repetitive nucleotide unit $(XYG)_m$ have been identified in table 2 as SEQ ID NO: 147-167.

A preferred oligonucleotide comprising or consisting of 2'-O-methyl phosphorothioate RNA comprises one of base sequences SEQ ID NO: 147 or 148 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 147 or 148 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 147 or 148 and has a length of 12 nucleotides.

A preferred oligonucleotide comprising or consisting of 2'-O-methyl phosphorothioate RNA comprises one of base sequences SEQ ID NO: 149 or 150 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 149 or 150 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 149 or 150 and has a length of 15 nucleotides.

A preferred oligonucleotide comprising or consisting of 2'-O-methyl phosphorothioate RNA comprises one of base sequences SEQ ID NO: 151 or 152 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 151 or 152 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 151 or 152 and has a length of 18 nucleotides.

A preferred oligonucleotide comprising or consisting of 2'-O-methyl phosphorothioate RNA comprises one of base sequences SEQ ID NO: 153-157 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 153-157 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 153-157 and has a length of 21 nucleotides.

A preferred oligonucleotide comprising or consisting of 2'-O-methyl phosphorothioate RNA comprises one of base sequences SEQ ID NO: 158 or 159 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 158 or 159 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 158 or 159 and has a length of 24 nucleotides.

A preferred oligonucleotide comprising or consisting of 2'-O-methyl phosphorothioate RNA comprises one of base sequences SEQ ID NO: 160 or 161 and has a length from 27-36 nucleotides, more preferably 27, 28, 29, 30, 31, 32, 33, 34, 35 or 36 nucleotides.

An even more preferred oligonucleotide consists of 2'-O-methyl phosphorothioate RNA and comprises one of the base sequences SEQ ID NO: 160 or 161 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 160 or 161 and has a length of 27 nucleotides.

A preferred oligonucleotide comprising or consisting of 2'-O-methyl phosphorothioate RNA comprises one of base sequences SEQ ID NO: 162 or 163 and has a length from 30-36 nucleotides, more preferably 30, 31, 32, 33, 34, 35 or 36 nucleotides. An even more preferred oligonucleotide consists of 2'-O-methyl phosphorothioate RNA and comprises one of the base sequences SEQ ID NO: 162 or 163 and has a length from 30-36 nucleotides, more preferably 30, 31, 32, 33, 34, 35 or 36 nucleotides. Most preferred oligonucleotide consists of 2'-O-methyl phosphorothioate RNA, has a base sequence that consists of one of the base sequences SEQ ID NO: 162 or 163 and has a length of 30 nucleotides.

A preferred oligonucleotide comprising or consisting of 2'-O-methyl phosphorothioate RNA comprises one of base sequences SEQ ID NO: 164 or 165 and has a length from 33-36 nucleotides, more preferably 33, 34, 35 or 36 nucleotides. An even more preferred oligonucleotide consists of 2'-O-methyl phosphorothioate RNA and comprises one of the base sequences SEQ ID NO: 164 or 165 and has a length from 33-36 nucleotides, more preferably 33, 34, 35 or 36 nucleotides. Most preferred oligonucleotide consists of 2'-O-methyl phosphorothioate RNA, has a base sequence that consists of one of the base sequences SEQ ID NO: 164 or 165 and has a length of 33 nucleotides.

A preferred oligonucleotide comprising or consisting of 2'-O-methyl phosphorothioate RNA comprises one of base sequences SEQ ID NO: 166 or 167 and has a length of 36 nucleotides. An even more preferred oligonucleotide consists of 2'-O-methyl phosphorothioate RNA and has a base sequence that consists one of the base sequences SEQ ID NO: 166 or 167 and has a length of 36 nucleotides.

In another embodiment, an antisense oligonucleotide comprising or consisting of 2'-O-methyl phosphorothioate RNA and comprising a 5-methylcytosine, is represented by a nucleotide sequence comprising or consisting of a sequence that binds to (or is able to bind), hybridizes (or is able to hybridize), targets and/or is reverse complementary to a $(CCG)_n$ or $(GCC)_n$ repeat in a transcript and is particularly useful for the treatment, delay, amelioration and/or prevention of the human genetic disorder fragile XE mental retardation, caused by repeat expansion in the FMR2 gene. Preferably, these genes are from human origin.

In a preferred embodiment, an oligonucleotide defined as being reverse complementary to, binding (or being able to bind), hybridizing (or being able to hybridize) or targeting a $(CCG)_n$ repeat comprises or consists of a repetitive nucleotide unit $(XGG)_m$ or $(GGX)_m$ and has a length comprised from 12 to 36 nucleotides and wherein each X is C or 5-methylcytosine. m is an integer. In the context of this embodiment, m may be 4, 5, 6, 7, 8, 9, 10, 11, 12. A preferred value for m is 7.

A more preferred oligonucleotide therefore comprises or consists of a repetitive nucleotide unit $(XGG)_m$ or $(GGX)_m$, wherein each X is C or 5-methylcytosine, and m is an integer from 4 to 12 (SEQ ID NO: 49 to 57) or (SEQ ID NO: 40 to 48).

An even more preferred oligonucleotide comprises or consists of a repetitive nucleotide unit $(XGG)_m$ or $(GGX)_m$, wherein each X is 5-methylcytosine, and m is an integer from 4 to 12 (SEQ ID NO: 49 to 57) or (SEQ ID NO: 40 to 48).

An even more preferred oligonucleotide therefore comprises or consists of a repetitive nucleotide unit $(XGG)_7$ (SEQ ID NO: 52) or $(GGX)_7$ (SEQ ID NO: 43), wherein each X is C or 5-methylcytosine.

An even more preferred oligonucleotide comprises or consists of a repetitive nucleotide unit $(XGG)_7$ (SEQ ID NO: 52) or $(GGX)_7$ (SEQ ID NO: 43), wherein each X is 5-methylcytosine.

Most preferred oligonucleotides sequences comprising or consisting of a repetitive nucleotide unit $(GGX)_m$ have been identified in table 2 as SEQ ID NO: 168-177.

A preferred oligonucleotide comprising or consisting of 2'-O-methyl phosphorothioate RNA comprises base sequence SEQ ID NO: 168 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequences SEQ ID NO: 168 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequences SEQ ID NO: 168 and has a length of 12 nucleotides.

A preferred oligonucleotide comprising or consisting of 2'-O-methyl phosphorothioate RNA comprises base sequence SEQ ID NO: 169 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 169 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 169 and has a length of 15 nucleotides.

A preferred oligonucleotide comprising or consisting of 2'-O-methyl phosphorothioate RNA comprises base sequence SEQ ID NO: 170 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 170 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 170 and has a length of 18 nucleotides.

A preferred oligonucleotide comprising or consisting of 2'-O-methyl phosphorothioate RNA comprises one of base sequences SEQ ID NO: 171-174 has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 171-174 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 171-174 and has a length of 21 nucleotides.

A preferred oligonucleotide comprising or consisting of 2'-O-methyl phosphorothioate RNA comprises base sequence SEQ ID NO: 175 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 175 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 175 and has a length of 24 nucleotides.

A preferred oligonucleotide comprising or consisting of 2'-O-methyl phosphorothioate RNA comprises base sequence SEQ ID NO: 176 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 176 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 176 and has a length of 27 nucleotides.

A preferred oligonucleotide comprising or consisting of 2'-O-methyl phosphorothioate RNA comprises base sequence SEQ ID NO: 177 and has a length from 30-36 nucleotides, more preferably 30, 31, 32, 33, 34, 35 or 36 nucleotides. An even more preferred oligonucleotide consists of 2'-O-methyl phosphorothioate RNA and comprises base sequence SEQ ID NO: 177 and has a length from 30-36 nucleotides, more preferably 30, 31, 32, 33, 34, 35 or 36 nucleotides. Most preferred oligonucleotide consists of 2'-O-methyl phosphorothioate RNA, has its base sequence that consists of base sequence SEQ ID NO: 177 and has a length of 30 nucleotides.

Most preferred oligonucleotides sequences comprising or consisting of a repetitive nucleotide unit $(XGG)_m$ have been identified in table 2 as SEQ ID NO: 178-184.

A preferred oligonucleotide comprising or consisting of 2'-O-methyl phosphorothioate RNA comprises base sequence SEQ ID NO: 178 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 178 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 178 and has a length of 12 nucleotides.

A preferred oligonucleotide comprising or consisting of 2'-O-methyl phosphorothioate RNA comprises base sequence SEQ ID NO: 179 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 179 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 179 and has a length of 15 nucleotides.

A preferred oligonucleotide comprising or consisting of 2'-O-methyl phosphorothioate RNA comprises base sequences SEQ ID NO: 180 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 180 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 180 and has a length of 18 nucleotides.

A preferred oligonucleotide comprising or consisting of 2'-O-methyl phosphorothioate RNA comprises base sequence SEQ ID NO: 181 and has a length from 21-36 nucleotides, more preferably 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 181 and has a length from 21-36 nucleotides, more preferably 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 181 and has a length of 21 nucleotides.

A preferred oligonucleotide comprising or consisting of 2'-O-methyl phosphorothioate RNA comprises base sequence SEQ ID NO: 182 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 182 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 182 and has a length of 24 nucleotides.

A preferred oligonucleotide comprising or consisting of 2'-O-methyl phosphorothioate RNA comprises base sequence SEQ ID NO: 183 and has a length from 27-36 nucleotides, more preferably 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 183 and has a length from 27-36 nucleotides, more preferably 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 183 and has a length of 27 nucleotides.

A preferred oligonucleotide comprising or consisting of 2'-O-methyl phosphorothioate RNA comprises base sequence SEQ ID NO: 184 and has a length from 30-36 nucleotides, more preferably 30, 31, 32, 33, 34, 35 or 36 nucleotides. An even more preferred oligonucleotide consists of 2'-O-methyl phosphorothioate RNA and comprises base sequence SEQ ID NO: 184 and has a length from 30-36 nucleotides, more preferably 30, 31, 32, 33, 34, 35 or 36 nucleotides. Most preferred oligonucleotide consists of 2'-O-methyl phosphorothioate RNA, has its base sequence that consists of base sequence SEQ ID NO: 184 and has a length of 30 nucleotides.

In another embodiment, an oligonucleotide comprising or consisting of 2'-O-methyl phosphorothioate RNA and comprising a 5-methylcytosine and/or a 2,6-diaminopurine, is represented by a nucleotide sequence comprising or consisting of a sequence that binds (or is able to bind), hybridizes (or is able to hybridize), targets and/or is reverse complementary to a $(CCUG)_n$ repeat in a transcript and is particularly useful for the treatment, delay and/or prevention of the human genetic disorder myotonic dystrophy type 2 (DM2), caused by repeat expansions in the DM2/ZNF9 gene. Preferably, these genes are from human origin.

In a preferred embodiment, an oligonucleotide defined as being reverse complementary to, binding (or being able to bind), hybridizing (or being able to hybridize) or targeting a $(CCUG)_n$ repeat comprises or consists of a repetitive nucleotide unit $(XZGG)_m$ and has a length comprised from 12 to 36 nucleotides and wherein each X is C or 5-methylcytosine, and each Z is A or 2,6-diaminopurine such that at least one X is 5-methylcytosine and/or at least one Z is 2,6-diaminopurine.

m is an integer. In the context of this embodiment, m may be 3, 4, 5, 6, 7, 8, 9. A preferred value for m is 5.

A more preferred oligonucleotide therefore comprises or consists of a repetitive nucleotide unit $(XZGG)_m$, wherein each X is C or 5-methylcytosine, and each Z is A or 2,6-diaminopurine such that at least one X is 5methylcytosine and/or at least one A is 2,6-diaminopurine, and m is an integer from 3 to 9 (SEQ ID NO: 63 to 69).

An even more preferred oligonucleotide comprises or consists of a repetitive nucleotide unit $(XZGG)_m$, wherein each X is 5-methylcytosine, and/or each Z is 2,6-diaminopurine, and m is an integer from 3 to 9 (SEQ ID NO: 63 to 69).

An even more preferred oligonucleotide therefore comprises or consists of a repetitive nucleotide unit $(XZGG)_5$ (SEQ ID NO: 65), wherein each X is C or 5-methylcytosine, and each Z is A or 2,6-diaminopurine such that at least one X is 5-methylcytosine and/or at least one Z is 2,6-diaminopurine.

An even more preferred oligonucleotide comprises or consists of a repetitive nucleotide unit $(XZGG)_5$ (SEQ ID NO: 65), wherein each X is 5-methyl-cytosine, and/or each Z is 2,6-diaminopurine.

Most preferred oligonucleotides sequences comprising or consisting of a repetitive nucleotide unit $(XZGG)_m$ have been identified in table 2 as SEQ ID NO: 193-208.

A preferred oligonucleotide comprising or consisting of 2'-O-methyl phosphorothioate RNA comprises one of base sequences SEQ ID NO: 193 or 194 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 193 or 194 and has a length from 12-36 nucleotides, more preferably 12, 13, 14, 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 193 or 194 and has a length of 12 nucleotides.

A preferred oligonucleotide comprising or consisting of 2'-O-methyl phosphorothioate RNA comprises one of base sequences SEQ ID NO: 195 or 196 and has a length from 16-36 nucleotides, more preferably 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 195 or 196 and has a length from 16-36 nucleotides, more preferably 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 195 or 196 and has a length of 16 nucleotides.

A preferred oligonucleotide comprising or consisting of 2'-O-methyl phosphorothioate RNA comprises one of base sequences SEQ ID NO: 197-200 and has a length from 20-36 nucleotides, more preferably 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 197-200 and has a length from 20-36 nucleotides, more preferably 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 197-200 and has a length of 20 nucleotides.

A preferred oligonucleotide comprising or consisting of 2'-O-methyl phosphorothioate RNA comprises one of base sequences SEQ ID NO: 201 or 202 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 201 or 202 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 201 or 202 and has a length of 24 nucleotides.

A preferred oligonucleotide comprising or consisting of 2'-O-methyl phosphorothioate RNA comprises one of base sequences SEQ ID NO: 203 or 204 and has a length from 28-36 nucleotides, more preferably 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 203 or 204 and has a length from 28-36 nucleotides, more preferably 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 203 or 204 and has a length of 28 nucleotides.

A preferred oligonucleotide comprising or consisting of 2'-O-methyl phosphorothioate RNA comprises one of base sequences SEQ ID NO: 205 or 206 and has a length from 32-36 nucleotides, more preferably 32, 33, 34, 35 or 36 nucleotides. An even more preferred oligonucleotide consists of 2'-O-methyl phosphorothioate RNA and comprises one of the base sequences SEQ ID NO: 205 or 206 and has a length from 32-36 nucleotides, more preferably 32, 33, 34, 35 or 36 nucleotides. Most preferred oligonucleotide consists of 2'-O-methyl phosphorothioate RNA, has its base sequence that consists of one of the base sequences SEQ ID NO: 205 or 206 and has a length of 32 nucleotides.

A preferred oligonucleotide comprising or consisting of 2'-O-methyl phosphorothioate RNA comprises one of base sequences SEQ ID NO: 207 or 208 and has a length of 36 nucleotides. An even more preferred oligonucleotide consists of 2'-O-methyl phosphorothioate RNA and has its base sequence that consists of one of the base sequences SEQ ID NO: 207 or 208 and has a length of 36 nucleotides.

In another embodiment, an oligonucleotide comprising or consisting of 2'-O-methyl phosphorothioate RNA and comprising a 5-methyluracil and/or a 2,6-diaminopurine, is represented by a nucleotide sequence comprising or consisting of a sequence that binds (or is able to bind), hybridizes (or is able to hybridize), targets and/or is reverse complementary to a $(AUUCU)_n$ repeat in an intron and is particularly useful for the treatment, delay, amelioration and/or prevention of the human genetic disorder spinocerebellar ataxia type 10 (SCA10). Preferably, this gene is from human origin. In a preferred embodiment, an oligonucleotide defined as being reverse complementary to, binding (or being able to bind), hybridizing (or being able to hybridize) or targeting a $(AUUCU)_n$ repeat comprises or consists of a repetitive nucleotide unit $(ZGZZY)_m$ and has a length comprised from 12 to 36 nucleotides and wherein each Y is U or 5-methyluracil, and each Z is A or 2,6-diaminopurine such that at least one Y is 5-methyluracil and/or at least one Z is 2,6-diaminopurine.

m is an integer. In the context of this embodiment, m may be 3, 4, 5, 6, 7. A preferred value for m is 4.

A more preferred oligonucleotide therefore comprises or consists of a repetitive nucleotide unit $(ZGZZY)_m$, wherein each Y is U or 5-methyluracil, and each Z is A or 2,6-diaminopurine such that at least one Y is 5-methyluracil and/or at least one Z is 2,6-diaminopurine, and m is an integer from 3 to 7 (SEQ ID NO: 58 to 62).

An even more preferred oligonucleotide comprises or consists of a repetitive nucleotide unit $(ZGZZY)_m$, wherein each Y is 5-methyluracil, and/or each Z is 2,6-diaminopurine, and m is an integer from 3 to 7 (SEQ ID NO: 58 to 62).

An even more preferred oligonucleotide therefore comprises or consists of a repetitive nucleotide unit $(ZGZZY)_4$ (SEQ ID NO: 59), wherein each Y is C or 5-methyluracil, and each Z is A or 2,6-diaminopurine such that at least one Y is 5-methyluracil and/or at least one Z is 2,6-diaminopurine.

An even more preferred oligonucleotide comprises or consists of a repetitive nucleotide unit $(ZGZZY)_4$ (SEQ ID NO: 59), wherein each Y is 5-methyluracil, and/or each Z is 2,6-diaminopurine.

Most preferred oligonucleotides sequences comprising or consisting of a repetitive nucleotide unit $(ZGZZY)_m$ have been identified in table 2 as SEQ ID NO:185-192.

A preferred oligonucleotide comprising or consisting of 2'-O-methyl phosphorothioate RNA comprises base sequence SEQ ID NO: 185 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 185 and has a length from 15-36 nucleotides, more preferably 15, 16, 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 185 and has a length of 15 nucleotides.

A preferred oligonucleotide comprising or consisting of 2'-O-methyl phosphorothioate RNA comprises one of base sequences SEQ ID NO: 186-189 and has a length from 20-36 nucleotides, more preferably 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 186-189 and has a length from 20-36 nucleotides, more preferably 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 186-189 and has a length of 20 nucleotides.

A preferred oligonucleotide comprising or consisting of 2'-O-methyl phosphorothioate RNA comprises base sequence SEQ ID NO: 190 and has a length from 25-36 nucleotides, more preferably 25, 26, 27, 28, 29, 30, 31, 32, 33, 34, 35 or 36 nucleotides.

An even more preferred oligonucleotide consists of 2'-O-methyl phosphorothioate RNA and comprises base sequence SEQ ID NO: 190 and has a length from 25-36 nucleotides, more preferably 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 190 and has a length of 25 nucleotides.

A preferred oligonucleotide comprising or consisting of 2'-O-methyl phosphorothioate RNA comprises base sequence SEQ ID NO: 191 and has a length from 30-36 nucleotides, more preferably 30, 31, 32, 33, 34, 35 or 36 nucleotides. An even more preferred oligonucleotide consists of 2'-O-methyl phosphorothioate RNA and comprises base sequence SEQ ID NO: 191 and has a length from 30-36 nucleotides, more preferably 30, 31, 32, 33, 34, 35 or 36 nucleotides. Most preferred oligonucleotide consists of 2'-O-methyl phosphorothioate RNA, has its base sequence that consists of base sequence SEQ ID NO: 191 and has a length of 30 nucleotides.

A preferred oligonucleotide comprising or consisting of 2'-O-methyl phosphorothioate RNA comprises base sequence SEQ ID NO: 192 and has a length from 35-36 nucleotides, more preferably 35 or 36 nucleotides. An even more preferred oligonucleotide consists of 2'-O-methyl phosphorothioate RNA and comprises base sequence SEQ ID NO: 192 and has a length from 35-36 nucleotides, more preferably 35 or 36 nucleotides. Most preferred oligonucleotide consists of 2'-O-methyl phosphorothioate RNA, has its base sequence that consists of base sequence SEQ ID NO: 192 and has a length of 35 nucleotides.

In another embodiment, an oligonucleotide comprising or consisting of 2'-O-methyl phosphorothioate RNA and comprising a 5-methylcytosine and/or a abasic monomer, and/or a inosine, is represented by a nucleotide sequence comprising or consisting of a sequence that binds (or is able to bind), hybridizes (or is able to hybridize), targets and/or is reverse complementary to a $(GGGGCC)_n$ repeat present in a C9ORF72 human transcript and is particularly useful for the treatment, delay, amelioration and/or prevention of the human genetic disorder amylotrophic lateral sclerosis (ALS) or frontotemporal dementia (FTD). Preferably, this gene is from human origin.

In a preferred embodiment, an oligonucleotide defined as being reverse complementary to, binding (or being able to bind), hybridizing (or being able to hybridize) or targeting a $(GGGGCC)_n$ repeat comprises or consists of a repetitive nucleotide unit $(GGXUXX)_m$, $(GGXQXX)_m$, $(GGXIXX)_m$, or $(GGCCUC)_m$, and has a length comprised from 17 to 36 nucleotides and wherein each X is C or 5-methylcytosine such that at least one X is 5-methylcytosine, wherein each Q is an abasic monomer, wherein each I is an inosine, and wherein m is an integer. In the context of this embodiment, m may be 3, 4, 5, 6, 7. A preferred value for m is 3 or 4.

More preferably, said oligonucleotide comprises or consists of a repetitive nucleotide unit SEQ ID NO: 216-219 as defined in table 1. Even more preferred oligonucleotides sequences comprising or consisting of a repetitive nucleotide unit $(GGXUXX)_m$, $(GGXQXX)_m$, $(GGXIXX)_m$, or $(GGCCUC)_m$, have been identified in table 2 as SEQ ID NO:209-215.

A preferred oligonucleotide comprising or consisting of 2'-O-methyl phosphorothioate RNA comprises one of base sequences SEQ ID NO: 209 or 211 and has a length from 17-36 nucleotides, more preferably 17, 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 209 or 211 and has a length from 17-36 nucleotides, more preferably 17, 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 209 or 211 and has a length of 17 or 18 nucleotides.

A preferred oligonucleotide comprising or consisting of 2'-O-methyl phosphorothioate RNA comprises base sequence SEQ ID NO: 210 and has a length from 18-36 nucleotides, more preferably 18, 19, 20, 21, 22, 23, 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 210 and has a length from 18-36 nucleotides, more preferably 18, 19, 20, 21, 22, 23, 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequence SEQ ID NO: 210 and has a length of 18 nucleotides.

A preferred oligonucleotide comprising or consisting of 2'-O-methyl phosphorothioate RNA comprises one of base sequences SEQ ID NO: 212 or 215 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises one of the base sequences SEQ ID NO: 212 or 215 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of one of the base sequences SEQ ID NO: 212 or 215 and has a length of 24 nucleotides.

A preferred oligonucleotide comprising or consisting of 2'-O-methyl phosphorothioate RNA comprises base sequence SEQ ID NO: 213 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 213 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequences SEQ ID NO: 213 and has a length of 24 nucleotides.

A preferred oligonucleotide comprising or consisting of 2'-O-methyl phosphorothioate RNA comprises base sequence SEQ ID NO: 214 and has a length from 24-36 nucleotides, more preferably 24, 25, 26, 27, 28, 29, 30, 31, 32, 33, 34, 35 or 36 nucleotides. An even more preferred oligonucleotide consists of 2'-O-methyl phosphorothioate RNA and comprises base sequence SEQ ID NO: 214 and has a length from 24-36 nucleotides, more preferably 24, 25, 26, 27, 28, 29, 30, 31, 32, 33, 34, 35 or 36 nucleotides. Most preferred oligonucleotide consists of 2'-O-methyl phosphorothioate RNA, has its base sequence that consists of base sequences SEQ ID NO: 214 and has a length of 24 nucleotides.

In an embodiment, an oligonucleotide preferably comprises or consists of 2'-O-methyl phosphorothioate RNA, comprises a 5-methylcytosine and/or a 5-methyluracil and/or a 2,6-diaminopurine base, is represented by a nucleotide sequence comprising or consisting of at least 12 to 36 consecutive nucleotides, said oligonucleotide targeting, hybridizing (or is able to hybridize), binding (or is able to bind) and/or being reverse complementary to a repeat as earlier defined herein More preferably, said nucleotide sequence comprising or consisting of at least 12 to 36 nucleotides, even more preferably 15 to 24, and most preferably 20 or 21 nucleotides. The length of said oligonucleotide may be 12, 13, 14, 15, 16, 17, 18, 19, 20, 21, 22, 23, 24, 25, 26, 27, 28, 29, 30, 31, 32, 33, 34, 35, or 36 nucleotides. Said oligonucleotide may be reverse complementary to and/or capable of hybridizing to and/or capable of targeting and/or capable of binding to a repeat in a coding region of a transcript, preferably a polyglutamine $(CAG)_n$ coding tract. Said oligonucleotide may also be reverse complementary to and/or capable of hybridizing to and/or capable of targeting and/or capable of binding to a non-coding region for instance 5' or 3' untranslated regions, or intronic sequences present in precursor RNA molecules.

In the context of the invention, the expression "capable of" may be replaced with "is able to".

In a second aspect, the present invention relates to an oligonucleotide, which comprises one or more abasic sites, as defined further below, at one or both termini. Preferably 1 to 10, more preferably 2, 3, 4, 5, 6, 7, 8, 9 or 10 and most preferably 4 abasic sites are present at a single terminus or at both termini of the oligonucleotide. One or more abasic sites may be present and both free termini of the oligonucleotide (5' and 3'), or at only one. The oligonucleotide according to this aspect of the invention preferably is represented by a nucleotide or a base sequence comprising or consisting of a sequence that binds (or is able to bind), hybridizes (or is able to hybridize), targets and/or is reverse complementary to a repetitive element in a RNA transcript selected from the $(CAG)_n$, $(GCG)_n$, $(CGG)_n$, $(GAA)_n$, $(GCC)_n$, $(CCG)_n$, $(AUUCU)_n$, $(GGGGCC)_n$ or $(CCUG)_n$, as indicated above. Said oligonucleotide is preferably a single stranded oligonucleotide, and may further optionally comprise any of the modifications as discussed herein, such as one or more base modifications, sugar modifications and/or backbone modifications, such as 5-methyl-C, 5-methyl-U, 2,6-diaminopurine, 2'-O-methyl, phosphorothioate, and combinations thereof. It is to be understood that in this aspect of the invention, these modification are not compulsory.

The oligonucleotide according to this aspect of the invention, comprising one or more abasic sites at one or both termini has an improved parameter over the oligonucleotides without such abasic sites. In this context, parameters may include: binding affinity and/or kinetics, silencing activity, allelic selectivity, biostability, (intra-tissue) distribution, cellular uptake and/or trafficking, and/or immunogenicity of said oligonucleotide, as explained earlier herein in connection with the improved parameter of an oligonucleotide of the invention of the first aspect. Each of the assays and definitions provided herein in connection with the improvement of a parameter of an oligonucleotide of the first aspect also hold for an oligonucleotide of the second aspect.

Below, an oligonucleotide comprising or consisting of 2'-O-methyl phosphorothioate RNA, comprising a 5-methylcytosine and/or a 5-methyluracil base and being represented by a nucleotide or a base sequence comprising $(CUG)_m$ and thus binding to (or being able to bind to), hybridizing (or being able to hybridize), targeting and/or being reverse complementary to $(CAG)_n$ is taken as an example to further illustrate the invention. Similar parameters defined in the context of such oligonucleotide could be defined by the skilled person for other oligonucleotides falling under the scope of the invention and binding to (or being able to bind to), hybridizing (or being able to hybridize), targeting and/or being reverse complementary to other repeats as identified herein. Other or similar symptoms may be identified by the skilled person concerning other diseases as identified herein.

In a preferred embodiment, in the context of the invention, an oligonucleotide as designed herein is able to delay and/or cure and/or treat and/or prevent and/or ameliorate a human genetic disorder as Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropallidoluysian atrophy (DRPLA) caused by CAG repeat expansions in the transcripts of a HTT (SEQ ID NO: 80), ATXN1 (SEQ ID NO: 81), ATXN2 (SEQ ID NO: 82) ATXN3 (SEQ ID NO: 83), CACNA1A (SEQ ID NO: 84), ATXN7 (SEQ ID NO: 85), PPP2R2B (SEQ ID NO: 86), TBP (SEQ ID NO: 87), AR (SEQ ID NO: 88), ATN1 (SEQ ID NO: 89) genes when this oligonucleotide is able to reduce or decrease the amount of (toxic) transcript of a diseased allele of a HTT, ATXN1, ATXN2 ATXN3, CACNA1A, ATXN7, PPP2R2B, TBP, AR or ATN1 gene in a cell of a patient, in a tissue of a patient and/or in a patient. In an embodiment, said HTT, ATXN1, ATXN2 ATXN3, CACNA1A, ATXN7, PPP2R2B, TBP, AR or ATN1 genes are human genes.

In the case of HD, an expanded CAG repeat region is present in exon 1 of the HTT gene in the genome of a patient. An expanded CAG repeat region may be defined herein as comprising a consecutive repetition of 38 to 180 repetitive units comprising a CAG trinucleotide, in a transcribed sequence of the HTT gene In the case of SCA1, an expanded CAG repeat region is present in exon 8 of the ATXN1 gene in the genome of a patient. An expanded CAG repeat region may be defined herein as comprising a consecutive repetition of 41 to 83 repetitive units comprising a CAG trinucleotide, in a transcribed sequence of the ATXN1 gene.

In the case of SCA2, an expanded CAG repeat region is present in exon 1 of the ATXN2 gene in the genome of a patient. An expanded CAG repeat region may be defined herein as comprising a consecutive repetition of 32 to 200 repetitive units comprising a CAG trinucleotide in a transcribed sequence of the ATXN2 gene.

In the case of SCA3, an expanded CAG repeat region is present in exon 8 of the ATXN3 gene in the genome of a patient. An expanded CAG repeat region may be defined herein as comprising a consecutive repetition of 52 to 86 repetitive units comprising a CAG trinucleotide in a transcribed sequence of the ATXN3 gene.

In the case of SCA6, an expanded CAG repeat region is present in exon 47 of the CACNA1A gene in the genome of a patient. An expanded CAG repeat region may be defined herein as comprising a consecutive repetition of 20 to 33 repetitive units comprising a CAG trinucleotide in a transcribed sequence of the CACNA1A gene.

In the case of SCA7, an expanded CAG repeat region is present in exon 3 of the ATXN7 gene in the genome of a patient. An expanded CAG repeat region may be defined herein as comprising a consecutive repetition of 36 to at least 460 repetitive units comprising a CAG trinucleotide in a transcribed sequence of the ATXN7 gene.

In the case of SCA12, an expanded CAG repeat region may be present in the 5' untranslated region (UTR), in an intron or within an open reading frame of the PPP2R2B gene in the genome of a patient. An expanded CAG repeat region may be defined herein as comprising a consecutive repetition of 66 to 78 repetitive units comprising a CAG trinucleotide in a transcribed sequence of the PPP2R2B gene.

In the case of SCA17, an expanded CAG repeat region is present in exon 3 of the TBP gene in the genome of a patient. An expanded CAG repeat region may be defined herein as comprising a consecutive repetition of 45 to 66 repetitive units comprising a CAG trinucleotide in a transcribed sequence of the TBP gene.

In the case of ALS or FTD, an expanded CAG repeat region is present in exon 1 of the ATXN2 gene in the genome of a patient. An expanded CAG repeat region may be defined herein as comprising a consecutive repetition of 27 to 33 repetitive units comprising a CAG trinucleotide in a transcribed sequence of the ATXN2 gene.

In the case of ALS or FTD, an expanded GGGGCC repeat region is present in the first intron of the C9ORF72 gene in the genome of a patient. An expanded GGGGCC repeat region may be defined as comprising a consecutive repetition of >30 repetitive units comprising a GGGGCC hexanucleotide in a transcribed sequence of the C9ORF72 gene.

In the case of SBMA, an expanded CAG repeat region is present in exon 1 of the AR gene in the genome of a patient. An expanded CAG repeat region may be defined herein as comprising a consecutive repetition of 40 repetitive units comprising a CAG trinucleotide in a transcribed sequence of the AR gene.

In the case of DRPLA, an expanded CAG repeat region is present in exon 5 of the ATN1 gene in the genome of a patient. An expanded CAG repeat region may be defined herein as comprising a consecutive repetition of 49 to 88 repetitive units comprising a CAG trinucleotide in a transcribed sequence of the ATN1 gene.

Throughout the invention, the term CAG repeat may be replaced by $(CAG)_n$, and vice versa, wherein n is an integer that may be 6 to 29 when the repeat is present in exon 1 of the HTT transcript of a healthy individual, 6 to 39 when the repeat is present in exon 8 of the ATXN1 gene of a healthy individual, less than 31 when the repeat is present in exon 1 of the ATXN2 gene of a healthy individual, 12 to 40 when the repeat is present in exon 8 of the ATXN3 gene of a healthy individual, less than 18 when the repeat is present in exon 47 of the CACNA1A gene of a healthy individual, 4 to 17 when the repeat is present in exon 3 of the ATXN7 gene of a healthy individual, 7 to 28 when the repeat is present in the 5'UTR of the PPP2R2B gene of a healthy individual, 25 to 42 when the repeat is present in exon 3 of the TBP gene of a healthy individual, 13 to 31 when the repeat is present in exon 1 of the AR gene of a healthy individual, 12 to 40 when the repeat is present in exon 8 of the ATXN3 gene of a healthy individual, or 6 to 35 when the repeat is present in exon 5 of the ATN1 gene of a healthy individual.

It preferably means that an oligonucleotide of the invention reduces a detectable amount of disease-associated or disease-causing or mutant transcript containing an extending or unstable number of CAG repeats in a cell of said patient, in a tissue of said patient and/or in a patient. Alternatively or in combination with previous sentence, said oligonucleotide may reduce the translation of said mutant transcript and thus the amount of mutant (toxic) protein. The reduction or decrease of the amount of expanded CAG repeat transcripts may be at least 1%, 5%, 10%, 15%, 20%, 25%, 30%, 35%, 40%, 45%, 50%, 55%, 60%, 65%, 70%, 75%, 80%, 85%, 90%, 95%, 100% by comparison to the amount of expanded CAG repeat transcripts before the treatment. Another parameter may be the decrease in $(CAG)_n$ transcript or of the quantity of said mutant transcript. This may be of at least 1%, 5%, 10%, 15%, 20%, 25%, 30%, 35%, 40%, 45%, 50%, 55%, 60%, 65%, 70%, 75%, 80%, 85%, 90%, 95%, 100% by comparison to the quantity of said transcript detected at the onset of the treatment The reduction or decrease may be assessed by Northern Blotting or Q-RT-PCR, preferably as carried out in the experimental part. An oligonucleotide of the invention may first be tested in the cellular system as described in Example 1 in the experimental part.

Alternatively or in combination with previous preferred embodiment, in the context of the invention, an oligonucleotide as designed herein is able to delay and/or cure and/or treat and/or prevent and/or ameliorate a human genetic disorder as Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropallidoluysian atrophy (DRPLA) caused by CAG repeat expansions in the transcripts of the HTT, ATXN1, ATXN2 ATXN3, CACNA1A, ATXN7, PPP2R2B, TBP, AR or ATN1 genes when this oligonucleotide is able to alleviate one or more symptom(s) and/or characteristic(s) and/or to improve a parameter linked with or associated with Huntington's disease (HD), spinocerebellar ataxia (SCA) type 1, 2, 3, 6, 7, 12 or 17, amyotrophic lateral sclerosis (ALS), frontotemporal dementia (FTD), X-linked spinal and bulbar muscular atrophy (SBMA) and/or dentatorubropalliduluysian atrophy (DRPLA) in an individual. An oligonucleotide as defined herein is able to improve one parameter or reduce a symptom or characteristic if after at least one week, one month, six month, one year or more of treatment using a dose of said oligonucleotide of the invention as identified herein said parameter is said to have been improved or said symptom or characteristic is said to have been reduced.

Improvement in this context may mean that said parameter had been significantly changed towards a value of said parameter for a healthy person and/or towards a value of said parameter that corresponds to the value of said parameter in the same individual at the onset of the treatment.

Reduction or alleviation in this context may mean that said symptom or characteristic had been significantly changed towards the absence of said symptom or characteristic which is characteristic for a healthy person and/or towards a change of said symptom or characteristic that corresponds to the state of the same individual at the onset of the treatment.

In this context, symptoms for Huntington's Disease are choreiform movements, progressive dementia and psychiatric manifestations (depression, psychosis, etc.). Choreiform movements consist of involuntary, rapid, irregular, jerky motor actions including facial twitching or writhing and twitching of distal extremities, and later more generalized forms that may impair gait (Ropper and Brown, 2005). Each of these symptoms may be assessed by the physician using known and described methods. A preferred method is monitoring of total functional capacity (TFC), a validated scale or symptom progression regarding the three main symptomatic areas of HD, measured by validated rating scales. These areas are specifically progression of motor signs, progression of neuropsychiatric symptoms and progression of cognitive decline. Another preferred scale therefore is the Unified HD Rating Scale (UHDRS; Huntington Study Group (Kieburtz K. et al. 1996; 11:136-142).

Huntington's disease (HD), spinocerebellar ataxia (SCA) type 1, 2, 3, 6, 7, or 17, X-linked spinal and bulbar muscular atrophy (SBMA) and dentatorubropallidoluysian atrophy (DRPLA) are all caused by CAG triplet repeat expansions in the coding region of the gene. Although the disease causing proteins in these diseases are different, in each case the resulting expanded stretch of glutamines results in a toxic-gain-of function of the protein and this leads to neurodegeneration. Protein aggregates are found in the nucleus and cytoplasm of cells, indicating that protein misfolding is a common feature of these disorders. A common preferred parameter is therefore (mutant) protein levels which can be determined by western blot analysis (Evers et al.), or the presence of protein aggregates in the nucleus and/or cytoplasm which can be monitored by in situ hybridization. An improvement of a HD parameter may be the decrease in the detection of the quantity or amount of protein aggregate. Such decrease may be at least 1%, 5%, 10%, 15%, 20%, 25%, 30%, 35%, 40%, 45%, 50%, 55%, 60%, 65%, 70%, 75%, 80%, 85%, 90%, 95%, 100% by comparison to the quantity or amount of protein aggregate before the onset of the treatment.

In the context of HD, various other proteins have been found to co-localize with htt aggregates, i.e. TATA box binding protein (TBP), CREB binding protein (CBP) and several molecular chaperones (Huang et al.; Muchowski et al.; Roon-Mom et al.; Steffan et al.). Also many affected cellular processes have been identified in HD, such as transcriptional de-regulation, mitochondrial dysfunction, and impaired vesicle transport, which may provide alternative parameters for HD (Bauer et al., 2009; Ross et al.). An improvement of each of these possible alternative HD parameters (i.e. TATA box binding protein (TBP), CREB binding protein (CBP) and several molecular chaperones) may be defined as for the improvement of protein aggregate as defined above.

Composition

In a second aspect, there is provided a composition comprising an oligonucleotide as described in the previous section entitled "Oligonucleotide". This composition preferably comprises or consists of or essentially consists of an oligonucleotide as described above.

As explained in the first aspect of the invention for ALS and FTD, it is known that at least two distinct repeats in at least two distinct transcripts may be involved in, responsible for, or linked with the disease. All preferred features relating to each of these oligonucleotides have been disclosed in the section entitled "oligonucleotide". In a preferred embodiment, said composition is for use as a medicament. Said composition is therefore a pharmaceutical composition. A pharmaceutical composition usually comprises a pharmaceutically accepted carrier, diluent and/or excipient. In a preferred embodiment, a composition of the current invention comprises a compound as defined herein and optionally further comprises a pharmaceutically acceptable formulation, filler, preservative, solubilizer, carrier, diluent, excipient, salt, adjuvant and/or solvent. Such pharmaceutically acceptable carrier, filler, preservative, solubilizer, diluent, salt, adjuvant, solvent and/or excipient may for instance be found in Remington: The Science and Practice of Pharmacy, 20th Edition. Baltimore, Md.: Lippincott Williams & Wilkins, 2000. The compound as described in the invention possesses at least one ionizable group. An ionizable group may be a base or acid, and may be charged or neutral. An ionizable group may be present as ion pair with an appropriate counterion that carries opposite charge(s). Examples of cationic counterions are sodium, potassium, cesium, Tris, lithium, calcium, magnesium, trialkylammonium, triethylammonium, and tetraalkylammonium. Examples of anionic counterions are chloride, bromide, iodide, lactate, mesylate, acetate, trifluoroacetate, dichloroacetate, and citrate. Examples of counterions have been described [e.g. Kumar L. et al, 2008, which is incorporated here in its entirety by reference].

A pharmaceutical composition may be further formulated to further aid in enhancing the stability, solubility, absorption, bioavailability, pharmacokinetics and cellular uptake of said compound, in particular formulations comprising excipients capable of forming complexes, nanoparticles, microparticles, nanotubes, nanogels, hydrogels, poloxamers or pluronics, polymersomes, colloids, microbubbles, vesicles, micelles, lipoplexes, and/or liposomes. Examples of nanoparticles include polymeric nanoparticles, gold nanoparticles, magnetic nanoparticles, silica nanoparticles, lipid nanoparticles, sugar particles, protein nanoparticles and peptide nanoparticles.

A preferred composition comprises at least one excipient that may further aid in enhancing the targeting and/or delivery of said composition and/or said oligonucleotide to and/or into muscle and/or brain tissue and/or to a neuronal tissue and/or a cell. A cell may be a muscular or a neuronal cell.

Many of these excipients are known in the art (e.g. see Bruno, 2011) and may be categorized as a first type of excipient. Examples of first type of excipients include polymers (e.g. polyethyleneimine (PEI), polypropyleneimine (PPI), dextran derivatives, butylcyanoacrylate (PBCA), hexylcyanoacrylate (PHCA), poly(lactic-co-glycolic acid) (PLGA), polyamines (e.g. spermine, spermidine, putrescine, cadaverine), chitosan, poly(amido amines) (PAMAM), poly (ester amine), polyvinyl ether, polyvinyl pyrrolidone (PVP), polyethylene glycol (PEG) cyclodextrins, hyaluronic acid, colominic acid, and derivatives thereof), dendrimers (e.g. poly(amidoamine)), lipids {e.g. 1,2-dioleoyl-3-dimethylammonium propane (DODAP), dioleoyldimethylammonium chloride (DODAC), phosphatidylcholine derivatives [e.g 1,2-distearoyl-sn-glycero-3-phosphocholine (DSPC)], lyso-phosphatidylcholine derivaties [e.g. 1-stearoyl-2-lyso-sn-glycero-3-phosphocholine (S-LysoPC)], sphingomyeline, 2-{3-[bis-(3-amino-propyl)-amino]-propylamino}-N-ditet-racedyl carbamoyl methylacetamide (RPR209120), phosphoglycerol derivatives [e.g. 1,2-dipalmitoyl-sn-glycero-3-phosphoglycerol sodium salt (DPPG-Na), phosphaticid acid derivatives [1,2-distearoyl-sn-glycero-3-phosphaticid acid, sodium salt (DSPA), phosphatidylethanolamine derivatives [e.g. dioleoyl-phosphatidylethanolamine (DOPE), 1,2-distearoyl-sn-glycero-3-phosphoethanolamine (DSPE),2-diphytanoyl-sn-glycero-3-phosphoethanolamine (DP-hyPE),], N-[1-(2,3-dioleoyloxy)propyl]-N,N,N-trimethylammonium (DOTAP), N-[1-(2,3-dioleyloxy) propyl]-N,N,N-trimethylammonium (DOTMA), 1,3-dioleoyloxy-2-(6-carboxy-spermyl)-propylamid (DOSPER), (1,2-dimyristyolxypropyl-3-dimethylhydroxy ethyl ammonium (DMRIE), (N1-cholesteryloxycarbonyl-3,7-diazanonane-1,9-diamine (CDAN), dimethyldioctadecylammonium bromide (DDAB), 1-palmitoyl-2-oleoyl-sn-glycerol-3-phosphocholine (POPC), (b-L-arginyl-2,3-L-diaminopropionic acid-N-palmityl-N-olelyl-amide trihydrochloride (AtuFECT01), N,N-dimethyl-3-aminopropane derivatives [e.g. 1,2-distearoyloxy-N,N-dimethyl-3-aminopropane (DSDMA), 1,2-dioleyloxy-N,N-dimethyl-3-aminopropane (DoDMA), 1,2-dilinoleyloxy-N,N-3-dimethylaminopropane (DLinDMA), 2,2-dilinoleyl-4-dimethylaminomethyl [1,3]-dioxolane (DLin-K-DMA), phosphatidylserine derivatives [1,2-dioleyl-sn-glycero-3-phospho-L-serine, sodium salt (DOPS)], cholesterol}proteins (e.g. albumin, gelatins, atellocollagen), and peptides (e.g. protamine, PepFects, NickFects, polyarginine, polylysine, CADY, MPG).

Another preferred composition may comprise at least one excipient categorized as a second type of excipient. A second type of excipient may comprise or contain a conjugate group as described herein to enhance targeting and/or delivery of the composition and/or of the oligonucleotide of the invention to a tissue and/or cell and/or into a tissue and/or cell, as for example muscle or neuronal tissue or cell. Both types of excipients may be combined together into one single composition as identified herein.

The skilled person may select, combine and/or adapt one or more of the above or other alternative excipients and delivery systems to formulate and deliver a compound for use in the present invention.

Such a pharmaceutical composition of the invention may be administered in an effective concentration at set times to an animal, preferably a mammal. More preferred mammal is a human being. An oligonucleotide or a composition as defined herein for use according to the invention may be suitable for direct administration to a cell, tissue and/or an organ in vivo of individuals affected by or at risk of developing a disease or condition as identified herein, and may be administered directly in vivo, ex vivo or in vitro. Administration may be via systemic and/or parenteral routes, for example intravenous, subcutaneous, intraventricular, intrathecal, intramuscular, intranasal, enteral, intravitreal, intracerebral, epidural or oral route.

Preferably, such a pharmaceutical composition of the invention may be encapsulated in the form of an emulsion, suspension, pill, tablet, capsule or soft-gel for oral delivery, or in the form of aerosol or dry powder for delivery to the respiratory tract and lungs. In an embodiment an oligonucleotide of the invention may be used together with another compound already known to be used for the treatment of said disease. Such other compounds may be used for slowing down progression of disease, for reducing abnormal behaviors or movements, for reducing muscle tissue inflammation, for improving muscle fiber and/or neuronal function, integrity and/or survival and/or improve, increase or restore cardiac function. Examples are, but not limited to, a steroid, preferably a (gluco)corticosteroid, an ACE inhibitor (preferably perindopril), an angiotensin II type 1 receptor blocker (preferably losartan), a tumor necrosis factor-alpha (TNFα) inhibitor, a TGFβ inhibitor (preferably decorin), human recombinant biglycan, a source of mIGF-1, a myostatin inhibitor, mannose-6-phosphate, dantrolene, halofuginone, an antioxidant, an ion channel inhibitor, a protease inhibitor, a phosphodiesterase inhibitor (preferably a PDE5 inhibitor, such as sildenafil or tadalafil, and/or PDE10A inhibitors and/or MP-10), L-arginine, dopamine blockers, amantadine, tetrabenazine, co-enzyme Q10, antidepressants, anti-psychotics, anti-epileptics, mood-stabilizers in general, omega-3-fatty acids, creatine monohydrate, KMO inhibitors (Kynurenine mono oxigenase) such as CHDI246, or HDAC4 inhibitors such as PBT2. Such combined use may be a sequential use: each component is administered in a distinct composition. Alternatively each compound may be used together in a single composition.

Use

In a further aspect, there is provided the use of a composition or an oligonucleotide as described in the previous sections for use as a medicament or part of therapy, or applications in which said oligonucleotide exerts its activity intracellularly. Preferably, an oligonucleotide or composition of the invention is for use as a medicament or part of a therapy for preventing, delaying, curing, ameliorating and/or treating a human cis-element repeat instability associated genetic disorder. A human cis-element repeat instability associated genetic disorder is preferably a neuromuscular genetic disorder, more preferably as identified earlier herein.

Method

In a further aspect, there is provided a method for preventing, treating, curing, ameliorating and/or delaying a condition or disease as defined in the previous section in an individual, in a cell, tissue or organ of said individual. The method comprising administering an oligonucleotide or a composition of the invention to said individual or a subject in the need thereof.

The method according to the invention wherein an oligonucleotide or a composition as defined herein may be suitable for administration to a cell, tissue and/or an organ in vivo of individuals affected by any of the herein defined diseases or at risk of developing said disease, and may be administered in vivo, ex vivo or in vitro. An individual or a subject in need is preferably a mammal, more preferably a human being.

In a further aspect, there is provided a method for diagnosis wherein the oligonucleotide of the invention is provided with a radioactive label or fluorescent label. In this method, an oligonucleotide of the invention may be used as an in situ probe to detect foci (RNA/protein aggregates resulting from the repeat expansion) in a sample from a subject. Said sample comprises cells from said subject.

In an embodiment, in a method of the invention, a concentration of an oligonucleotide or composition is ranged from 0.01 nM to 1 µM. More preferably, the concentration used is from 0.05 to 500 nM, or from 0.1 to 500 nM, or from 0.02 to 500 nM, or from 0.05 to 500 nM, even more preferably from 1 to 200 nM.

Dose ranges of an oligonucleotide or composition according to the invention are preferably designed on the basis of rising dose studies in clinical trials (in vivo use) for which rigorous protocol requirements exist. An oligonucleotide as defined herein may be used at a dose which is ranged from 0.01 to 200 mg/kg or 0.05 to 100 mg/kg or 0.1 to 50 mg/kg or 0.1 to 20 mg/kg, preferably from 0.5 to 10 mg/kg.

Dose ranges of an oligonucleotide or composition according to the invention may also be used at a dose which is Ranged from 100 to 300 µg/week, 8 to 12 injections in total or Ranged from 150 to 250 µg/week, 9 to 11 injections in total or 200 µg/week, 11 injections in total or Ranged from 10 to 350 µg/day during two weeks or Ranged from 50 to 250 µg/day during two weeks or Ranged from 100 to 200 µg/day during two weeks or Ranged from 20 to 80 µg/day during two weeks or Ranged from 200 to 320 µg/day during two weeks or 320 µg/day, during two weeks or 30 µg/day, during two weeks.

The ranges of concentration or dose of oligonucleotide or composition as given above are preferred concentrations or doses for in vitro or ex vivo uses. The skilled person will understand that depending on the identity of the oligonucleotide used, the target cell to be treated, the gene target and its expression levels, the medium used and the transfection and incubation conditions, the concentration or dose of oligonucleotide used may further vary and may need to be optimised any further.

In this document and in its claims, the verb "to comprise" and its conjugations is used in its non-limiting sense to mean that items following the word are included, but items not specifically mentioned are not excluded. The verb "to comprise" is synonymous with the verb "to have" unless otherwise indicated. In addition the verb "to consist" may be replaced by "to consist essentially of" meaning that an oligonucleotide or a composition as defined herein may comprise additional component(s) than the ones specifically identified, said additional component(s) not altering the unique characteristic of the invention. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each embodiment as identified herein may be combined together unless otherwise indicated. All patent and literature references cited in the present specification are hereby incorporated by reference in their entirety.

Definitions

Throughout the application, the word "binds", "targets", "hybridizes" could be used interchangeably when used in the context of an antisense oligonucleotide which is reverse complementary to a part of a pre-mRNA as identified herein. In the context of the invention, "hybridizes" or "binds" is used under physiological conditions in a cell, preferably a human cell unless otherwise indicated.

As used herein, "hybridization" refers to the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymine, 5-methyluracil and uracil which pair through the formation of hydrogen bonds. The natural base guanine is nucleobase complementary to the natural bases cytosine and 5-methyl-cytosine. Hybridization can occur under varying circumstances. In particular, hybridization of an oligonucleotide of the invention with a targeted pre-mRNA can occur under varying circumstances. Similarly, binding of an oligonucleotide of the invention to a targeted pre-mRNA can occur under varying circumstances. Preferably, said hybridization or said binding is assessed under physiological conditions in a cell, more preferably in a human cell. An oligonucleotide of the invention is preferably said to be able to bind to, or capable of binding to, or able to hybridize with, or capable of hybridizing with, when said binding or hybridization occurs under physiological conditions in a cell, preferably a human cell.

As used herein, "nucleotide" refers to a nucleoside further comprising a modified or unmodified phosphate linking group or a non-phosphate internucleoside linkage.

As used herein, "nucleotide analogue" or "nucleotide equivalent" refers to a nucleotide, which comprises at least one modification with respect to the nucleotides naturally occurring in RNA, such as A, C, G and U. Such a modification may be an internucleoside linkage modification and/or a sugar modification and/or a base modification.

As used herein, "monomer" refers to a precursor in the synthesis of an oligomeric or polymeric compound. Also the monomeric unit or residue within such an oligomeric or polymeric compound is encompassed in the term "monomer". Thus, "monomer" and "nucleotide residue" may be used interchangeably throughout the description. Within the context of the present invention, a monomer is preferably a nucleotide. Preferred monomers to be incorporated in the oligonucleotides according to the invention are nucleotides comprising a 2'-O-methyl substituent, a phosphorothioate internucleoside linkage and a 5-methylpyrimidine and/or a 2,6-diaminopurine nucleobase.

As used herein, "nucleobase" refers to the heterocyclic base portion of a nucleoside. Nucleobases may be naturally occurring or may be modified and therefore include, but are not limited to adenine, cytosine, guanine, uracil, thymine and analogues thereof such as 5-methyl-cytosine. In certain embodiments, a nucleobase may comprise any atom or group of atoms capable of hydrogen bonding to a base of another nucleic acid. As used herein, "$T_m$" means melting temperature which is the temperature at which the two strands of a duplex nucleic acid separate. $T_m$ is often used as a measure of duplex stability or the binding affinity of an antisense compound toward a complementary RNA molecule.

As used herein, "2'-modified" or "2'-substituted" refers to a nucleoside comprising a pentose sugar comprising a substituent at the 2' position other than H or OH. 2'-modified nucleosides include, but are not limited to, bicyclic nucleosides wherein the bridge connecting two carbon atoms of the sugar ring connects the 2' carbon and another carbon of the sugar ring; and nucleosides with non-bridging 2'-substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—N$(R_m)(R_n)$, or O—$CH_2$—C(=O)—N$(R_m)(R_n)$, wherein each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-O-Me", "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, the term "adenine analogue" means a chemically-modified purine nucleobase that, when incorporated into an oligomer, is capable of forming a base pair with either a thymine or uracil of a complementary strand of RNA or DNA. Preferably, such base pair is a Watson-Crick base pair, but analogues and slight deviations thereof are also considered allowable within the context of the present invention.

As used herein, the term "uracil analogue" means a chemically-modified pyrimidine nucleobase that, when incorporated into an oligomer, is capable of forming a base pair with either a adenine of a complementary strand of RNA or DNA. Preferably, such base pair is a Watson-Crick base pair, but analogues and slight deviations thereof are also considered allowable within the context of the present invention.

As used herein, the term "thymine analogue" means a chemically-modified pyrimidine nucleobase that, when incorporated into an oligomer, is capable of forming a base pair with an adenine of a complementary strand of RNA or DNA. Preferably, such base pair is a Watson-Crick base pair, but analogues and slight deviations thereof are also considered allowable within the context of the present invention.

As used herein, the term "cytosine analogue" means a chemically-modified pyrimidine nucleobase that, when incorporated into an oligomer, is capable of forming a base pair with a guanine of a complementary strand of RNA or DNA. For example, cytosine analogue can be a 5-methyl-cytosine. Preferably, such base pair is a Watson-Crick base pair, but analogues and slight deviations thereof are also considered allowable within the context of the present invention.

As used herein, the term "guanine analogue" means a chemically-modified purine nucleobase that, when incorporated into an oligomer, is capable of forming a base pair with a cytosine of a complementary strand of RNA or DNA. Preferably, such base pair is a Watson-Crick base pair, but analogues and slight deviations thereof are also considered allowable within the context of the present invention.

As used herein, the term "guanosine" refers to a nucleoside or sugar-modified nucleoside comprising a guanine or guanine analog nucleobase.

As used herein, the term "uridine" refers to a nucleoside or sugar-modified nucleoside comprising a uracil or uracil analog nucleobase.

As used herein, the term "thymidine" refers to a nucleoside or sugar-modified nucleoside comprising a thymine or thymine analog nucleobase.

As used herein, the term "cytidine" refers to a nucleoside or sugar-modified nucleoside comprising a cytosine or cytosine analog nucleobase.

As used herein, the term "adenosine" refers to a nucleoside or sugar-modified nucleoside comprising an adenine or adenine analog nucleobase.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

As used herein, "internucleoside linkage" refers to a covalent linkage between adjacent nucleosides. An internucleoside linkage may be a naturally occurring internucleoside linkage, i.e. a 3' to 5' phosphodiester linkage, or a modified internucleoside linkage.

As used herein, "modified internucleoside linkage" refers to any internucleoside linkage other than a naturally occurring internucleoside linkage.

As used herein, "backbone" refers to the chain of alternating sugar moieties and internucleoside linkages, as it occurs in an oligonucleotide. The oligonucleotide of the invention comprises at least one phosphorodithioate internucleoside linkage, but it has to be understood that more backbone modifications, such as sugar modifications and/or internucleoside linkage modifications may be present in the backbone.

As used herein, "oligomeric compound" refers to a polymeric structure comprising two or more sub-structures. In certain embodiments, an oligomeric compound is an oligonucleotide. In certain embodiments, an oligomeric compound is a single-stranded oligonucleotide. In certain embodiments, an oligomeric compound is a double-stranded duplex comprising two oligonucleotides. In certain embodiments, an oligomeric compound is a single-stranded or double-stranded oligonucleotide comprising one or more conjugate groups and/or terminal groups.

As used herein, "conjugate" refers to an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and clearance. Conjugate groups are routinely used in the chemical arts and are linked directly or via an optional linking moiety or linking group to the parent compound such as an oligomeric compound. In certain embodiments, conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. In certain embodiments, conjugates are terminal groups. In certain embodiments, conjugates are attached to a 3' or 5' terminal nucleoside or to an internal nucleoside of an oligonucleotide.

As used herein, "conjugate linking group" refers to any atom or group of atoms used to attach a conjugate to an oligonucleotide or oligomeric compound. Linking groups or bifunctional linking moieties such as those known in the art are amenable to the present invention.

As used herein, "antisense compound" refers to an oligomeric compound, at least a portion of which is at least partially complementary to, or at least partially directed to, a target nucleic acid to which it hybridizes and modulates the activity, processing or expression of said target nucleic acid.

As used herein, "expression" refers to the process by which a gene ultimately results in a protein. Expression includes, but is not limited to, transcription, splicing, post-transcriptional modification, and translation.

As used herein, "antisense oligonucleotide" refers to an antisense compound that is an oligonucleotide.

As used herein, "antisense activity" refers to any detectable and/or measurable activity attributable to the hybridization of an anti sense compound to its target nucleic acid. In certain embodiments, such activity may be an increase or decrease in an amount of a nucleic acid or protein. In certain embodiments, such activity may be a change in the ratio of splice variants of a nucleic acid or protein. Detection and/or measuring of antisense activity may be direct or indirect. In certain embodiments, antisense activity is assessed by observing a phenotypic change in a cell or animal.

As used herein, "target nucleic acid" refers to any nucleic acid molecule the expression, amount, or activity of which is capable of being modulated by an antisense compound.

In certain embodiments, the target nucleic acid is DNA or RNA. In certain embodiments, the target RNA is miRNA, mRNA, pre-mRNA, non-coding RNA, or natural antisense transcripts. For example, the target nucleic acid can be a cellular gene (or mRNA transcribed from the gene) whose expression is associated with a particular disorder or disease state, As used herein, "target mRNA" refers to a pre-selected RNA molecule that encodes a protein.

As used herein, "targeting" or "targeted to" refers to the association of an antisense compound to a particular target nucleic acid molecule or a particular region of nucleotides within a target nucleic acid molecule. An antisense compound targets a target nucleic acid if it is sufficiently reverse complementary to the target nucleic acid to allow hybridization under physiological conditions. In this context "sufficiently reverse complementary" may be at least 90%, 95%, 97%, 99% or 100% reverse complementary with said targeted nucleic acid molecule.

As used herein, "target site" refers to a region of a target nucleic acid that is bound by an antisense compound. In certain embodiments, a target site is at least partially within the 3' untranslated region of an RNA molecule. In certain embodiments, a target site is at least partially within the 5' untranslated region of an RNA molecule. In certain embodiments, a target site is at least partially within the coding region of an RNA molecule. In certain embodiments, a target site is at least partially within an exon of an RNA molecule. In certain embodiments, a target site is at least partially within an intron of an RNA molecule. In certain embodiments, a target site is at least partially within a miRNA target site of an RNA molecule. In certain embodiments, a target site is at least partially within a repeat region of an RNA molecule.

As used herein, "target protein" refers to a protein, the expression of which is modulated by an antisense compound. In certain embodiments, a target protein is encoded by a target nucleic acid. In certain embodiments, expression of a target protein is otherwise influenced by a target nucleic acid.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases refers to a pair of nucleobases that do not form hydrogen bonds with one another or otherwise support hybridization.

As used herein, "complementary" in reference to linked nucleosides, oligonucleotides, or nucleic acids, refers to the capacity of an oligomeric compound to hybridize to another oligomeric compound or nucleic acid through nucleobase complementarity. In certain embodiments, an antisense compound and its target are complementary to each other when a sufficient number of corresponding positions in each molecule are occupied by nucleobases that can bond with each other to allow stable association between the antisense compound and the target. One skilled in the art recognizes that the inclusion of mismatches is possible without eliminating the ability of the oligomeric compounds to remain in association. Therefore, described herein are antisense compounds that may comprise up to about 20% nucleotides that are mismatched (i.e., are not nucleobase complementary to the corresponding nucleotides of the target).

Preferably the antisense compounds contain no more than about 15%, more preferably not more than about 10%, most preferably not more than 5% or no mismatches. The remaining nucleotides are nucleobase complementary or otherwise do not disrupt hybridization (e.g., universal bases). One of ordinary skill in the art would recognize the compounds provided herein are at least 80%, at least 85%, at least 90%, at least 95%, at least 96%, at least 97%, at least 98%, at least 99% or 100% complementary to a target nucleic acid or reverse complementarity to a target nucleic acid.

As used herein, "modulation" refers to a perturbation of amount or quality of a function or activity when compared to the function or activity prior to modulation. For example, modulation includes the change, either an increase (stimulation or induction) or a decrease (inhibition or reduction) in gene expression. As a further example, modulation of expression can include perturbing splice site selection of pre-mRNA processing, resulting in a change in the amount of a particular splice-variant present compared to conditions that were not perturbed. As a further example, modulation includes perturbing translation of a protein.

As used herein, "motif" refers to a pattern of modifications in an oligomeric compound or a region thereof. Motifs may be defined by modifications at certain nucleosides and/or at certain linking groups of an oligomeric compound.

As used herein, "the same modifications" refer to modifications relative to naturally occurring molecules that are the same as one another, including absence of modifications. Thus, for example, two unmodified DNA nucleoside have "the same modification," even though the DNA nucleoside is unmodified.

As used herein, "type of modification" in reference to a nucleoside or a nucleoside of a "type" refers to the modification of a nucleoside and includes modified and unmodified nucleosides. Accordingly, unless otherwise indicated, a "nucleoside having a modification of a first type" may be an unmodified nucleoside.

As used herein, "pharmaceutically acceptable salts" refers to salts of active compounds that retain the desired biological activity of the active compound and do not impart undesired toxicological effects thereto.

As used herein, the term "independently" means that each occurrence of a repetitive variable within a claimed oligonucleotide is selected independent of one another. For example, each repetitive variable can be selected so that (i) each of the repetitive variables are the same, (ii) two or more are the same, or (iii) each of the repetitive variables can be different.

General Chemistry Definitions

As used herein, "alkyl" refers to a saturated straight or branched hydrocarbon substituent or radical, typically containing up to twenty four carbon atoms. Examples of alkyl groups include, but are not limited to, methyl, ethyl, propyl, butyl, isopropyl, n-hexyl, octyl, decyl, dodecyl and the like. Alkyl groups typically include from 1 to 24 carbon atoms, more typically from 1 to 12 carbon atoms ($C_1$-$C_{12}$ alkyl) with from 1 to 6 carbon atoms ($C_1$-$C_6$ alkyl) being more preferred. The term "lower alkyl" as used herein includes from 1 to 6 carbon atoms ($C_1$-$C_6$ alkyl). Alkyl groups as used herein may optionally contain one or more further substituents.

As used herein, "alkenyl" refers to a straight or branched hydrocarbon chain radical or substituent, typically containing up to twenty four carbon atoms, and having at least one carbon-carbon double bond. Examples of alkenyl groups include, but are not limited to, ethenyl, propenyl, butenyl, 1-methyl-2-buten-1-yl, dienes such as 1,3-butadienyl and the like. Alkenyl groups typically include from 2 to 24 carbon atoms, more typically from 2 to 12 carbon atoms with from 2 to 6 carbon atoms being more preferred. Alkenyl groups as used herein may optionally contain one or more further substituents.

As used herein, "alkynyl" refers to a straight or branched hydrocarbon radical or substituent, typically containing up to twenty four carbon atoms, and having at least one carbon-carbon triple bond. Examples of alkynyl groups include, but are not limited to, ethynyl, 1-propynyl, 1-butynyl, and the like. Alkynyl groups typically include from 2 to 24 carbon atoms, more typically from 2 to 12 carbon atoms with from 2 to 6 carbon atoms being more preferred. Alkynyl groups as used herein may optionally contain one or more further substituents.

As used herein, "aminoalkyl" refers to an amino substituted alkyl radical or substituent. This term is meant to include $C_1$-$C_{12}$ alkyl groups having an amino substituent at any position and wherein the aminoalkyl group is attached to the parent molecule via its alkyl moiety. The alkyl and/or amino portions of the aminoalkyl group may optionally be further substituted with further substituents.

As used herein, "aliphatic" refers to a straight or branched hydrocarbon radical or substituent, typically containing up to twenty four carbon atoms, wherein the saturation between any two carbon atoms is a single, double or triple bond. An aliphatic group preferably contains from 1 to 24 carbon atoms, more typically from 1 to 12 carbon atoms with from 1 to 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation polyalkoxys, such as polyalkylene glycols, polyamines, and polyimines. Aliphatic groups as used herein may optionally contain further substituents.

As used herein, "alicyclic" or "alicyclyl" refers to a cyclic radical or substituent, wherein the ring system is aliphatic. The ring system can comprise one or more rings wherein at least one ring is aliphatic. Preferred alicyclic moieties include rings having from 5 to 9 carbon atoms in the ring. Alicyclic groups as used herein may optionally contain further substituents.

As used herein, "alkoxy" refers to a radical or substituent comprising an alkyl group and an oxygen atom, wherein the alkoxy group is attached to a parent molecule via its oxygen atom. Examples of alkoxy groups include, but are not limited to, methoxy, ethoxy, propoxy, isopropoxy, n-butoxy, sec-butoxy, tert-butoxy, n-pentoxy, neopentoxy, n-hexoxy and the like. Alkoxy groups as used herein may optionally contain further substituents.

As used herein, "halo", "halide" and "halogen" refer to an atom, radical or substituent selected from fluorine, chlorine, bromine and iodine.

As used herein, "aryl" and "aromatic" refer to a radical or substituent comprising a mono- or polycyclic carbocyclic ring system having one or more aromatic rings. Examples of aryl groups include, but are not limited to, phenyl, naphthyl, tetrahydronaphthyl, indanyl, idenyl and the like. Preferred aryl ring systems have from 5 to 20 carbon atoms in one or more rings. Aryl groups as used herein may optionally contain further substituents.

As used herein, "aralkyl" and "arylalkyl" refer to a radical or substituent comprising an alkyl group and an aryl group, wherein the aralkyl or arylalkyl group is attached to a parent molecule via its alkyl moiety. Examples include, but are not limited to, benzyl, phenethyl and the like. Aralkyl groups as used herein may optionally contain further substituents attached to the alkyl, the aryl or both moieties that form the radical or substituent.

As used herein, "heterocyclyl" refers to a radical or substituent comprising a mono- or polycyclic ring system that includes at least one heteroatom and is unsaturated, partially saturated or fully saturated, thereby including heteroaryl groups. Heterocyclyl is also meant to include fused ring system moieties wherein one or more of the fused rings contain at least one heteroatom and the other rings can contain one or more heteroatoms or optionally contain no heteroatoms. A heterocyclic group typically includes at least one atom selected from sulfur, nitrogen or oxygen. Examples of heterocyclic groups include [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally contain further substituents. As used herein, "heteroaryl" and "heteroaromatic" refer to a radical or substituent comprising a mono- or polycyclic aromatic ring, ring system or fused ring system wherein at least one of the rings is aromatic and includes one or more heteroatom. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include, but are not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. Heteroaryl radicals or substituents can be attached to a parent molecule directly or through a linking moiety such as an aliphatic group or a heteroatom. Heteroaryl groups as used herein may optionally contain further substituents.

As used herein, "heteroarylalkyl" refers to a radical or substituent comprising a heteroaryl group as previously defined and an alkyl moiety, wherein the heteroarylalkyl group is attached to a parent molecule via its alkyl moiety. Examples include, but are not limited to, pyridinylmethyl, pyrimidinylethyl, napthyridinylpropyl and the like. Heteroarylalkyl groups as used herein may optionally contain further substituents on one or both of the heteroaryl or alkyl portions.

As used herein, "mono or polycyclic" refers to any ring systems, such as a single ring or a polycyclic system having rings that are fused or linked, and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and polycyclic structures can contain rings that have a uniform or varying degree of saturation, including fully saturated, partially saturated or fully unsaturated rings. Each ring can comprise ring atoms selected from C, N, O and S to give rise to heterocyclic rings as well as rings comprising only C ring atoms.

Heterocyclic and all-carbon rings can be present in a mixed motif, such as for example benzimidazole wherein one ring of the fused ring system has only carbon ring atoms and the other ring has two nitrogen atoms. The mono or polycyclic structures can be further substituted with substituents such as for example phthalimide which has two oxo groups (=O) attached to one of the rings. In another aspect, mono or polycyclic structures can be attached to a parent molecule directly through a ring atom, through a substituent or a bifunctional linking moiety.

As used herein, "acyl" refers to a radical or substituent comprising a carbonyl moiety (C=O or —C(O)—) and a further substituent X, wherein the acyl group is attached to a parent molecule via its carbonyl moiety. As such, an acyl group is formally obtained by removal of a hydroxyl group from an organic acid and has the general formula —C(O)—X, wherein X is typically aliphatic, alicyclic or aromatic. The term "acyl" is also meant to include heteroacyl radicals or substituents with general formula —Y(O)$_n$—X, wherein X is as defined above and Y(O)$_n$ is typically sulfonyl, sulfinyl or phosphate. Examples of acyl groups include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally contain further substituents.

As used herein, "substituent" and "substituent group" include groups that are typically added to other substituents or parent compounds to enhance desired properties or give desired effects. Substituent groups can be protected or unprotected and can be attached to one available site or to many available sites in a parent compound. Substituent groups may also be further substituted with other substituent groups and may be attached directly or via a linking group such as an alkyl or hydrocarbyl group to a parent compound. Herein, "hydrocarbyl" refers to any group comprising C, O and H. Included are straight, branched and cyclic groups having any degree of saturation. Such hydrocarbyl groups can include one or more heteroatoms selected from N, O and S and can be further substituted with one or more substituents.

Unless otherwise indicated, the term "substituted" or "optionally substituted" refers to the (optional) presence of any of the following substituents: halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxo (—O—R$_{aa}$), aryl, aralkyl, heterocyclic, heteroaryl, heteroarylalkyl, amino (—NR$_{bb}$R$_{cc}$), imino (=NR$_{bb}$), amido (—C(O)NR$_{bb}$R$_{cc}$ or —N(R$_{bb}$)C(O)R$_{aa}$), azido (—N$_3$), nitro (—NO$_2$), cyano (—CN), carbamido (—OC(O)NR$_{bb}$R$_{cc}$ or —N(R$_{bb}$)C(O)OR$_{aa}$), ureido (—N(R$_{bb}$)C(O)NR$_{bb}$R$_{cc}$), thioureido (—N(R$_{bb}$)C(S)NR$_{bb}$R$_{cc}$), guanidinyl (—N(R$_{bb}$)C(=NR$_{bb}$)NR$_{bb}$R$_{cc}$), amidinyl (—C(=NR$_{bb}$)NR$_{bb}$R$_{cc}$ or —N(R$_{bb}$)C(NR$_{bb}$)R$_{aa}$), thiol (—SR$_{bb}$), sulfinyl (—S(O)R$_{bb}$), sulfonyl (—S(O)$_2$R$_{bb}$), sulfonamidyl (—S(O)$_2$NR$_{bb}$R$_{cc}$ or —N(R$_{bb}$)S(O)$_2$R$_{bb}$) and conjugate groups. Herein, each R$_{aa}$, R$_{bb}$ and R$_{cc}$ is, independently, H, an optionally linked chemical functional group or a further substituent, preferably but without limitation chosen from the group consisting of H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

As used herein, a zero (0) in a range indicating number of a particular unit means that the unit may be absent. For example, an oligomeric compound comprising 0-2 regions of a particular motif means that the oligomeric compound may comprise one or two such regions having the particular motif, or the oligomeric compound may not have any regions having the particular motif. In instances where an internal portion of a molecule is absent, the portions flanking the absent portion are bound directly to one another. Likewise, the term "none" as used herein, indicates that a certain feature is not present. As used herein, "analogue" or "derivative" means either a compound or moiety similar in structure but different in respect to elemental composition from the parent compound regardless of how the compound is made. For example, an analogue or derivative compound does not need to be made from the parent compound as a chemical starting material.

The following examples are offered for illustrative purposes only, and are not intended to limit the scope of the present invention in any way.

BRIEF DESCRIPTION OF THE FIGURES

FIGS. 2A-2D. In vivo efficacy of PS659 ((XYG)$_7$ in which X=5-methylcytosine and Y=U; SEQ ID NO:2) in a transgenic HD rat model. Transgenic HD rats ((CAG)$_{51}$ repeat) received 15 times an intraventricular injection with PS659 (SEQ ID NO:90 derived from SEQ ID NO: 2), during 18 weeks at a final dose of 200 μg per injection, control HD rats received vehicle only. Rats were sacrificed one week after the final injection. From all rats tissue was isolated and HTT levels were determined with Q-RT-PCR analysis. Reduced levels of HTT transcript were found in (FIG. 2A)

Figure 1A:
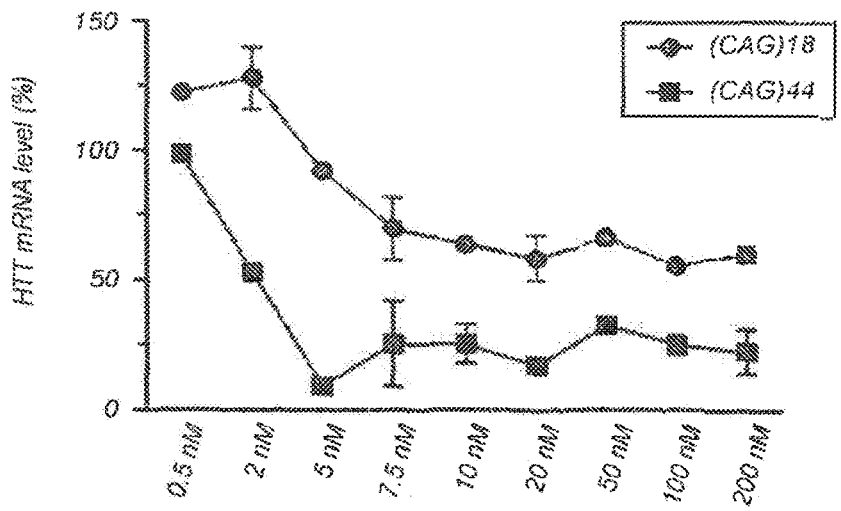
FIGS. 1A-1B. In vitro activity assay for (XYG)$_7$ in which X=5-methylcytosine and Y=U (PS659 SEQ ID NO:90; derived from SEQ ID NO:2) and (XYG)$_7$ in which X=C and Y is 5-methyluracil (PS661 SEQ ID NO: 97; derived from SEQ ID NO:3). PS659 (FIG. 1A) and PS661 (FIG. 1B) were transfected into HD fibroblasts (GM04022) at increasing concentrations (0.5-200 nM). Efficacy and selectivity was determined with RT-PCR and lab-on-a-chip analysis. Silencing of the expanded ((CAG)$_{44}$) and healthy ((CAG)$_{18}$) HTT transcripts were compared to the relative HTT transcript levels in mock samples. For all AONs n=2 except for mock (n=3).

cortex, (FIG. 2B) hippocampus, (FIG. 2C) olfactory bulb and (FIG. 2D) thalamus after PS659 treatment compared to control.

TABLE 1

General structures of AONs. X = C or 5-methylcytosine Y = U or 5-methyluracil, Z = A or 2,6-diaminopurine, I = inosine, and Q = abasic monomer.

| Target Repeat | AON Sequence (5' → 3') | SEQ ID NO |
|---|---|---|
| (CAG)n | (XYG)7 (PS57)<br>X = C, Y = U | 1 |
| | (XYG)7 (PS659)<br>X = 5-methylcytosine, Y = U | 2 |
| | (XYG)7 (PS661)<br>X = C, Y = 5-methyluracil | 3 |
| | (XYG)4 | 4 |
| | (XYG)5 | 5 |
| | (XYG)6 | 6 |
| | (XYG)7 | 7 |
| | (XYG)8 | 8 |
| | (XYG)9 | 9 |
| | (XYG)10 | 10 |
| | (XYG)11 | 11 |
| | (XYG)12 | 12 |
| (GCG)n | (XGX)4 | 13 |
| | (XGX)5 | 14 |
| | (XGX)6 | 15 |
| | (XGX)7 | 16 |
| | (XGX)8 | 17 |
| | (XGX)9 | 18 |
| | (XGX)10 | 19 |
| | (XGX)11 | 20 |
| | (XGX)12 | 21 |
| (CGG)n | (XXG)4 | 22 |
| | (XXG)5 | 23 |
| | (XXG)6 | 24 |
| | (XXG)7 | 25 |
| | (XXG)8 | 26 |
| | (XXG)9 | 27 |
| | (XXG)10 | 28 |
| | (XXG)11 | 29 |
| | (XXG)12 | 30 |
| (GAA)n | (YYX)4 | 31 |
| | (YYX)5 | 32 |
| | (YYX)6 | 33 |
| | (YYX)7 | 34 |

TABLE 1-continued

General structures of AONs. X = C or 5-methylcytosine Y = U or 5-methyluracil, Z = A or 2,6-diaminopurine, I = inosine, and Q = abasic monomer.

| Target Repeat | AON Sequence (5' → 3') | SEQ ID NO |
|---|---|---|
| | (YYX)8 | 35 |
| | (YYX)9 | 36 |
| | (YYX)10 | 37 |
| | (YYX)11 | 38 |
| | (YYX)12 | 39 |
| (GCC)n | (GGX)4 | 40 |
| | (GGX)5 | 41 |
| | (GGX)6 | 42 |
| | (GGX)7 | 43 |
| | (GGX)8 | 44 |
| | (GGX)9 | 45 |
| | (GGX)10 | 46 |
| | (GGX)11 | 47 |
| | (GGX)12 | 48 |
| (CCG)n | (XGG)4 | 49 |
| | (XGG)5 | 50 |
| | (XGG)6 | 51 |
| | (XGG)7 | 52 |
| | (XGG)8 | 53 |
| | (XGG)9 | 54 |
| | (XGG)10 | 55 |
| | (XGG)11 | 56 |
| | (XGG)12 | 57 |
| (AUUCU)n | (ZGZZY)3 | 58 |
| | (ZGZZY)4 | 59 |
| | (ZGZZY)5 | 60 |
| | (ZGZZY)6 | 61 |
| | (ZGZZY)7 | 62 |
| (CCUG)n | (XZGG)3 | 63 |
| | (XZGG)4 | 64 |
| | (XZGG)5 | 65 |
| | (XZGG)6 | 66 |
| | (XZGG)7 | 67 |
| | (XZGG)8 | 68 |
| | (XZGG)9 | 69 |
| (GGGGCC)n | (GGXUXX)3 | 216 |
| | (GGXUXX)4 | 217 |
| | (GGXIXX)4 | 218 |
| | (GGXQXX)4 | 219 |

Note: All AONs with SEQ ID NO: 4-69, or 216-219 comprise at least one base modification selected from 5-methylcytosine, 5-methyluracil, and 2,6-diaminopurine.

TABLE 2

General structures of AONs. All AONs are 2'-O-methyl phosphorothioate AONs wherein C is 5-methylcytosine, U is 5-methyluracil, A is 2,6-diaminopurine, I is inosine and Q is an abasic monomer.

| Target Repeat | AON ID | AON Sequence (5'→3') | SEQ ID NO |
|---|---|---|---|
| (CAG)n | PS659 | CUG CUG CUG CUG CUG CUG CUG | 90 |
| | | CUG CUG CUG CUG CUG CUG CUG | 91 |
| | | CUG CUG CUG CUG CUG CUG CUG | 92 |
| | | CUG CUG CUG CUG CUG CUG CUG | 93 |
| | | CUG CUG CUG CUG CUG CUG CUG | 94 |
| | | CUG CUG CUG CUG CUG CUG CUG | 95 |
| | | CUG CUG CUG CUG CUG CUG CUG | 96 |
| | PS661 | CUG CUG CUG CUG CUG CUG CUG | 97 |
| | | CUG CUG CUG CUG CUG CUG CUG | 98 |
| | | CUG CUG CUG CUG CUG CUG CUG | 99 |
| | | CUG CUG CUG CUG CUG CUG CUG | 100 |
| | | CUG CUG CUG CUG CUG CUG CUG | 101 |
| | | CUG CUG CUG CUG CUG CUG CUG | 102 |
| | | CUG CUG CUG CUG CUG CUG CUG | 103 |
| | PS660 | CUG CUG CUG CUG CUG CUG CUG | 104 |
| | | CUG CUG CUG CUG CUG CUG CUG | 105 |
| | | CUG CUG CUG CUG CUG CUG CUG | 106 |
| | PS684 | CUG CUG CUG CUG CUG CUG CUG | 107 |
| | | CUG CUG CUG CUG CUG CUG CUG QQQQ | 220 |
| | | CUG CUG CUG CUG CUG CUG CUG | 108 |
| | | CUG CUG CUG CUG CUG CUG CUG QQQQ | 221 |
| | | CUG CUG CUG CUG CUG CUG CUG CUG | 109 |

TABLE 2-continued

General structures of AONs. All AONs are 2'-O-methyl phosphorothioate AONs wherein <u>C</u> is 5-methylcytosine, <u>U</u> is 5-methyluracil, <u>A</u> is 2,6-diaminopurine, I is inosine and Q is an abasic monomer.

| Target Repeat | AON ID | AON Sequence (5'→3') | SEQ ID NO |
|---|---|---|---|
| | | C<u>UG</u> C<u>UG</u> C<u>UG</u> C<u>UG</u> C<u>UG</u> C<u>UG</u> C<u>UG</u> C<u>UG</u> | 110 |
| | | <u>C</u>UG <u>C</u>UG <u>C</u>UG <u>C</u>UG <u>C</u>UG <u>C</u>UG <u>C</u>UG <u>C</u>UG | 111 |
| | | <u>CUG</u> <u>CUG</u> <u>CUG</u> <u>CUG</u> <u>CUG</u> <u>CUG</u> <u>CUG</u> <u>CUG</u> | 112 |
| | | <u>C</u>UG <u>C</u>UG <u>C</u>UG <u>C</u>UG <u>C</u>UG <u>C</u>UG <u>C</u>UG <u>C</u>UG <u>C</u>UG | 113 |
| | | C<u>UG</u> C<u>UG</u> C<u>UG</u> C<u>UG</u> C<u>UG</u> C<u>UG</u> C<u>UG</u> C<u>UG</u> C<u>UG</u> | 114 |
| | | <u>C</u>UG <u>C</u>UG <u>C</u>UG <u>C</u>UG <u>C</u>UG <u>C</u>UG <u>C</u>UG <u>C</u>UG <u>C</u>UG <u>C</u>UG | 115 |
| | | C<u>UG</u> C<u>UG</u> C<u>UG</u> C<u>UG</u> C<u>UG</u> C<u>UG</u> C<u>UG</u> C<u>UG</u> C<u>UG</u> C<u>UG</u> | 116 |
| | | <u>C</u>UG <u>C</u>UG <u>C</u>UG <u>C</u>UG <u>C</u>UG <u>C</u>UG <u>C</u>UG <u>C</u>UG <u>C</u>UG <u>C</u>UG <u>C</u>UG | 117 |
| | | CUG CUG CUG CUG CUG CUG CUG CUG CUG CUG CUG CUG | 118 |
| (GCG)n | | <u>C</u>GC <u>C</u>GC <u>C</u>GC <u>C</u>GC | 119 |
| | | <u>CGC</u> <u>CGC</u> <u>CGC</u> <u>CGC</u> | 120 |
| | | <u>C</u>GC <u>C</u>GC <u>C</u>GC <u>C</u>GC <u>C</u>GC | 121 |
| | | <u>CGC</u> <u>CGC</u> <u>CGC</u> <u>CGC</u> <u>CGC</u> | 122 |
| | | <u>C</u>GC <u>C</u>GC <u>C</u>GC <u>C</u>GC <u>C</u>GC <u>C</u>GC | 123 |
| | | <u>CGC</u> <u>CGC</u> <u>CGC</u> <u>CGC</u> <u>CGC</u> <u>CGC</u> | 124 |
| | | <u>C</u>GC <u>C</u>GC <u>C</u>GC <u>C</u>GC <u>C</u>GC <u>C</u>GC <u>C</u>GC | 125 |
| | | <u>CGC</u> <u>CGC</u> <u>CGC</u> <u>CGC</u> <u>CGC</u> <u>CGC</u> <u>CGC</u> | 126 |
| | | <u>C</u>GC <u>C</u>GC <u>C</u>GC <u>C</u>GC <u>C</u>GC <u>C</u>GC <u>C</u>GC <u>C</u>GC | 127 |
| | | <u>CGC</u> <u>CGC</u> <u>CGC</u> <u>CGC</u> <u>CGC</u> <u>CGC</u> <u>CGC</u> <u>CGC</u> | 128 |
| | | <u>C</u>GC <u>C</u>GC <u>C</u>GC <u>C</u>GC <u>C</u>GC <u>C</u>GC <u>C</u>GC <u>C</u>GC <u>C</u>GC | 129 |
| | | <u>CGC</u> <u>CGC</u> <u>CGC</u> <u>CGC</u> <u>CGC</u> <u>CGC</u> <u>CGC</u> <u>CGC</u> <u>CGC</u> | 130 |
| | | <u>C</u>GC <u>C</u>GC <u>C</u>GC <u>C</u>GC <u>C</u>GC <u>C</u>GC <u>C</u>GC <u>C</u>GC <u>C</u>GC <u>C</u>GC | 131 |
| | | CGC CGC CGC CGC CGC CGC CGC CGC CGC CGC | 132 |
| (CGG)n | | <u>C</u><u>C</u>G <u>C</u><u>C</u>G <u>C</u><u>C</u>G <u>C</u><u>C</u>G | 133 |
| | | C<u>C</u>G C<u>C</u>G C<u>C</u>G C<u>C</u>G | 134 |
| | | <u>C</u><u>C</u>G <u>C</u><u>C</u>G <u>C</u><u>C</u>G <u>C</u><u>C</u>G <u>C</u><u>C</u>G | 135 |
| | | C<u>C</u>G C<u>C</u>G C<u>C</u>G C<u>C</u>G C<u>C</u>G | 136 |
| | | <u>C</u><u>C</u>G <u>C</u><u>C</u>G <u>C</u><u>C</u>G <u>C</u><u>C</u>G <u>C</u><u>C</u>G <u>C</u><u>C</u>G | 137 |
| | | C<u>C</u>G C<u>C</u>G C<u>C</u>G C<u>C</u>G C<u>C</u>G C<u>C</u>G | 138 |
| | | <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G | 139 |
| | | C<u>C</u>G C<u>C</u>G C<u>C</u>G C<u>C</u>G C<u>C</u>G C<u>C</u>G C<u>C</u>G | 140 |
| | | <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G | 141 |
| | | C<u>C</u>G C<u>C</u>G C<u>C</u>G C<u>C</u>G C<u>C</u>G C<u>C</u>G C<u>C</u>G C<u>C</u>G | 142 |
| | | <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G | 143 |
| | | C<u>C</u>G C<u>C</u>G C<u>C</u>G C<u>C</u>G C<u>C</u>G C<u>C</u>G C<u>C</u>G C<u>C</u>G C<u>C</u>G | 144 |
| | | <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G <u>C</u><u>C</u>G | 145 |
| | | C<u>C</u>G C<u>C</u>G C<u>C</u>G C<u>C</u>G C<u>C</u>G C<u>C</u>G C<u>C</u>G C<u>C</u>G C<u>C</u>G C<u>C</u>G | 146 |
| (GAA)n | | <u>UU</u><u>C</u> <u>UU</u><u>C</u> <u>UU</u><u>C</u> <u>UU</u><u>C</u> | 147 |
| | | <u>UU</u><u>C</u> <u>UU</u><u>C</u> <u>UU</u><u>C</u> <u>UU</u><u>C</u> | 148 |
| | | <u>UU</u>C <u>UU</u>C <u>UU</u>C <u>UU</u>C <u>UU</u>C | 149 |
| | | <u>UU</u><u>C</u> <u>UU</u><u>C</u> <u>UU</u><u>C</u> <u>UU</u><u>C</u> <u>UU</u><u>C</u> | 150 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> | 151 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> | 152 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 153 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 154 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 155 |
| | | <u>UU</u><u>C</u> UUC UUC UUC UUC UU<u>C</u> | 156 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 157 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 158 |
| | | <u>UU</u>C <u>UU</u>C <u>UU</u>C <u>UU</u>C <u>UU</u>C <u>UU</u>C <u>UU</u>C <u>UU</u>C | 159 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 160 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 161 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 162 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 163 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 164 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 165 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 166 |
| | | <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> <u>UU</u><u>C</u> | 167 |
| (GCC)n | | GG<u>C</u> GG<u>C</u> GG<u>C</u> GG<u>C</u> | 168 |
| | | GG<u>C</u> GG<u>C</u> GG<u>C</u> GG<u>C</u> GG<u>C</u> | 169 |
| | | GG<u>C</u> GG<u>C</u> GG<u>C</u> GG<u>C</u> GG<u>C</u> GG<u>C</u> | 170 |

TABLE 2-continued

General structures of AONs. All AONs are 2'-O-methyl phosphorothioate AONs wherein <u>C</u> is 5-methylcytosine, <u>U</u> is 5-methyluracil, <u>A</u> is 2,6-diaminopurine, I is inosine and Q is an abasic monomer.

| Target Repeat | AON ID | AON Sequence (5'→3') | SEQ ID NO |
|---|---|---|---|
| | | GG<u>C</u> GG<u>C</u> GG<u>C</u> GG<u>C</u> GG<u>C</u> GG<u>C</u> GG<u>C</u> | 171 |
| | | GG<u>C</u> GG<u>C</u> GG<u>C</u> GG<u>C</u> GG<u>C</u> GG<u>C</u> GG<u>C</u> | 172 |
| | | GG<u>C</u> GGC GG<u>C</u> GGC GG<u>C</u> GGC GG<u>C</u> | 173 |
| | | GGC GGC GG<u>C</u> GGC GG<u>C</u> GGC GGC | 174 |
| | | GG<u>C</u> GG<u>C</u> GG<u>C</u> GG<u>C</u> GG<u>C</u> GG<u>C</u> GG<u>C</u> GG<u>C</u> | 175 |
| | | GG<u>C</u> GG<u>C</u> GG<u>C</u> GG<u>C</u> GG<u>C</u> GG<u>C</u> GG<u>C</u> GG<u>C</u> GG<u>C</u> | 176 |
| | | GG<u>C</u> GG<u>C</u> GG<u>C</u> GG<u>C</u> GG<u>C</u> GG<u>C</u> GG<u>C</u> GG<u>C</u> GG<u>C</u> GG<u>C</u> | 177 |
| (CCG)n | | <u>C</u>GG <u>C</u>GG <u>C</u>GG <u>C</u>GG | 178 |
| | | <u>C</u>GG <u>C</u>GG <u>C</u>GG <u>C</u>GG <u>C</u>GG | 179 |
| | | <u>C</u>GG <u>C</u>GG <u>C</u>GG <u>C</u>GG <u>C</u>GG <u>C</u>GG | 180 |
| | | <u>C</u>GG <u>C</u>GG <u>C</u>GG <u>C</u>GG <u>C</u>GG <u>C</u>GG <u>C</u>GG | 181 |
| | | <u>C</u>GG <u>C</u>GG <u>C</u>GG <u>C</u>GG <u>C</u>GG <u>C</u>GG <u>C</u>GG <u>C</u>GG | 182 |
| | | <u>C</u>GG <u>C</u>GG <u>C</u>GG <u>C</u>GG <u>C</u>GG <u>C</u>GG <u>C</u>GG <u>C</u>GG <u>C</u>GG | 183 |
| | | <u>C</u>GG <u>C</u>GG <u>C</u>GG <u>C</u>GG <u>C</u>GG <u>C</u>GG <u>C</u>GG <u>C</u>GG <u>C</u>GG <u>C</u>GG | 184 |
| (AUUCU)n | | AG<u>AAU</u> AG<u>AAU</u> AG<u>AAU</u> | 185 |
| | | AG<u>AAU</u> AG<u>AAU</u> AG<u>AAU</u> AG<u>AAU</u> | 186 |
| | | AG<u>AAU</u> AG<u>AAU</u> AG<u>AAU</u> AG<u>AAU</u> | 187 |
| | | AG<u>AAU</u> AG<u>AAU</u> AG<u>AAU</u> AG<u>AAU</u> | 188 |
| | | AG<u>AAU</u> AG<u>AAU</u> AG<u>AAU</u> AG<u>AAU</u> | 189 |
| | | AG<u>AAU</u> AG<u>AAU</u> AG<u>AAU</u> AG<u>AAU</u> AG<u>AAU</u> | 190 |
| | | AG<u>AAU</u> AG<u>AAU</u> AG<u>AAU</u> AG<u>AAU</u> AG<u>AAU</u> AG<u>AAU</u> | 191 |
| | | AG<u>AAU</u> AG<u>AAU</u> AG<u>AAU</u> AG<u>AAU</u> AG<u>AAU</u> AG<u>AAU</u> AG<u>AAU</u> | 192 |
| (CCUG)n | | <u>C</u>AGG <u>C</u>AGG <u>C</u>AGG | 193 |
| | | <u>C</u>AGG <u>C</u>AGG <u>C</u>AGG | 194 |
| | | <u>C</u>AGG <u>C</u>AGG <u>C</u>AGG <u>C</u>AGG | 195 |
| | | <u>C</u>AGG <u>C</u>AGG <u>C</u>AGG <u>C</u>AGG | 196 |
| | | <u>C</u>AGG <u>C</u>AGG <u>C</u>AGG <u>C</u>AGG <u>C</u>AGG | 197 |
| | | <u>C</u>AGG <u>C</u>AGG <u>C</u>AGG <u>C</u>AGG <u>C</u>AGG | 198 |
| | | <u>C</u>AGG <u>C</u>AGG <u>C</u>AGG <u>C</u>AGG <u>C</u>AGG | 199 |
| | | <u>C</u>AGG <u>C</u>AGG <u>C</u>AGG <u>C</u>AGG <u>C</u>AGG | 200 |
| | | <u>C</u>AGG <u>C</u>AGG <u>C</u>AGG <u>C</u>AGG <u>C</u>AGG <u>C</u>AGG | 201 |
| | | <u>C</u>AGG <u>C</u>AGG <u>C</u>AGG <u>C</u>AGG <u>C</u>AGG <u>C</u>AGG | 202 |
| | | <u>C</u>AGG <u>C</u>AGG <u>C</u>AGG <u>C</u>AGG <u>C</u>AGG <u>C</u>AGG <u>C</u>AGG | 203 |
| | | <u>C</u>AGG <u>C</u>AGG <u>C</u>AGG <u>C</u>AGG <u>C</u>AGG <u>C</u>AGG <u>C</u>AGG | 204 |
| | | <u>C</u>AGG <u>C</u>AGG <u>C</u>AGG <u>C</u>AGG <u>C</u>AGG <u>C</u>AGG <u>C</u>AGG <u>C</u>AGG | 205 |
| | | <u>C</u>AGG <u>C</u>AGG <u>C</u>AGG <u>C</u>AGG <u>C</u>AGG <u>C</u>AGG <u>C</u>AGG <u>C</u>AGG | 206 |
| | | <u>C</u>AGG <u>C</u>AGG <u>C</u>AGG <u>C</u>AGG <u>C</u>AGG <u>C</u>AGG <u>C</u>AGG <u>C</u>AGG <u>C</u>AGG | 207 |
| | | <u>C</u>AGG <u>C</u>AGG <u>C</u>AGG <u>C</u>AGG <u>C</u>AGG <u>C</u>AGG <u>C</u>AGG <u>C</u>AGG <u>C</u>AGG | 208 |
| (GGGGCC)n | PS1252 | GG<u>C</u>U<u>CC</u> GG<u>C</u>U<u>CC</u> GG<u>C</u>U<u>C</u> | 209 |
| | | GG<u>C</u>Q<u>CC</u> GG<u>C</u>Q<u>CC</u> GG<u>C</u>Q<u>CC</u> | 210 |
| | | GG<u>C</u>U<u>CC</u> GG<u>C</u>U<u>CC</u> GG<u>C</u>U<u>CC</u> | 211 |
| | | GG<u>C</u>U<u>CC</u> GG<u>C</u>U<u>CC</u> GG<u>C</u>U<u>CC</u> GG<u>C</u>U<u>CC</u> | 212 |
| | | GG<u>C</u>Q<u>CC</u> GG<u>C</u>Q<u>CC</u> GG<u>C</u>Q<u>CC</u> GG<u>C</u>Q<u>CC</u> | 213 |
| | | GG<u>C</u>I<u>CC</u> GG<u>C</u>I<u>CC</u> GG<u>C</u>I<u>CC</u> GG<u>C</u>I<u>CC</u> | 214 |
| | | GG<u>CC</u>U<u>C</u> GG<u>CC</u>U<u>C</u> GG<u>CC</u>U<u>C</u> GG<u>CC</u>U<u>C</u> | 215 |

EXAMPLES

Example 1

Introduction

The particular characteristics of a chosen antisense oligonucleotide (AON) chemistry may at least in part enhance binding affinity and stability, enhance activity, improve safety, and/or reduce cost of goods by reducing length or improving synthesis and/or purification procedures. This example describes the comparative analysis of the activity of AONs designed to target the expanded $(CAG)_n$ repeat in HTT transcripts in HD fibroblasts in vitro, and includes AONs with either 5-methylcytosines $(XYG)_7$, wherein X is 5-methylcytosine and Y=U being also identified as SEQ ID NO:90 (and derived from SEQ ID NO:2), or 5-methyluracils $(XYG)_7$, wherein X=C and Y=5-methyluracil being also identified as SEQ ID NO: 97 (and derived from SEQ ID NO:3).

Materials and Methods

Cell Culture.

Patient derived HD fibroblasts (GM04022) (purchased from Coriell Cell Repositories, Camden, USA) were cultured at 37° C. and 5% $CO_2$ in Minimal Essential Medium (MEM) (Gibco Invitrogen, Carlsbad, USA) with 15% heat inactivated Fetal Bovine Serum (FBS) (Clontech, Palo Alto USA), 1% Glutamax (Gibco) and 100 U/ml penicillin/streptomycin (P/S) (Gibco).

Oligonucleotides.

The AONs were fully 2'-O-methyl phosphorothioate modified: PS659; (XYG)$_7$, wherein X is 5-methylcytosine and Y=U being also identified as SEQ ID NO: 90 (and derived from SEQ ID NO:2), and PS661; (XYG)$_7$, wherein X=C and Y=5-methyluracil being also identified as SEQ ID NO:97 (and derived from SEQ ID NO:3).

Transfection.

Cells were transfected with AONs complexed with PEI (2 µL per µg AON, in 0.15 M NaCl). AON-PEI complex was added in MEM medium with 5% FBS to cells to a final AON concentration varying from 0.5-200 nM. Fresh medium was supplemented after four hours and after 24 hours RNA was isolated.

RNA Isolation.

RNA from cultured cells was isolated using the Aurum Total RNA Mini Kit (Bio-Rad, Hercules, Calif.) according to the manufacturer's protocol.

RT-PCR and Lab-On-a-Chip Analysis.

Approximately 200 ng RNA was subjected to cDNA synthesis with random hexamers using the SuperScript first-strand synthesis system (Invitrogen) in a total volume of 20 µL. PCR was performed with primers for HTT (across the CAG repeat) and β-actin. The PCR program started with a 4 min initial denaturation at 95° C., followed by 35 cycles of 30 sec denaturation at 94° C., 30 sec annealing at 60° C., 45 sec elongation at 72° C., after which a final elongation step was performed at 72° C. for 7 min. Lab-on-a-Chip was performed on the Agilent 2100 Bioanalyzer (Agilent Technologies, Waldbronn, Germany), using the Agilent DNA 1000 Kit. Expression levels were normalized for β-actin levels and relative to transcript levels without transfection. The following primers were used:

```
HTT forward;
                             (SEQ ID NO: 70)
5'-ATGGCGACCCTGGAAAAGCTGAT-3'

HTT reverse:
                             (SEQ ID NO: 71)
5'-TGAGGCAGCAGCGGCTG-3'

β-actin forward;
                             (SEQ ID NO: 72)
5'-GGACTTCGAGCAAGAGATGG-3'

β-actin reverse;
                             (SEQ ID NO: 73)
5'-AGCACTGTGTTGGCGTACAG-3'
```

Results

Figure 1B:
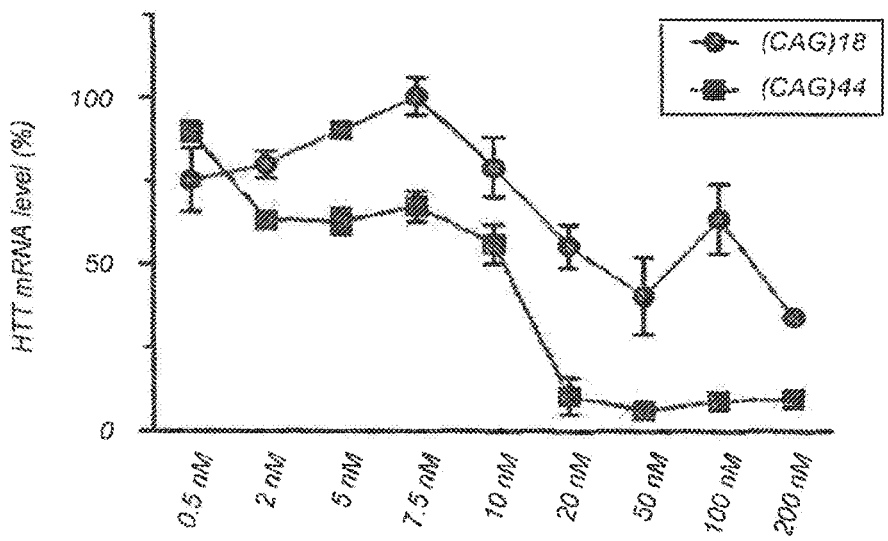

Both PS659 (SEQ ID NO: 90 derived from SEQ ID NO:2) and PS661 (SEQ ID NO: 97 derived from SEQ ID NO:3) were highly effective and reduced the HTT transcripts in HD fibroblasts in a dose-dependent manner (FIGS. 1A-1B). Both AONs also showed a preference for the allele with the expanded CAG repeats. PS659 (SEQ ID NO: 90 derived from SEQ ID NO:2) was more effective and more allele-specific at lower concentrations (strongest effect at 5 nM) (FIG. 1A) than PS661 (SEQ ID NO: 97 derived from SEQ ID NO:3) (strongest effect at 20 nM) (FIG. 1B).

Example 2

Introduction

PS659 (XYG)$_7$, wherein X is 5-methylcytosine and Y=U also identified as SEQ ID NO: 90 (derived from SEQ ID NO:2), was selected from in vitro studies as most efficient and safe candidate. This example describes its activity in a transgenic HD rat model after a series of direct intraventricular injections.

Materials and Methods

Animals.

Transgenic HD rats carry a truncated Huntington cDNA fragment with 51 CAG repeats under the control of the native rat Huntington promoter. The expressed gene product is about 75 kDa, corresponding to 22% of the full-length Huntington (cDNA position 324-2321, amino acid position 1-709/825, corresponding to exon 1-16), under the control of 886 bp of the rat Huntington promoter (von Hörsten S. et al.). All animal experiments were approved by the Institutional Animal Care and Use Committees of the Maastricht University, Maastricht.

Oligonucleotides.

PS659 (XYG)$_7$, wherein X is 5-methylcytosine and Y=U also identified as SEQ ID NO: 90 (derived from SEQ ID NO:2), is a fully 2'-O-methyl phosphorothioate modified AON.

In Vivo Treatment.

Transgenic HD rats received 15 times an intraventricular injection at a final dose of 200 µg PS659 also identified as SEQ ID NO: 90 (derived from SEQ ID NO:2) during 18 weeks. Control HD rats received vehicle only. Rats were sacrificed one week after the final injection.

RNA Isolation.

RNA from brain tissue was isolated using RNA-Bee reagent (Tel Test, Inc). In brief, tissue samples were homogenized in MagNA Lyser green bead tubes (Roche) by adding RNA-Bee (50 mg tissue/mL RNA-Bee) and homogenizing using a MagNA Lyser instrument (Roche). Lysate was transferred to a new tube, chloroform (SIGMA) was added (0.2 mL per mL RNA-Bee), mixed, incubated on ice for 5 minutes and centrifuged at 13,000 rpm for 15 minutes at 4° C. The upper aqueous phase was collected and an equal volume isopropanol (SIGMA) was added, followed by a 1 hour incubation period at 4° C. and centrifugation (13,000 rpm, 15 min, 4° C.). The RNA precipitate was washed with 70% (v/v) ethanol (BioSolve), air dried and dissolved in MilliQ.

Quantitative RT-PCR Analysis.

Approximately 200 ng was subjected to cDNA synthesis with random hexamers using the SuperScript first-strand synthesis system (Invitrogen) in a total volume of 20 µL. 3 µL of 1/40 cDNA dilution preparation was subsequently used in a quantitative PCR analysis according to standard procedures in presence of iQ™ SYBR® Green Supermix (Bio-Rad). Quantitative PCR primers were designed based on NCBI database sequence information. Product identity was confirmed by DNA sequencing. The signal for Rab2 and YWHAZ was used for normalization. The following primers were used:

```
Rat Htt-F;
                             (SEQ ID NO: 74)
5'-CGCCGCCTCCTCAGCTTC-3'

Rat Htt-R;
                             (SEQ ID NO: 75)
5'-GAGAGTTCCTTCTTTGGTCGGTGC-3'

Rab2-F;
                             (SEQ ID NO: 76)
5'-TGGGAAACAGATAAAACTCCAGA-3'
```

-continued

```
Rab2-R;
                                              (SEQ ID NO: 77)
5'-AATATGACCTTGTGATAGAACGAAAG-3'

YWHAZ-F;
                                              (SEQ ID NO: 78)
5'-AAATGAGCTGGTGCAGAAGG-3'

YWHAZ-R;
                                              (SEQ ID NO: 79)
5'-GGCTGCCATGTCATCGTAT-3'
```

Results

PS659 (also identified as SEQ ID NO: 90 or derived from SEQ ID NO: 2) reduced transgenic Htt transcript levels in cortex (FIG. 2A), hippocampus (FIG. 2B), olfactory bulb (FIG. 2C) as well as in thalamus (FIG. 2D) when compared to saline treated rats. These results demonstrate that PS659 (also identified as SEQ ID NO: 90 or derived from SEQ ID NO; 2) is effective in vivo after direct intraventricular injection.

LIST OF REFERENCES

Aartsma-Rus et al., Hum Mol Gen 2003; 12(8):907-14.
Arai K et al. Bioorg. Med. Chem. 2011, 21, 6285
Bauer et al., 2009; J Neurochem. 110:1737-65
Braida C., et al, Human Molecular Genetics, 2010, vol 9: 1399-1412
Bruno et al., Adv Drug Deliv Rev. 2011; 63(13):1210-26
Diebold et al., 2006, Eur J Immunol; 36(12): 3256-67
Evers et al. PLoS ONE 2011, 6 (9) e24308
Huang et al., 1998 Somat Cell Molec Gen 24:217-33;
Krieg A M. et al., Nature 1995; 374: 546-549.
Krieg, A. M., Curr. Opin. Immunol. 2000; 12: 35-43.
Kumar L, Pharm. Technol. 2008, 3, 128.
Muchowski et al., 2002 PNAS 99: 727-32
Mulders et al. PNAS 2009 106(33); p 13915-20
Peacock H et al. J. Am. Chem. Soc. 2011, 133, 9200
Popovic P J. et al. J of Immunol 2006; 177: 8701-8707.
Roon-Mom et al., 2002 Mol Brain Res 109: 1-10
Ropper A H. and Brown R H., 2005 Principles of neurology. 8th Ed. New York:
McGraw-Hill, 2005.
Ross et al., 2011; Lancet Neurol. 10:83-98
Rigo, F, et al, 2012, Nature chemical biology, 8: 555-561.
Steffan et al., 2000 PNAS 97: 6763-68
von Horsten S. et al. Hum Mol Genet. 2003; 12(6):617-24
Wagner, H., Adv. Immunol. 1999; 73: 329-368.
Yu R Z., Anal Biochem 2002; 304: 19-25.

The invention claimed is:

1. A method for treating, delaying, ameliorating and/or preventing a spinocerebellar ataxia (SCA), spinal and bulbar muscular atrophy (SBMA), or dentatorubral-pallidoluysian atrophy (DRPLA) in a subject, comprising providing to the subject an antisense oligonucleotide comprising a 2'-O-methyl RNA nucleotide residue, having a backbone wherein at least one phosphate moiety is replaced by a phosphorothioate moiety, and comprising a repetitive nucleotide unit (XYG)m, wherein m is an integer from 4 to 12 and each X is C or 5-methylcytosine, and each Y is U or 5-methyluracil, wherein at least one X is 5-methylcytosine, wherein said oligonucleotide is able to hybridize to a (CAG)n repetitive nucleotide unit.

2. The method of claim 1, wherein said oligonucleotide consists of a repetitive nucleotide unit (XYG)m, wherein m is an integer from 4 to 12 and each X is C or 5-methylcytosine, and each Y is U or 5-methyluracil, wherein at least one X is 5-methylcytosine and/or at least one Y is 5-methyluracil.

3. The method of claim 1, wherein said oligonucleotide is such that each X is 5-methylcytosine and/or each Y is 5-methyluracil.

4. The method of claim 1, wherein said oligonucleotide is such that m is 5 or 6 or 7 or 8 or 9 or 10 or 11 or 12.

5. The method of claim 4, wherein said oligonucleotide comprises a repetitive nucleotide unit (XYG)7, wherein each X is 5-methylcytosine and each Y is a uracil (SEQ ID NO: 2).

6. The method of claim 4, wherein said oligonucleotide is such that m is 7.

7. The method of claim 1, wherein the sequence of said oligonucleotide comprises any of SEQ ID NO: 90, 96, 104-109, 111, 113, 115, and 117.

8. The method of claim 7, wherein the base sequence of said oligonucleotide comprises SEQ ID NO:90.

9. The method of claim 1, wherein said oligonucleotide is a single-stranded oligonucleotide.

10. The method of claim 1 wherein said oligonucleotide has a length of from 12 to 36 nucleotides.

11. The method of claim 1, wherein said oligonucleotide remain in association to its target when there are up to 20% of mismatched nucleotides.

12. The method of claim 1, wherein said oligonucleotide is at least 90% reverse complementary with said repetitive nucleotide unit.

13. The method of claim 1, wherein said oligonucleotide has an improved parameter by comparison to a corresponding oligonucleotide comprising a 2'-O-methyl RNA nucleotide residue and having a backbone wherein at least one phosphate moiety is replaced by a phosphorothioate moiety, without a 5-methylcytosine, and/or a 5-methyluracil and/or a 2,6-diaminopurine.

14. The method of claim 1, wherein said oligonucleotide reduces a detectable amount of mutant transcript and/or reduces the translation of said mutant transcript and thus the amount of mutant protein.

15. The method of claim 14, wherein said reduction of mutant protein reduces protein aggregates in nucleus and/or cytoplasm.

16. The method of claim 1, wherein said oligonucleotide is present in a composition.

17. The method of claim 16, wherein said composition comprises at least one excipient that may further aid in enhancing the targeting and/or delivery of said composition and/or said oligonucleotide to a tissue and/or cell and/or into a tissue and/or cell.

18. The method of claim 1, wherein said oligonucleotide preferentially hybridizes to a disease-associated or disease-causing transcript and leaves a function of a normal transcript relatively unaffected.

19. The method of claim 1, wherein said subject has DRPLA, SBMA, or SCA type 1, 2, 3, 6, 7, 12 or 17.

20. The method of claim 19, wherein
said SCA type 1 is caused by CAG repeat expansions in the transcripts of ATXN1 (SEQ ID NO:81),
said SCA type 2 is caused by CAG repeat expansions in the transcripts of ATXN2 (SEQ ID NO: 82),
said SCA type 3 is caused by CAG repeat expansions in the transcripts of ATXN3 (SEQ ID NO: 83),
said SCA type 6 is caused by CAG repeat expansions in the transcripts of CACNA1A (SEQ ID NO:84), said SCA type 7 is caused by CAG repeat expansions in the transcripts of ATXN7 (SEQ ID NO: 85),
said SCA type 12 is caused by CAG repeat expansions in the transcripts of PPP2R2B (SEQ ID NO: 86), and
said SCA type 17 is caused by CAG repeat expansions in the transcripts of TBP (SEQ ID NO: 87) genes.

21. The method of claim 1, wherein said SBMA is caused by CAG repeat expansions in the transcripts of AR (SEQ ID NO: 88), and said DRPLA is caused by CAG repeat expansions in the transcripts of ATN1 (SEQ ID NO: 89) genes.

22. The method of claim 1, wherein the antisense oligonucleotide is provided by intrathecal administration.

23. The method of claim 4, wherein said oligonucleotide consists of a repetitive nucleotide unit (XYG)7, wherein each X is 5-methylcytosine and each Y is a uracil (SEQ ID NO: 2).

24. A method for treating, delaying, ameliorating and/or preventing a spinocerebellar ataxia (SCA) type 1 or type 3 in a subject, comprising providing to the subject an antisense oligonucleotide which consists of 2'-O-methyl RNA nucleotide residues and has a backbone wherein all phosphate moieties are replaced by a phosphorothioate moiety, and which comprises the base sequence of SEQ ID NO: 90.

25. The method of claim 23, wherein the antisense oligonucleotide is provided by intrathecal administration.

* * * * *